United States Patent
Sibley et al.

(10) Patent No.: US 11,351,233 B2
(45) Date of Patent: Jun. 7, 2022

(54) ANTIGENS FOR DETECTING TOXOPLASMA INFECTION BY MONITORING CELLULAR IMMUNITY

(71) Applicant: Washington University, St. Louis, MO (US)

(72) Inventors: Laurence David Sibley, St. Louis, MO (US); Kevin M. Brown, St. Louis, MO (US); Qiuling Wang, St. Louis, MO (US); Iti Saraav, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 16/347,510

(22) PCT Filed: Nov. 3, 2017

(86) PCT No.: PCT/US2017/059978
§ 371 (c)(1),
(2) Date: May 3, 2019

(87) PCT Pub. No.: WO2018/085685
PCT Pub. Date: May 11, 2018

(65) Prior Publication Data
US 2019/0275124 A1    Sep. 12, 2019

Related U.S. Application Data

(60) Provisional application No. 62/417,136, filed on Nov. 3, 2016, provisional application No. 62/550,393, filed on Aug. 25, 2017.

(51) Int. Cl.
| *C12Q 1/00* | (2006.01) |
| *A61K 39/00* | (2006.01) |
| *A61M 5/315* | (2006.01) |
| *A61K 39/002* | (2006.01) |

(52) U.S. Cl.
CPC ........ *A61K 39/0002* (2013.01); *A61K 39/002* (2013.01); *A61M 5/31531* (2013.01); *A61K 2039/54* (2013.01); *A61K 2039/572* (2013.01); *A61K 2039/6087* (2013.01)

(58) Field of Classification Search
None
See application file for complete search history.

(56) References Cited

U.S. PATENT DOCUMENTS
2010/0203085 A1    8/2010    Bzik et al.

FOREIGN PATENT DOCUMENTS
| CN | 104897891 A | 9/2015 |
| EP | 2889040 A1 | 7/2015 |
| WO | 2001064243 A2 | 9/2001 |
| WO | 2018085685 A1 | 5/2018 |
| WO | 2021034963 A1 | 2/2021 |

OTHER PUBLICATIONS

Lourenco etal (Microbes and Infection. 2006. 8: 12441251).*
Extended European Search Report dated Mar. 30, 2020 from Patent Application No. 17868052.6; 5 pgs.
Allen, I., "Delayed-Type Hypersensitivity Models in Mice," Irving C. Allen (ed.), Mouse Models of Innate Immunity: Methods and Protocols, Methods Mol. Biol., 2013, pp. 101-107, vol. 1031, Chapter 13, Springer Science+Business Media, LLC.
Beghetto, E. et al., "A Combination of Antigenic Regions of Toxoplasma gondii Microneme Proteins Induces Protective Immunity against Oral Infection with Parasite Cysts," JID, Feb. 2005, pp. 637-645, vol. 191.
Behnke, M. et al., "Coordinated Progression through Two Subtranscriptomes Underlies the Tachyzoite Cycle of Toxoplasma gondii," PLoS One, Aug. 2010, pp. 1-20, vol. 5, No. 8, e12354.
Black, C., "Delayed type hypersensitivity: Current theories with a historic perspective," Dermatol Online J., 1999, pp. 1-11, vol. 5, No. 1.
Blumenschein, T. et al., "Atomic resolution insight into host cell recognition by Toxoplasma gondii," EMBO J., 2007, pp. 2808-2820, vol. 26.
Brecht, S. et al., "The Toxoplasma Micronemal Protein MIC4 Is an Adhesin Composed of Six Conserved Apple Domains," J. Biol. Chem., Feb. 2001, pp. 4119-4127, vol. 276, No. 6.
Brown, K. et al., "Serum Albumin Stimulates Protein Kinase G-dependent Microneme Secretion in Toxoplasma gondii," J. Biol. Chem., Apr. 2016, pp. 9554-9565, vol. 291, No. 18.
Brydges, S. et al., "Molecular characterization of TgMIC5, a proteolytically processed antigen secreted from the micronemes of Toxoplasma gondii," Mol. Biochem. Parasitol., Nov. 2000, pp. 51-66, vol. 111, No. 1.
Carruthers, V. et al., "Sequential protein secretion from three distinct organelles of Toxoplasma gondii accompanies invasion of human fibroblasts," Eur. J. Cell Biol., Jun. 1997, pp. 114-123, vol. 73, No. 2.
Carruthers, V. et al., "Ethanol and acetaldehyde elevate intracellular [Ca2+] calcium and stimulate microneme discharge in Toxoplasma gondii," Biochem J., 1999, pp. 379-386, vol. 342.
Carruthers, V. et al., "Secretion of micronemal proteins is associated with Toxoplasma invasion of host cells," Cell Microbiol., 1999, pp. 225-235, vol. 1, No. 3.
Carruthers, V. et al., "Mobilization of intracellular calcium stimulates microneme discharge in Toxoplasma gondii," Mol. Microbiol., 1999, pp. 421-428, vol. 31, No. 2.
Cerede, O. et al., "The Toxoplasma gondii protein MIC3 requires pro-peptide cleavage and dimerization to function as adhesin," EMBO J., 2002, pp. 2526-2536, vol. 21, No. 11.

(Continued)

*Primary Examiner* — Jennifer E Graser
(74) *Attorney, Agent, or Firm* — Polsinelli PC

(57) ABSTRACT

Antigens of *Toxoplasma gondii* that provide specific and strong delayed type hypersensitivity (DTH) immune response, or which stimulate IFN-y secretion, are used for testing subjects for infection. Any skin testing format may be adapted for testing for the delayed type hypersensitivity, including a patch, a needle, or a prong. Presence of DTH indicates infection. Alternate methods of detecting a T cell response including monitoring IFN-y secretion may be used.

7 Claims, 5 Drawing Sheets
(4 of 5 Drawing Sheet(s) Filed in Color)

Specification includes a Sequence Listing.

(56) References Cited

OTHER PUBLICATIONS

Erskine, C. et al., "MHC Class II Epitope Nesting Modulates Dendritic Cell Function and Improves Generation of Antigen-specific CD4 Helper T Cells," J. Immunol., 2011, pp. 316-324, vol. 187.

Etheridge, R. et al., "The Toxoplasma Pseudokinase ROP5 Forms Complexes with ROP18 and ROP17 Kinases that Synergize to Control Acute Virulence in Mice," Cell Host Microbe, May 2014, pp. 537-550, vol. 15.

Frenkel, J., "Dermal Hypersensitivity to Toxoplasma Antigens (Toxoplasmins)," Exp. Biol. Med., 1948, pp. 634-639, vol. 68.

Friedrich, N. et al., "Members of a Novel Protein Family Containing Microneme Adhesive Repeat Domains Act as Sialic Acid-binding Lectins during Host Cell Invasion by Apicomplexan Parasites," J. Biol. Chem., Jan. 2010, pp. 2064-2076, vol. 285, No. 3.

Garnett, J. et al., "Detailed insights from microarray and crystallographic studies into carbohydrate recognition by microneme protein 1 (MIC1) of Toxoplasma gondii," Protein Sci., 2009, pp. 1935-1947, vol. 18.

Gross, S. et al., "Bioluminescence imaging of myeloperoxidase activity in vivo," NIH Public Access Author Manuscript, Mar. 3, 2010, pp. 1-15, published in final edited form as: Nat. Med., Apr. 2009, pp. 455-461, vol. 15, No. 4.

Hoff, E. et al., "Toxoplasma gondii: Molecular Cloning and Characterization of a Novel 18-kDa Secretory Antigen, TgMIC10," Exp. Parasitol., 2001, pp. 77-88, vol. 97, No. 2.

Hoffmann, C. et al., "Evolving characteristics of toxoplasmosis in patients infected with human immunodeficiency virus-1: clinical course and Toxoplasma gondii-specific immune responses," Clin. Microbiol. Infect., 2007, pp. 510-515, vol. 13.

Holec, L. et al., "Toxoplasma gondii: Enzyme-linked immunosorbent assay using different fragments of recombinant microneme protein 1 (MIC1) for detection of immunoglobulin G antibodies," Exp. Parasitol, 2008, pp. 1-6, vol. 119.

Holec-Gasior, L. et al., "Toxoplasma gondii Recombinant Antigens as Tools for Serodiagnosis of Human Toxoplasmosis: Current Status of Studies," Clin. Vaccine Immunol., Sep. 2013, pp. 1343-1351, vol. 20, No. 9.

Huynh, M-H et al., "Rapid invasion of host cells by Toxoplasma requires secretion of the MIC2-M2AP adhesive protein complex," EMBO J., 2003, pp. 2082-2090, vol. 22, No. 9.

International Search Report and Written Opinion dated Jan. 26, 2018 from related Patent Application No. PCT/US2017/059978; 11 pgs.

Ismael, A. et al., "The MIC3 Gene of Toxoplasma gondii Is a Novel Potent Vaccine Candidate against Toxoplasmosis," Infection and Immunity, Nov. 2003, pp. 6222-6228, vol. 71, No. 11.

Jacobs, D. et al., "Inhibition of the Mitogenic Response to Lipopolysaccharide (LPS) in Mouse Spleen Cells by Polymyxin B," J. Immunol., Jan. 1977, pp. 21-27, vol. 118, No. 1.

Khan, A. et al., "Geographic Separation of Domestic and Wild Strains of Toxoplasma gondii in French Guiana Correlates with a Monomorphic Version of Chromosome1a," PLOS Negl. Trap. Dis., Sep. 2014, pp. 1-12, vol. 8, No. 9, e3182.

Kong, J. et al., "Serotyping of Toxoplasma gondii infections in humans using synthetic peptides," J. Infect. Dis., May 2003, pp. 1484-1495, vol. 187, No. 9.

Lourenco, E. et al., "Immunization with MIC1 and MIC4 induces protective immunity against Toxoplasma gondii," Microbes Infect., Apr. 2006, pp. 1244-1251, vol. 8, No. 5.

Mercier, C. et al., "Toxoplasma secretory granules: one population or more?," Trends Parasitol., 2015, pp. 60-71, vol. 31.

Moire, N. et al., "Mic1-3KO tachyzoite a live attenuated vaccine candidate against toxoplasmosis derived from a type I strain shows features of type II strain," Exp. Parasitol., 2009, pp. 111-117, vol. 123.

Nielsen, M. et al., "MHC Class II epitope predictive algorithms," Immunol., 2010, pp. 319-328, vol. 130.

Petsch, D. et al., "Endotoxin removal from protein solutions," J. Biotechnol., 2000, pp. 97-119, vol. 76.

Philpott, D. et al., "The role of Toll-like receptors and Nod proteins in bacterial infection," Mol. Immunol., Nov. 2004, pp. 1099-1108, vol. 41, No. 11.

Rougier, D. et al., "Detection of Toxoplasmic Immunity by Multipuncture Skin Test With Excretory-Secretory Antigen," Lancet, Jul. 1985, pp. 121-123, vol. 326, No. 8447.

Saouros, S. et al., "A Novel Galectin-like Domain from Toxoplasma gondii Micronemal Protein 1 Assists the Folding, Assembly, and Transport of a Cell Adhesion Complex," J. Biol. Chem., Nov. 2005, p. 38583-38591, vol. 280, No. 46.

Saraav, I. et al., "Secretory Microneme Proteins Induce T-Cell Recall Responses in Mice Chronically Infected with Toxoplasma gondii," mSphere, Jan./Feb. 2019, pp. 1-13, vol. 4, No. 1, e00711-18.

Sawmynaden, K. et al., "Structural insights into microneme protein assembly reveal a new mode of EGF domain recognition," EMBO Rep., 2008, pp. 1149-1155, vol. 9, No. 11.

Sedgwick, J. et al., "A Solid-Phase Immunoenzymatic Technique for the Enumeration of Specific Antibody-Secreting Cells," J. Immunol. Methods, 1983, pp. 301-309, vol. 57.

Sioud, M. et al., "A novel peptide carrier for efficient targeting of antigens and nucleic acids to dendritic cells," FASEB J., Aug. 2013, pp. 3272-3283, vol. 27, No. 8.

Veprekova, A. et al., "Approximative Molecular Weight of the Active Component in Toxoplasmin," Folia Parasitol. (Praha), 1978, pp. 273-275, vol. 25.

Vukmanovic-Stejic, M. et al., "Mantoux Test as a model for a secondary immune response in humans," Immunol. Lett., Nov. 2006, pp. 93-101, vol. 107, No. 2.

Wang, P. et al., "A Systematic Assessment of MHC Class II Peptide Binding Predictions and Evaluation of a Consensus Approach," PLoS Comput. Biol., 2008, pp. 1-10, vol. 4, No. 4, e1000048.

International Search Report and Written Opinion dated Jan. 15, 2021 from related Patent Application No. PCT/US2020/047048; 11 pgs.

Office Action dated Jan. 27, 2021 from related European Patent Application No. 17868052.6; 4 pgs.

Reiss, M. et al., "Identification and Characterization of an Escorter for Two Secretory Adhesins in Toxoplasma gondii," J. Cell Biol., Feb. 2001, pp. 563-578, vol. 152, No. 3.

Office Action dated Nov. 30, 2021 from related European Patent Application No. 17868052.6; 4 pgs.

\* cited by examiner

| Protein | Molecular Mass (kDa) | Endotoxin level (EU/mL) Before | Endotoxin level (EU/mL) After |
|---|---|---|---|
| MIC-1 | 48.6 | 2.878 | 0.051 |
| MIC 3 | 40.5 | 3.209 | 0.048 |
| MIC 4 | 63.0 | 3.212 | 0.068 |
| MIC 6 | 36.7 | 3.003 | 0.053 |
| SUMO | 12.5 | 3.124 | 0.071 |

ANTIGENS FOR DETECTING TOXOPLASMA INFECTION BY MONITORING CELLULAR IMMUNITY

CROSS REFERENCE TO RELATED APPLICATIONS

This application claims the benefit of International Application number PCT/US2017/059978, filed Nov. 03,2017 and U.S. Provisional Application No. 62/417,136, filed Nov. 3, 2016 and U.S. Provisional Application No. 62/550,393, filed Aug. 25, 2017, each of the disclosures of which are hereby incorporated by reference in their entirety.

TECHNICAL FIELD OF THE INVENTION

This invention is related to the area of clinical testing. In particular, it relates to cellular immune responses including delayed type hypersensitivity reactions and cytokine release, or interferon gamma secretion assays, and their use in diagnosis of toxoplasmosis.

BACKGROUND OF THE INVENTION

In *Toxoplasma gondii*, there are three main compartments, called dense granules (GRA proteins), rhoptries (ROP), and micronemes (MIC proteins), which release antigens into the extracellular milieu (Carruthers V B, Sibley L D. 1997. *Sequential protein secretion from three distinct organelles of Toxoplasma gondii accompanies invasion of human fibroblasts*. Eur J Cell Biol 73:114-123). Although both GRA and MIC compartments release antigens constitutively at low levels, micronemes can be stimulated to release large amounts of antigen in response to certain environmental cues, such as contact with host cells or other host factors (Carruthers V B, Giddings O K, Sibley L D. 1999. *Secretion of micronemal proteins is associated with Toxoplasma invasion of host cells*. Cell Microbiol 1:225-236.; Carruthers V B, Sibley L D. 1997. *Sequential protein secretion from three distinct organelles of Toxoplasma gondii accompanies invasion of human fibroblasts*. Eur J Cell Biol 73:114-123.; Carruthers V B, Sibley L D. 1999. *Mobilization of intracellular calcium stimulates microneme discharge in Toxoplasma gondii*. Mol Microbiol 31:421-428.). Collectively, proteins that are released either constitutively or in a regulated fashion have been defined as "excretory secretory antigens (ESA)."

The ESA fraction is enriched in secretory microneme (MIC) proteins but also contains constitutively secreted dense granule (GRA) proteins. Several MIC and GRA proteins have been described. Previous studies have shown that MIC2, and its binding partner MIC2 associated protein (M2AP), are abundant components of ESA (Huynh M H, Barenau K E, Harper J M, Beatty W L, Sibley L D, Carruthers V B. 2003. *Rapid invasion of host cells by Toxoplasma requires secretion of the MIC2-M2AP adhesive protein complex*. EMBO J 22:2082-2090.). Additionally, MIC5 (Brydges S D, Sherman G D, Nockemann S, Loyens A, Daubener W, Dubremetz J, Carruthers V B. 2000. *Molecular characterization of TgMIC5, a proteolytically processed antigen secreted from the micronemes of Toxoplasma gondii*. Mol Biochem Parasitol 111:51-66.) and MIC10 (Hoff E F, Cook S H, Sherman G D, Harper J M, Ferguson D J, Dubremetz J F, Carruthers V B. 2001. *Toxoplasma gondii: molecular cloning and characterization of a novel 18-kDa secretory antigen, TgMIC10*. Exp Parasitol 97:77-88.) have been studied as soluble micronemal proteins that are immunogenic. Several MIC proteins interact: for example MIC1, MIC4 and MICE form a complex involved in recognition of host carbohydrates (Friedrich N, Santos J M, Liu Y, Palma A S, Leon E, Saouros S, Kiso M, Blackman M J, Matthews S, Feizi T, Soldati-Favre D. J Biol Chem. 2010 285:2064-76., Blumenschein T M, Friedrich N, Childs R A, Saouros S, Carpenter E P, Campanero-Rhodes M A, Simpson P, Chai W, Koutroukides T, Blackman M J, Feizi T, Soldati-Favre D, Matthews S. EMBO J. 2007 26:2808-20) Gene deletions of MIC1 or MIC3 alone do not have a profound effect on invasion, but the double mutant is attenuated, indicating these proteins plan complementary roles (Moiré N, Dion S, Lebrun M, Dubremetz J F, Dimier-Poisson I. Exp Parasitol. 2009 123:111-7). MIC1 has been used in a variety of immunodiagnostic assays based on detection of antibodies that react to this protein (Holec L, Gasior A, Brillowska-Dabrowska A, Kur J. Exp Parasitol. 2008 119:1-6) or to hybrid proteins containing MIC1 and other parasite antigens (Holec-Gasior L, Ferra B, Drapala D. Clin Vaccine Immunol. 2012 19:1977-9). As well, MIC1 and MIC4 have been used in vaccination studies in mice (Lourenco E V, Bernardes E S, Silva N M, Mineo J R, Panunto-Castelo A, Roque-Barreira M C. Microbes Infect. 2006 8:1244-51). Other studies have shown that the secretory proteins GRA4, GRA6, and GRA7 are targets of the immune response (Mercier C, Cesbron-Delauw M F. 2015. *Toxoplasma secretory granules: one population or more?* Trends Parasitol 31:60-71.).

Delayed type hypersensitivity (DTH) responses are driven by cellular immune responses to antigens (Black C A. 1999. *Delayed type hypersensitivity: current theories with an historic perspective*. Dermatol Online J 5:7.). Typically a test antigen is injected in the skin of the ear, flank, or footpad and swelling measured 24-48 hr later (Allen I C. 2013. *Delayed-type hypersensitivity models in mice*. Methods Mol Biol 1031:101-107.). The most well-known test uses tuberculin, an extract of purified protein derivative (PPD) from mycobacteria, which is used in a skin test for tuberculosis infection. The skin test is also the basis for many allergy testing protocols. Although previous studies have used skin testing of toxoplasmin in mice and hamsters based on swelling and redness, these assays have not proven to be that specific or sensitive (Frenkel J K. 1948. *Dermal hypersensitivity to toxoplasma antigens (toxoplasmins)*. Proc Soc Exp Biol Med 68:634-639.). Previous studies testing toxoplasmin, a skin test reaction elicited by ESA antigens, showed that it was sensitive and specific for detecting individuals in France that were chronically infected with *T. gondii* (Rougier D, Ambroise-Thomas P. 1985. *Detection of toxoplasmic immunity by multipuncture skin test with excretory-secretory antigen*. Lancet 2:121-123.). In those studies, the ES antigen was made from culture supernatants, fixed with formalin, and then dialyzed with a 10 kDa filtration step. In subsequent studies, others have indicated that the active component in toxoplasmin is in the range of 10 kDa to 50 kDa based on filtration (Veprekova. 1978. *Approximative molecular weight of the active component in toxoplasmin*. Folia Parasitol (Praha) 25:273-275.). It should be noted that proteins may undergo proteolytic processing or breakdown, so this size range does not necessarily indicate the size or identity of the full-length protein. Although these studies refined our knowledge of the active components of ESA, the active components remain undefined at the molecular level. Moreover, there is no way to produce the ESA fraction in large quantities such that it could be made into a commercial product.

Delayed type hypersensitivity reactions are predominately driven by CD4+ memory T cells that recognize antigen from a previous exposure (*Mantoux Test as a model for a secondary immune response in humans*. Vukmanovic-Stejic M, Reed J R, Lacy K E, Rustin M H, Akbar A N. Immunol Lett. 2006 10793-101). Upon recognition of their cognate antigen, these memory T cells expand and produce cytokines including interferon gamma (IFN-γ) tumor necrosis factor (TNF) and other chemokines. This initial reaction also results in recruitment of mononuclear (i.e. monocytes) cells and polymorphonuclear (i.e. PMNs) cells from circulation into the tissue. Although the conventional DTH test relies on monitoring induration, and redness that develop at the site of injection, more recent tests have been developed to directly monitor T cells responses to specific antigens. Typically these responses are monitored in circulating T cells obtained from the leukocyte fraction of whole blood. Leukocytes, including antigen-presenting cells and T cells, are mixed in vitro with antigens and the resulting responses monitored by production of IFN-γ or other cytokines. In some applications there are referred to as INFγ-release or IFN-γ-secretion assays, owing the fact that IFN-γ is the primary cytokine thought to drive the DTH response. The advantages of such tests is that they are more quantitative than the traditional skin test, they can be completed with a single office visit, and they often suffer less from cross-reaction to environmental antigens.

The enzyme-linked immunospot or ELISpot assay was originally developed for detecting B cells that were secreting antigen-specific antibodies (*A solid-phase immunoenzymatic technique for the enumeration of specific antibody-secreting cells*. Sedgwick J D, Holt P G. J Immunol Methods. 1983 February 57:301-9). It has seen been modified to detect cytokines secreted by different immune cells. The principle of the assay is that it relies on a sandwich ELISA where a membrane-backed microplate (typically polyvinylidene difluoride) is coated with antibodies to a particular cytokine. Cells from healthy or immune donors are added the plate and incubated overnight in medium under standard culture conditions. Cytokines secreted during this incubation are captured by the antibody-coated membrane. Following the incubation period, the cells are washed off and the captured cytokine is detected by a second antibody that is specific for the protein of interest. Detection is accomplished using an enzyme-linked reagent, either secondary antibody, or streptavidin to detect the biotinylated primary antibody.

ELISpot assays have previously been used for detection of IFN-γ secretion by T cells in patients that were chronically infected with *Toxoplasma gondii* (*Evolving characteristics of toxoplasmosis in patients infected with human immunodeficiency virus-1: clinical course and Toxoplasma gondii-specific immune responses*. Hoffmann C, Ernst M, Meyer P, Wolf E, Rosenkranz T, Plettenberg A, Stoehr A, Horst H A, Marienfeld K, Lange C. Clin Microbiol Infect. 2007 13:510-5). This study focused on immunocompromised patients and used the ELISpot assay as a surrogate for CD4+ T cell responses to whole antigen. Although this study did not evaluate the ELISpot assay as a primary diagnostic tool, it suggests that the degree of immunity in a patient can be inferred from the strength of the response in the ELISpot assay. In this case the ELISpot test was conducted with whole parasite antigen and no attempt was made to define useful antigens that would increase sensitivity or specificity using this assay.

SUMMARY OF THE INVENTION

According to one aspect of the invention, a *Toxoplasma gondii*-derived antigen composition is provided. The composition comprises a *Toxoplasma gondii*-derived antigen selected from the group consisting of: isolated and purified MIC1, MIC3, MIC4, or MIC6; truncated MIC1, MIC3, MIC4, or MIC6; extended MIC1, MIC3, MIC4, or MIC6; a fusion protein comprising any two or more of MIC1, MIC3, MIC4, or MIC6; a fusion protein of any of MIC1, MIC3, MIC4, or MIC6 with a moiety that enhances or facilitates purification, recombinant production, or immune cell stimulation, and combinations thereof as elements of an antigen or components of a composition. The *Toxoplasma gondii*-derived antigen composition may alternatively or additionally comprise or consist of any of the antigens shown in Table 1.

According to another aspect of the invention, a kit is provided. The kit comprises (a) a *Toxoplasma gondii*-derived antigen composition and (b) an applicator device for administration of the *Toxoplasma gondii*-derived antigen to a subject. The composition comprises a *Toxoplasma gondii*-derived antigen selected from the group consisting of: isolated and purified MIC1, MIC3, MIC4, or MIC6; truncated MIC1, MIC3, MIC4, or MIC6; extended MIC1, MIC3, MIC4, or MIC6; a fusion protein comprising any two or more of MIC1, MIC3, MIC4, or MIC6; a fusion protein of any of MIC1, MIC3, MIC4, or MIC6 with a moiety that enhances or facilitates purification, recombinant production, or immune cell stimulation, and combinations thereof as elements of an antigen or components of a composition. The *Toxoplasma gondii*-derived antigen composition may comprise or consist of any of the antigens shown in Table 1.

According to yet another aspect of the invention a method of delivering *Toxoplasma gondii*-derived antigen to a subject is provided. An applicator device that is loaded with a *Toxoplasma gondii*-derived antigen composition is contacted with skin of the subject. The *Toxoplasma gondii*-derived antigen composition is thereby delivered to the skin of the subject. The composition comprises a *Toxoplasma gondii*-derived antigen selected from the group consisting of: isolated and purified MIC1, MIC3, MIC4, or MIC6; truncated MIC1, MIC3, MIC4, or MIC6; extended MIC1, MIC3, MIC4, or MIC6; a fusion protein comprising any two or more of MIC1, MIC3, MIC4, or MIC6; a fusion protein of any of MIC1, MIC3, MIC4, or MIC6 with a moiety that enhances or facilitates purification, recombinant production, or immune cell stimulation, and combinations thereof as elements of an antigen or components of a composition. The *Toxoplasma gondii*-derived antigen composition may comprise or consist of any of the antigens shown in Table 1.

Yet another aspect of the invention is an applicator device for administering one or more *Toxoplasma gondii*-derived antigens to a mammal. The applicator device comprises one or more *Toxoplasma gondii*-derived antigens. The *Toxoplasma gondii*-derived antigens are selected from the group consisting of: isolated and purified MIC1, MIC3, MIC4, or MIC6; truncated MIC1, MIC3, MIC4, or MIC6; extended MIC1, MIC3, MIC4, or MIC6; a fusion protein comprising any two or more of MIC1, MIC3, MIC4, or MIC6; a fusion protein of any of MIC1, MIC3, MIC4, or MIC6 with a moiety that enhances or facilitates purification, recombinant production, or immune cell stimulation, and combinations thereof as elements of an antigen or components of a composition. The *Toxoplasma gondii*-derived antigen composition may comprise or consist of any of the antigens shown in Table 1.

Yet another aspect of the invention is a method of eliciting and/or monitoring a T cell response in a subject. A *Toxoplasma gondii*-derived antigen composition is contacted with T cells of the subject. The *Toxoplasma gondii*-derived antigen composition induces a T cell response, which may involve production or secretion of cytokines. The *Toxoplasma gondii*-derived antigen composition may be isolated and purified MIC1, MIC3, MIC4, or MIC6; truncated MIC1, MIC3, MIC4, or MIC6; extended MIC1, MIC3, MIC4, or MIC6; a fusion protein comprising any two or more of MIC1, MIC3, MIC4, or MIC6; a fusion protein of any of MIC1, MIC3, MIC4, or MIC6 with a moiety that enhances or facilitates purification, recombinant production, or immune cell stimulation, and combinations thereof as elements of an antigen or components of a composition. The *Toxoplasma gondii*-derived antigen composition may comprise or consist of any of the antigens shown in Table 1.

These and other embodiments which will be apparent to those of skill in the art upon reading the specification provide the art with

BRIEF DESCRIPTION OF THE DRAWINGS

The patent or application file contains at least one drawing executed in color. Copies of this patent or patent application with color drawing(s) will be provided by the Office by request and payment of the necessary fee.

FIG. 3 shows luminol responses in mice.

DETAILED DESCRIPTION OF THE INVENTION

Figure 1:
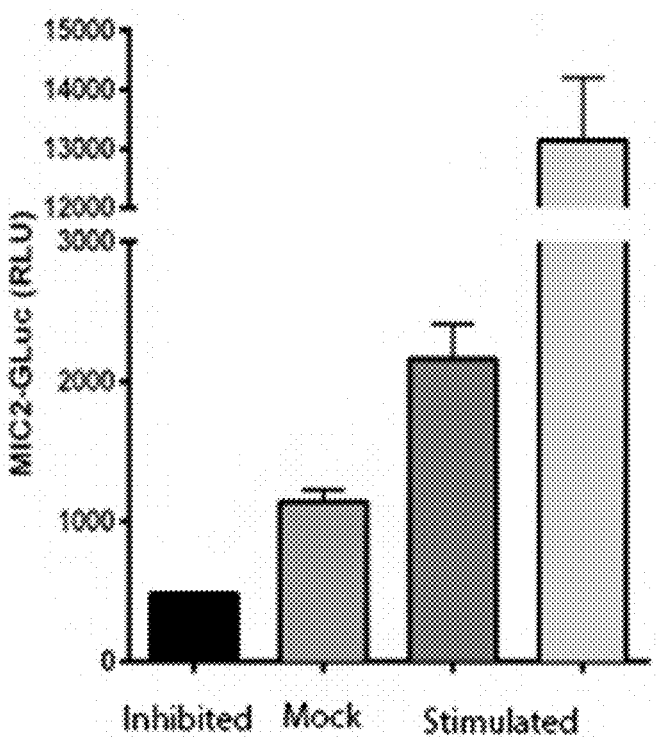
FIG. 1 shows a luciferase-based secretion assay. Secretion was monitored by release of the reporter protein MIC1-GLuc into the supernatant. Samples include cells that were treated with BAPTA-AM to block secretion (Inhibitor), cells treated only with buffer (Mock), and cells treated with BSA and zaparinast (Stimulated). These later samples contain the fraction that is referred to as ESA.

The inventors have developed a standardized, abundant test antigen composition for use in sensitively and specifically testing individuals for infection by *Toxoplasma gondii*. Antigens that cause a non-specific reaction (whether the subject has been infected or not) and antigens that cause a specific reaction (only in subject that has been infected) have been identified. The latter have been purified and cloned and modified to form test reagents. The former have been eliminated from test reagents.

The compositions of antigens preferably contain only antigens that cause a specific reaction and are devoid of antigens that cause a non-specific reaction. Such preparation may be made by any means known in the art, including isolation and purification from, e.g., natural sources, recombinant production, or synthetic production. Carriers for the antigens may be any standardly used, typically a carrier that does not itself cause a DTH reaction or inhibit a DTH reaction by a bona fide antigen. Non-limiting examples of excipients that may be used for the antigen compositions are sucrose, mannitol, trehalose, and Hemaccel™ (intravenous colloid). Buffers, salts, sugars, preservatives, isotonic saline solutions, phosphate-buffered saline, can also be used in the compositions. Additional components and excipients include water, polymers, fatty acid esters, parabens. Compositions may be stored as convenient, including without limitation as lyophilized samples, at about or below 4 degrees C., and at about or below −70 degrees C.

Compositions of antigens may be free of other ESA components such as dense granular proteins (GRA), other microneme proteins, or other components which lead to lower sensitivity and/or specificity. An isolated and purified preparation may be from *T. gondii* organisms, from a recombinant host cell, or from a synthetic in vitro reaction. The isolated and purified protein may comprise at least at least 1%, at least 5%, 10%, at least 20%, at least 25%, at least 30%, at least 40%, at least 50%, at least 60%, at least 70%, at least 75%, at least 80%, at least 85%, at least 90%, at least 95%, at least 97%, or at least 99% of the protein in a composition.

Testing for DTH may be used in order to prevent or detect congenital toxoplasmosis, for example by testing women before or during pregnancy, respectively. Primary infection of pregnant women may lead to abortion or severe neonatal malformation. Testing may also be used in immunocompromised patients, in whom a severe form of the disease may be fatal. Testing for DTH might also be performed in healthy adults to determine their infectious status prior to performing a medical procedure as a consequence of which they may become immunocompromised. Detection of infection may be critical in managing the disease. If a positive DTH test occurs, it may be desirable to follow it with a serum test. Because the two types of tests detect different immunological pathways and components, the two types of tests may give complementary information. Serum tests detect antibodies, whereas DTH tests detect cellular immune responses.

As an alternative, an in vitro reaction may be used to detect a T cell response. The in vitro reaction may be performed on any source of T cells, including whole blood, serum, plasma, and other tissue sources of T cells. The T cells are contacted with one or more of the *Toxoplasma gondii*-derived antigens or an antigen composition. If the T cells are reactive with the antigens or antigen composition they release a cytokine such as interferon-γ or other cytokines. The presence of interferon-γ or other released cytokine can be detected using any technique known in the art, including but not limited to an antibody or a series of antibodies. The antibodies may be labeled for detection. An antibody may be attached to an enzyme, such as horseradish peroxidase or alkaline phosphatase that produces colored products in the presence of appropriate substrates. An antibody may be fluorescently labeled, as an alternative. The in vitro reaction product may be captured on a solid support or assayed in the reaction fluid.

Kits may comprise an outer package to contain all components as well as optional inner packaging to contain individual components or combinations of components. Optional components include instructions for assembly and/or administration, information on side effects, expiry information, etc. Information may be provided in paper form, on a digital medium, or as an internet address to such information.

Applicators may be any type as is known in the art for administering an antigen to the skin of a subject and developing a DTH response. These include without limitation patches, needles, multi-needle assemblies, prongs, multi-prong assemblies. Antigens may be administered individually at separate locations or in combination at a single location.

Fusion proteins can be made using recombinant DNA technology to express two or more proteins or polypeptide portions of proteins as a single expression product. Any suitable technique known in the art for making and expressing such fusion proteins may be used. In some embodiments, a non-*T. gondii* protein is fused to a *T. gondii* protein. In other embodiments, two distinct *T. gondii* proteins are fused together.

Amounts of antigen composition that may be administered can be empirically determined, but may be between 0.1 and 50 ug, between 0.5 and 25 ug, or between 1 and 10 ug.

Suitable subjects include, but are not limited to, a human, a livestock animal, a companion animal, a lab animal, and a zoological animal. A subject may or may not be known to have a TDP43-mediated disorder. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a preferred embodiment, the animal is a laboratory animal. Non-limiting examples of a laboratory animal may include rodents, canines, felines, and non-human primates. In another preferred embodiment, the subject is a human.

MIC1 is normally a 456 residue (amino acid) protein that is processed in the parasite remove the N-terminal 16 residues. This leaves a total size of 440 residues. In contrast to this native protein, the form we have expressed, termed here truncated MIC1, is from residues 20-340, for a total size of 320 amino acids. This region of the protein contains a micronemal adhesive repeat that has been shown to bind to host sialic acid residues [Garnett, J. A., et al., *Detailed insights from microarray and crystallographic studies into carbohydrate recognition by microneme protein 1 (MIC1) of Toxoplasma gondii*. Protein Sci, 2009. 18(9): p. 1935-47.]. We expressed a truncated version of the protein in order to make it soluble, a property that would distinguish it from the native molecule that also contains a C-terminal galectin domain [Saouros, S., et al., *A novel galectin-like domain from Toxoplasma gondii micronemal protein 1 assists the folding, assembly, and transport of a cell adhesion complex.* J Biol Chem, 2005. 280(46): p. 38583-91.]. It may, as a result, be recognized differently by the immune system.

MIC3 is normally a 383 residue (amino acids) protein that is processed in the parasite to remove the N-terminal 26 residues. This leaves a mature protein of 357 residues. We expressed a truncated form of MIC3 from residues 134 to 383, for a total size of 250 residues. We expressed a truncated version of the protein in order to make it soluble, a property that distinguishes it from the native molecule. The truncated form of MIC3 lacks most of the N-terminal lectin domain (residues 67-145) but contains the EGF repeats (residues 145-359) described previously (*The Toxoplasma gondii protein MIC3 requires pro peptide cleavage and dimerization to function as adhesin*. Cérède O, Dubremetz J F, Bout D, Lebrun M. EMBO J. 2002 21:2526-36).

MIC4 is normally a 580 residue (amino acid) protein that is processed in the parasite to remove the N-terminal 25 amino acids. This leaves a mature protein of 555 amino acids. Biochemical studies have shown that the full length protein is further processed at the N-terminus between residues 57-58 (VT-SS) and by a C-terminal processing event to generate a 50 kDa and a 15 kDa products (*The toxoplasma micronemal protein MIC4 is an adhesin composed of six conserved apple domains*. Brecht S, Carruthers V B, Ferguson D J, Giddings O K, Wang G, Jakle U, Harper J M, Sibley L D, Soldati D. J Biol Chem. 2001 276:4119-27). We expressed a truncated form of MIC4 from residues 58 to 231, for a total size of 173 residues, a property that distinguishes it from the native molecule. The region of the protein that we expressed contains the first two Apple domains, but lacks the C-terminal Apple domains 5,6 that mediate binding to host cells (*The toxoplasma micronemal protein MIC4 is an adhesin composed of six conserved apple domains*. Brecht S, Carruthers V B, Ferguson D J, Giddings O K, Wang G, Jakle U, Harper J M, Sibley L D, Soldati D. J Biol Chem. 2001 276:4119-27).

MIC6 is a 349 residue (amino acid) protein that is processed in the parasite to remove the first 23 residues. This leaves a mature protein of 326 residues that was expressed as a recombinant protein in *E. coli*. This full-length form of the protein contains three EGF domains, a single acidic domain and a transmembrane domain near the C-terminus as described previously (*Structural insights into microneme protein assembly reveal a new mode of EGF domain recognition*. Sawmynaden K, Saouros S, Friedrich N, Marchant J, Simpson P, Bleijlevens B, Blackman M J, Soldati-Favre D, Matthews S. EMBO Rep. 2008 9:1149-55).

The mixture of ESA proteins, previously referred to as useful for a human skin test [Rougier, D. and P. Ambroise-Thomas, *Detection of toxoplasmic immunity by multipuncture skin test with excretory-secretory antigen*. Lancet, 1985. 2(8447): p. 121-3] may contain proteins that elicit non-specific responses. By removing these contaminants and focusing on proteins that only give positive responses in infected animals (and individuals) including MIC1, MIC3, MIC4, and MIC6, and truncated and/or fused forms of these proteins, our test achieves properties that are superior to the natural mixture of ESA proteins.

Previous studies have identified short peptide residues that enhance uptake by dendritic cells and increase the efficiency of antigen presentation [Sioud, M., et al., *A novel peptide carrier for efficient targeting of antigens and nucleic acids to dendritic cells*. FASEB J, 2013. 27(8): p. 3272-83.]. The receptor to which these peptides bind on host dendritic cells is not known. Nonetheless, it is likely that these short sequences work by enhancing uptake of the antigen and priming the presentation pathway. These steps of antigen uptake, processing, and presentation are critical for the DTH response. MIC1, MIC3, MIC4, and MIC6 and truncated and/or fused forms of these proteins, can be expressed so that these sequences are either at the N- or C-termini. These modified antigens can be purified under conditions that minimize contamination with LPS. Levels of LPS may be reduced to less than 0.5 EU/ml, less than 0.25 EU/ml, less than 0.1 EU/ml, less than 0.05 EU/ml. Any modification described herein for MIC1, 3, 4, or 6 can also be applied to any of the proteins of Table 1 or Table 2.

The above disclosure generally describes the present invention. All references disclosed herein are expressly incorporated by reference. A more complete understanding can be obtained by reference to the following specific examples that are provided herein for purposes of illustration only, and are not intended to limit the scope of the invention.

EXAMPLES

Example 1

Stimulation of Microneme Secretion

Freshly isolated tachyzoites of *Toxoplasma gondii* were stimulated to secrete Excretory-Secretory Antigens (ESA) using procedures similar to those published previously [1]. In brief, high-binding 96-well plates were coated with 1% bovine serum albumin (BSA) in phosphate buffered saline (PBS) pH 7.4 or PBS alone at 4° C. overnight. The next day, plates were washed with PBS to remove soluble BSA just prior to the secretion assay. Freshly harvested type I strain RH-parasites were purified and resuspended in intracellular buffer (25 mM HEPES pH 7.4, 142 mM KCl, 5 mM NaCl, 1 mM $MgCl_2$, 2 mM EGTA, 5.6 mM D-Glucose). Control parasites were treated with 50 μM BAPTA-AM to suppress secretion and added to wells washed with PBS (no BSA coating). For stimulated samples, untreated parasites were added to BSA-coated wells in the presence of 500 μM zaprinast. Parasites were allowed to secrete for 10 min at 37° C. prior to collection of the supernatant. Duplicate samples for each treatment were processed for liquid chromatography and tandem mass spectrometry (LC/MS-MS).

Identification of *Toxoplasma*-Secreted Proteins in ESA by LC-MS/MS

Secreted proteins were detected by LC-MS/MS as previously described [1]. In brief, ESA samples were reduced with 10 mM Tris-(2-carboxyethyl)phosphine and alkylated with 20 mM iodoacetamide before digestion overnight with 0.5 μg of trypsin. After desalting, the digest was then dried down and resuspended in 15 μl of 5% acetonitrile, 0.1% formic acid. Five microliters was resolved by LC-MS/MS on a NanoLC Ultra (Eksigent Technologies) coupled with an LTQ-Velos Pro Orbitrap (Thermo Scientific) using a 2 hr gradient. Raw data were processed and compared to the predicted proteome of the *T. gondii* genome to identify the protein components of ESA, as described previously [2]. For comparative semi-quantitative analysis, fold-enrichment was calculated from the frequency of spectral counts for peptides in the BSA-zaprinast stimulated samples compared to the BAPTA-AM treated control (set at 1 where no peptides were detected) for each protein detected in ESA. Proteins were considered candidate ESA proteins if the average fold enrichment was ≥4 in both of two independent experiments. Additionally, the cell-cycle specific expression profile for each candidate gene was analyzed to determine if it matched the profile of known microneme protein encoding genes [3]. Only proteins that fit both criteria (4 fold enriched and microneme transcriptional profile) were considered authentic ESA-enriched proteins.

Cloning and Expression of *T. gondii* Antigens

Gene sequences encoding *T. gondii* microneme (MIC) and dense granule (GRA) proteins were obtained from ToxoDB (Protocol: http; Domain: toxodb; Top level domain: org). The coding regions were analyzed for the presence of predicted transmembrane or signal peptides using the ExPASy server (Protocol: https; subdomain: www; second level domain: expasy; Top level domain: org). Proteins were expressed either as full-length proteins or as truncations that were designed to eliminate undesirable hydrophobic regions. Genes were cloned from cDNA produced by Superscript III (Thermo Fischer Scientific) reverse transcriptase priming from polyA mRNA isolated from the type II ME49 strain, according to the manufacturer's recommendations. Primers to the coding regions of interest were designed to contain a BsaI site at the 5 end, and a XbaI site at the 3 end, in order to be compatible with the N-terminal His-tagged SUMO system from LifeSensor (pE-SUMO vector). PCR amplicons containing the region of interest were digested with BsaI and XbaI and cloned into similarly prepared pE-SUMO vector and transformed into competent XL1-Blue *E. coli*. Ampicillin resistant transformants were checked by PCR amplification and Sanger sequencing to verify plasmid inserts. To express recombinant proteins, pE-SUMO vectors containing inserts of *T. gondii* genes were transformed into BL21(DE3) Rosetta pLysS *E. coli* cells grown in terrific broth (TB) or Luria broth (LB). For induction of protein expression, cells were grown as a 5 ml overnight culture, then diluted 1:1,000 in fresh LB or TB and cultured at 37° C. for 4-6 hr followed by addition of IPTG (0.5-1.0 mM) and culture at 15° C. overnight. Protein expression and solubility were tested by lysis of the cell pellet in CelLytic B buffer (Sigma-Aldrich) and separation of pellet and supernatant fractions that were analyzed by SDA PAGE.

Proteins were purified using His-select nickel affinity columns (Sigma-Aldrich), and eluted in 200-300 mM imidazole, 50 mM sodium phosphate pH 8.0, 300 mM NaCl, according to the manufacturer's instructions. In cases where the SUMO tag was removed, proteins were first bound to nickel beads and then treated with purified SUMO protease U1P1 that was cloned as a N-terminal fusion in pET22b (Novagen) and separately produced in *E. coli*. The His-tagged SUMO and His-tagged protease were bound to the His-select nickel beads and the eluted fraction was analyzed for enrichment of the cleaved recombinant *T. gondii* protein. Proteins were checked for purity and concentration by SDS PAGE stained with Coomassie Blue or Syrpo Ruby. Proteins were dialyzed against 150 mM NaCl, 50 mM Tris-HCl, pH 8.0 and stored in aliquots at a concentration of 0.3 μg/μl at −80° C. until used.

The purified recombinant proteins elicited strong responses in the Limulus amebocyte assay (LAL), the gold standard for monitoring lipopolysaccharide (LPS). To alleviate this problem, we treated the recombinant proteins with polymyxin B resin, an antibiotic that binds LPS (*Endotoxin removal from protein solutions*. Petsch D, Anspach F B. J Biotechnol. 2000 Jan. 21; 76(2-3):97-119). Recombinant proteins were incubated with Polymyxin B agarose-endotoxin removal resin (Sigma, USA) for 6-12 hrs at 4° C. using gentle end over end mixing to achieve an endotoxin level <0.1 EU/mg. Then, the proteins were eluted using endotoxin-free buffer containing Tris-HCl at pH 6-8 depending on the protein. The amount of residual LPS in the proteins preparation were checked using a LAL assay kit (Pierce, USA) according to the manufacturer's instructions. Purified endotoxin-free proteins were then filter sterilized, quantified and stored at −80° C.

Chronic Mouse Infections

Specific-pathogen-free mice were obtained from Jackson Laboratories and housed in the Animal Care Facilities at Washington University School of Medicine. Animals were housed and cared for according to the NIH Guide for the Care and Use of Laboratory Animals as approved by the Animal Studies Committee at Washington University.

Female C57/BL6 or Balb/C mice, age 8-12 weeks, were infected with the type II strains PRU or ME49 by i.p. needle inoculation of tachyzoites grown in vitro, using procedures described previously [4]. Alternatively, naïve animals were infected by oral feeding of 5-10 tissue cysts from chronically infected mice, as described previously [4]. To prevent accidental death during acute infection, mice infected with the ME49 strain were given sulfadiazine in the drinking water (0.1-0.2 g/L) 4-10 days post infection. Chronic infections were confirmed by serological analysis of serum obtained 30 days post infection, as described previously [4].

In Vitro Assays for IFN-γ Secretion

To obtain T lymphocytes for ELISpot analysis, we isolated splenocytes from naïve and $T.$ $gondii$ chronically infected mice. Spleens were harvested and splenocytes were isolated by passage through a 70-μm-pore-size nylon cell strainer. Splenocytes were pelleted and red blood cells (RBCs) were removed using RBC lysis buffer (Biolegend, USA) for 5 min at 4° C. Splenocytes were then washed in sterile PBS and HBSS media (Corning, USA). Splenocytes were finally resuspended in CTL-media (CTL, USA) supplemented with 1% L-glutamine and 1× Pen-strep antibiotics.

ELISpot assays were conducting in 96 well plate format using splenocytes isolated as described above. Briefly, 2.5× $10^5$ cells per well were plated in 96-well plate pre-coated with murine IFN-γ capture antibody (Immunospot, CTL, USA) and cultured for 24 hrs with media alone, purified recombinant proteins (2 μg/ml), a recall positive control-ESA (2 μg/ml), a T cell non-specific positive control Con A (2 μg/ml) and purified recombinant control protein-SUMO (2 μg/ml) at 37° C. with 5% $CO_2$. After washing and developing the plate according to the manufacturer's instructions, the antigen recall response was determined by counting the number of spots (IFN-γ producing cells) per well per treatment. The number of IFN-γ producing T-cells following stimulation with $T.$ $gondii$ antigens, were detected and calculated using an ELISpot reader (Immunospot®S6 Core, CTL, USA).

Antigen Injection and Monitoring of Luminol Reaction

Control or chronically $T.$ $gondii$ infected mice were used to test the delayed type hypersensitivity (DTH) response using a previously published protocol for monitoring luminol fluorescence after in vivo injection [5]. Control or chronically infected mice were injected with PBS, ESA proteins (1.5 ug/in 10 μL injection volume). Animals were injected s.c. either in the pinne of the ear (using PBS control on one side and antigen on the other) or s.c. in the back of the animal after it had been shaved to remove fur. At 24, 48, or 72 hr post injection, mice were anesthetized using isoflurane, injected i.p. with luminol (10 μL/gram of body weight of a 20 mg/ml stock) and imaged using an IVSI Spectrum in vivo Imaging System with exposure settings of 1-3 sec. Data were analyzed using the IVIS Living Image software to determine the relative light emission for the region where antigen was injected, compared to a neutral background region or to the PBS control injection. Data were graphed and analyzed using Prism (GraphPad).

MIC1 Predicted protein sequence Type II ME49:

(SEQ ID NO: 1)
MGQALFLTVLLPVLFGVGPEAYGEASHSHSPASGRYIQQMLDQRCQEIAA

ELCQGGLRKMCVPSSRIVARNAVGITHQNTLEWRCFDTASLLESNQENNG

VNCVDDCGHTIPCPGGVHRQNSNHATRHEILSKLVEEGVQRFCSPYQASA

NKYCNDKFPGTIARRSKGFGNNVEVAWRCYEKASLLYSVYAECASNCGTT

WYCPGGRRGTSTELDKRHYTEEEGIRQAIGSVDSPCSEVEVCLPKDENPP

VCLDESGQISRTGGGPPSQPPEMQQPADRSDERGGGKEQSPGGEAQPDHP

TKGGNIDLPEKSTSPEKTPKTEIHGDSTKATLEEGQQLTLTFISTKLDVA

VGSCHSLVANFLDGFLKFQTGSNSAFDVVEVEEPAGPAVLTIGLGHKGRL

AVVLDYTRLNAALGSAAYVV EDSGCSSSEEVSFQGVGSGATLVVTTLGE

SPTAVSA

The form of MIC1 used in the assay (in bold above):

(SEQ ID NO: 2)
His-SUMO-(M)AYGEASHSHSPASGRYIQQMLDQRCQEIAAELCQGGLR

KMCVPSSRIVARNAVGITHQNTLEWRCFDTASLLESNQENNGVNCVDDCG

HTIPCPGGVHRQNSNHATRHEILSKLVEEGVQRFCSPYQASANKYCNDKF

PGTIARRSKGFGNNVEVAWRCYEKASLLYSVYAECASNCGTTWYCPGGRR

GTSTELDKRHYTEEEGIRQAIGSVDSPCSEVEVCLPKDENPPVCLDESGQ

ISRTGGGPPSQPPEMQQPADRSDERGGGKEQSPGGEAQPDHPTKGGNIDL

PEKSTSPEKTPKTEIHGDSTKATLEEGQQLTL

MIC1 Coding sequence (introns spliced out, coding region in bold) Type II ME49:

(SEQ ID NO: 3)
acctgaaagcgggtgccgcgtcgctaccgtttcctgtggcgtctctagtg cgacatccgaagtaacagtaacgtccggcatggaacgccgacgcgggtgt tccagtcgcctggctccttctactcgcacttcgatgttacgttccttatt ggtgcgacgcggttctcgtgttgctagacgtcgcaccggctgaaagctgt agaaaatttagttattttcctgtcagctagcttgcaggagtgcgttttttg tgtgttggtttcgtctcacatggctgctgatctgttgatgcagctgtgta cacgtgcctcgattctgtagttgacctagaaacggatttgcaaagATGGGC

CAGGCGTTGTTTCTCACCGTTCTATTGCCGGTGTTATTTGGCGTTGGGCC

AGAAGCATATGGAGAAGCGTCGCATTCTCATTCGCCGGCATCGGGACGTT

ATATACAACAGATGCTTGACCAACGCTGCCAAGAGATTGCTGCAGAACTC

TGCCAAGGCGGACTTCGTAAAATGTGTGTGCCCTCTAGCCGGATAGTAGC

TCGAAACGCCGTGGGCATTACTCATCAAAATACACTTGAATGGAGATGCT

TTGATACAGCCTCTTTGCTGGAGAGCAATCAAGAAAACAACGGTGTTAAT

TGCGTGGACGACTGTGGCCACACGATACCGTGTCCTGGCGGCGTACACCG

GCAAAACAGTAATCACGCAACGCGCCATGAGATACTGTCCAAATTGGTCG

AAGAAGGAGTACAACGGTTCTGCAGTCCTTATCAAGCATCTGCCAACAAG

-continued

```
TACTGTAACGACAAATTTCCAGGGACCATTGCGAGGAGGTCGAAGGGCTT

CGGAAACAATGTCGAGGTTGCGTGGAGGTGTTACGAGAAGGCCAGCTTGC

TGTACTCGGTTTATGCTGAGTGTGCGAGCAACTGCGGAACAACGTGGTAC

TGCCCTGGAGGACGACGAGGGACGTCGACAGAACTAGACAAGCGGCATTA

TACAGAAGAGGAAGGAATTCGCCAGGCAATCGGATCCGTCGACAGCCCAT

GTTCTGAAGTTGAAGTCTGCCTACCGAAGGATGAGAATCCCCCGGTGTGT

TTAGATGAAAGTGGCCAGATTTCACGAACTGGTGGTGGGCCACCGTCACA

ACCGCCTGAGATGCAACAGCCCGCCGATCGTTCGGACGAGAGAGGTGGCG

GTAAGGAACAGTCGCCTGGAGGAGAAGCTCAGCCGGACCATCCAACGAAG

GGTGGTAACATAGACCTGCCTGAGAAATCAACATCTCCCGAGAAGACGCC

GAAAACCGAGATCCATGGTGACAGCACGAAAGCGACGCTCGAAGAGGGGC

AGCAACTAACGCTCACGTTTATCTCCACTAAACTGGATGTTGCTGTAGGC

TCGTGTCATTCACTCGTCGCGAATTTCCTTGATGGATTTTTGAAGTTTCA

GACGGGCTCAAATTCGGCGTTCGATGTGGTAGAAGTGGAAGAGCCAGCAG

GACCCGCAGTGCTTACGATAGGTCTGGGACACAAAGGCCGTCTCGCTGTT

GTCCTCGACTACACCAGGCTCAATGCTGCTTTAGGATCAGCTGCTTACGT

GGTCGAAGATTCTGGATGCAGCTCAAGTGAAGAGGTTAGTTTCCAAGGAG

TGGGTAGTGGAGCGACGCTCGTGGTGACGACGCTTGGCGAGAGTCCTACG

GCCGTCTCTGCTTGAtttatagtactctttggagcatgcttgtggaggaa cgggacaatctcggcaaaatcaggatgaagtttgtgagatacagatcgtt cctgaacagtggaagatgcgtcactattacacctatatgcgtcctggttc ttgtagagttggagttcttgcaggtgtaatgactatgacatacggatata acttcatacggggaactgtg
```

Primers used for cloning

```
MIC1(20-340) Bsa1-F:
                                      (SEQ ID NO: 4)
ACTGTGGTCTCTAGGTATGGAAGCATATGGAGAAGCGTCGCATTCTCA

MIC2(20-340) XBA1-R:
                                      (SEQ ID NO: 5)
ACTGTTCTAGATCAGAGCGTTAGTTGCTGCCCCTCTTCGAGCGTCGCTT
```

MIC3 Predicted protein sequence type II ME49:

```
                                      (SEQ ID NO: 50)
MRGGTSALLHALTFSGAVWMCTPAEALPIQKSVQLGSFDKVVPSREVVSE

SLAPSFAVTETHSSVQSPSKQETQLCAISSEGKPCRNRQLHTDNGYFIGA

SCPKSACCSKTMCGPGGCGEFCSSNWIFCSSSLIYHPDKSYGGDCSCEKQ

GHRCDKNAECVENLDAGGGVHCKCKDGFVGTGLTCSEDPCSKRGNAKCGP

NGTCIVVDSVSYTCTCGDGETLVNLPEGGQGCKRTGCHAFRENCSPGRCI

DDASHENGYTCECPTGYSREVTSKAEESCVEGVEVTLAEKCEKEFGISAS

SCKCDNGYSGSASATSHHGKGESGSEGSLSEKMNIVFKCPSGYHPRYHAH

TVTCEKIKHFALDGAGNHDTTTYVARRRYPASL
```

The form of MIC3 used in the assay (in bold above):

```
HisSUMO-
                                      (SEQ ID NO: 51)
YHPDKSYGGDCSCEKQGHRCDKNAECVENLDAGGGVHCKCKDGFVGTGLT

CSEDPCSKRGNAKCGPNGTCIVVDSVSYTCTCGDGETLVNLPEGGQGCKR

TGCHAFRENCSPGRCIDDASHENGYTCECPTGYSREVTSKAEESCVEGVE

VTLAEKCEKEFGISASSCKCDNGYSGSASATSHHGKGESGSEGSLSEKMN

IVFKCPSGYHPRYHAHTVTCEKIKHFALDGAGNHDTTTYVARRRYPASL
```

Coding sequence (introns spliced out, coding region bold)
Type II ME49:

```
                                      (SEQ ID NO: 52)
tcttctcttcttccgtacttttccctgcatttcacacccctggtatgact ccacaccgcgtgtaaatgtcccttaggtgacacccgcagcagcgcgtagg aggaagtagatgtcagtgtagacgttttgagatgagagacgataacgta aaatgccgccgataacttctgcattatacacactctctctccacgcctag gatgacaggtacggcggcacacggaggaaagtggggggggggggggggc gaacagaaaggtcacatggaaggccgctcgactctccactcacgaagtga aggcttcgtcccgttttgctggacaacgaatgcgaacttcttcactcgct tgtgacacacacaactccagaggcacagagatgtgaagcagaagagtggc gtgtgcgtcgcttctgtcggcggcaagcccgctccgtctctttggtggc gattctggtgtgcaccgtgtgccaagaagttgcgtgtcacgcgacttttg gaaatgcatcaggttcagagtcgttatgttgcgattcaggctctcggcag agaatcatttccctgtaagctagttgaactcgccttttttaaaagcggcag cagtgcccttgtggaaggcctcactgtgcctactttcctcgtcctgagtt tttccgccttcggcctcatttttgctcaccaaaatcgtgtcctaccgtc aagttttgccatagactcctacgggaaaaaacaagccggtcgacacggac gacgcccgcagggaagcgtcccctccgcagaaatcgggagacaactgtcg ttgacggtgctgcgcgaaaggtcacagagtttccagtgtgttcatcagac ctcactgtgcactgttagcggccgctgtcccgcctggtcaacaagtatca caccctcgtccccgccattggcacggagctcgatgagctgcagtgtcgct tttaggggagtcgtgcaatcacgccgcaacacaggcgtgattcgatcttc aattgctaggtaaccactcgtgcttggtagctctgcaatggctcgagcga cggggggtgatgcaacatgctgctaaaaactcgacagacgtgtcaccggaa cccacctaaataggagaccacgggtctctggtgtgtcgcgtcgcattctc gcgtcgcattctcgcgtcgcaatgaccggccagttgctcgacgtcgccag ccgggactgaagagcgttcatcgagtcagcagcattgcgtcccttgctc ggtgaaaaaagactctctggtcgagtctagctcgtgtcacttctgtttct aacctccttcgttcaccggtacacctccgatgtgacttttggtacacttg ccctgtcgcacgacgcacgctgtcactcaacttgctgctagcgcaatcga taggttccctcgaaccagccatcacacacacacccttttccgggaagacgt ttgcgggcggtgggtcgcagctcgtcgagagtgcgtttctgtgcatttct gtgggcagtgcagcgcgtttgcgcgcgccttactctgtgtgtaacttccttg
``` tccaacactggtaaaaATGCGAGGCGGGACGTCCGCGCTGTTGCACGCGC

TCACCTTCAGTGGGGCCGTGTGGATGTGCACCCCAGCGGAGGCTTTGCCG

ATTCAGAAGTCTGTGCAGCTGGGCAGCTTTGACAAAGTTGTGCCGAGCCG

CGAAGTCGTCTCTGAGAGTCTTGCTCCGTCTTTCGCGGTGACTGAGACTC

ACTCGTCTGTGCAATCCCCCAGCAAGCAGGAGACGCAACTCTGTGCTATC

TCGAGTGAAGGCAAGCCATGTCGAAACCGTCAGTTGCACACTGACAACGG

GTACTTCATCGGGGCCAGTTGCCCCAAGAGCGCTTGCTGCAGCAAGACCA

TGTGCGGCCCCGGCGGCTGCGGAGAATTCTGCTCCAGCAACTGGATTTTT

TGCAGCAGTTCGCTCATCTACCATCCTGACAAAAGCTATGGAGGAGACTG

CAGCTGTGAAAAGCAGGGCCATCGGTGCGACAAAAACGCAGAATGCGTCG

AAAACTTGGACGCGGGTGGGGGTGTGCACTGCAAGTGCAAAGACGGCTTC

GTCGGCACTGGGTTGACTTGCTCCGAGGATCCTTGTTCAAAAAGAGGGAA

CGCGAAGTGCGGACCCAACGGGACGTGCATCGTCGTCGATTCAGTCAGCT

ACACATGCACCTGCGGCGACGGCGAAACTCTAGTGAACCTCCCGGAAGGG

GGACAAGGATGCAAGAGGACTGGATGTCATGCCTTCAGGGAGAACTGCAG

CCCTGGTAGATGTATTGATGACGCCTCGCATGAGAATGGCTACACCTGCG

AGTGCCCCACAGGGTACTCACGTGAGGTGACTTCCAAGGCGGAGGAGTCG

TGTGTGGAAGGAGTCGAAGTCACGCTGGCTGAGAAATGCGAGAAGGAATT

CGGCATCAGCGCGTCATCCTGCAAATGCGATAACGGATACTCCGGATCTG

CTTCCGCAACCTCCCACCATGGGAAAGGAGAATCGGGATCCGAGGGGAGC

TTGAGTGAAAAAATGAATATTGTCTTCAAGTGCCCCAGTGGCTACCATCC

AAGATACCATGCCCACACCGTGACGTGTGAGAAAATTAAGCACTTTGCCC

TTGACGGGGCCGGCAACCACGACACGACTACGTATGTCGCAAGACGAAGG

TACCCAGCGAGTCTCTGAgagcggagatcagcgcaaagacaagatgcaga gtttgactcgagaaacaatagtaacacgaagtaaaaagtctccacactaa gccaaggattgagaatatttcgatttgtgccgctggcaatagtggccttg gcctagaaagaagttctgcaacgaagcgatcggctcacacgcggatacac agatgggtttgtaccgagaacgttaggtttgtgaaccgagttcaggtaaa acaaagtagattgtgcctttacgcagacagcgagggaaaacatgaggaca cactgccaactaaagcaagactgcctcactaattaccaccgacacacgac atggttaccccgcgttttgccgcgtgcaaagtttgaattctgatggttc tcgagtctgaaagcctaaaccgcccaaccatgtatgaaataagaacccat caaacgtgagacatctctgccgaagtgcctacgaaaagaacgcttctgcc actaggaggtgcggcctcttcattctatgagaacctgctttgtcggtgtc aacctctggggaaatcgcctgcctttacacattttgctcgttgtagagca agggatctgttgctgcgtttactccaatacaatgatcgccgtttcgctgt aggcaagcgatccgaaaatgtacgttcgagtcagcagctacttgagaagc agccaacgccgacacttgctgcgtttgactgaggtgcactcgcaaacagt ctcgtctccccggggcaatttctgagagaaatgcgggaatggacgtaatg gtgctcttctgtgagtgctcttccaccaattttttcgacaagtgttttcgt gacagtcgagtataccttcttatgtcattctgtctccgtcagtgctatcg gattcttcctattcctctaccctttctacagtcgcatacaaagctgctga aacaagacttcctttgtctagggtagttgtacactccacacatatctgac tgaaacctacggcaggaagtctggtcggcactgtgcttccttgttggctt ttcgtcgtttctttgtctacgagcttcactgggtccttgacacggcttgt gagcgttgtgctcaatattcgaccagctgtatttgtg Primers used for cloning:

MIC3F (134-383)-BsaI-F
(SEQ ID NO: 53)
ACTGTGGTCTCTAGGTATGATCTACCATCCTGACAAAAGCTATGGAGGAG
ACT

MIC3F (64-383)-BsaI-R
(SEQ ID NO: 54)
ACTTGTTCTAGATCAGAGACTCGCTGGGTACCTTCGTCT

MIC4 Predicted protein sequence type II ME49:

(SEQ ID NO: 55)
MRASLPVHLVVCTQLSAVWFGVAKAHGGHRLEPHVPGFLQGFTDITPAGD

DVSANVTSSEPAKLDLSCVHSDNKGSRAPTIGEPVPDVSLEQCAAQCKAV

DGCTHFTYNDDSKMCHVKEGKPDLYDLTGGKTASRSCDRSCFEQHVSYEG

APDVMTAMVTSQSADCQAACAADPSCEIFTYNEHDQKCTFKGRGFSAFKE

RGVLGVTSGPKQFCDEGGKLTQEEMEDQISGCIQLSDVGSMTADLEEPME

ADSVGACMERCRCDGRCTHFTFNDNTRMCYLKGDKMQLYSSPGDRTGPKS

CDSSCFSNGVSYVDDPATDVETVFEISHPIYCQVICAANPLCTVFQWYAS

EAKCVVKRKGFYKHRKTGVTGVTVGPREFCDFGGSIRDREEADAVGSDDG

LNAEATMANSPDFHDEVECVHTGNIGSKAQTIGEVKRASSLSECRARCQA

EKECSHYTYNVKSGLCYPKRGKPQFYKYLGDMTGSRTCDTSCLRRGVDYS

QGPEVGKPWYSTLPTDCQVACDAEDACLVFTWDSATSRCYLIGSGFSAHR

RNDVDGVVSGPYTFCDNGENLQVLEAKDTE

The form of MIC4 used in the assay (in bold above):

HisSUMO-
(SEQ ID NO: 56)
SEPAKLDLSCVHSDNKGSRAPTIGEPVPDVSLEQCAAQCKAVDGCTHFTY

NDDSKMCHVKEGKPDLYDLTGGKTASRSCDRSCFEQHVSYEGAPDVMTAM

VTSQSADCQAACAADPSCEIFTYNEHDQKCTFKGRGFSAFKERGVLGVTS

GPKQFCDEGGKLTQEEMEDQISG

Coding sequence (introns spliced out, coding region bold)
Type II ME49:

(SEQ ID NO: 57)
ttttctgtgcatctgtgctgcaaaacgggcctctgtgcattatttcccca ccaacaattgccgcgtcgatccgggtcccgctcaagctctgcagaactag gctctcgatatagatcagtacaatcattcgcttctgacaatcgcatcgac tgagcgacgcgttgatcgtcgactgtcgtgcgtcgcattcgggcatctcg -continued

```
aaccggtgttgattccctgtgtcattatttcacttccgtccttctctcgt
ggcgatctataatacgcgtgtgttgttgcgtgcattgcttgtgttgttgt
ggatgtgttttcttttgtgaccgctcacgaacaccccacgcaaaATGAGA
GCGTCGCTCCCGGTTCACCTCGTTGTGTGCACGCAGCTAAGTGCCGTTTG
GTTTGGAGTGGCTAAAGCCCATGGTGGACACCGACTGGAACCGCATGTTC
CCGGATTCCTGCAAGGCTTCACTGATATCACGCCTGCAGGTGATGACGTT
AGTGCCAACGTAACAAGTTCGGAGCCTGCAAAACTTGATCTCTCTTGTGT
GCACTCTGACAATAAGGGATCAAGGGCTCCCACAATAGGCGAGCCAGTGC
CAGATGTGTCCCTGGAACAATGTGCTGCGCAATGCAAGGCTGTTGATGGC
TGCACACATTTCACTTATAATGACGATTCGAAGATGTGCCATGTGAAGGA
GGGAAAACCCGATTTATACGATCTCACAGGAGGCAAAACAGCATCGCGCA
GTTGCGATAGATCATGCTTCGAACAACACGTATCGTATGAGGGAGCTCCT
GACGTGATGACAGCGATGGTCACGAGCCAGTCAGCGGACTGTCAGGCTGC
GTGTGCGGCTGACCCGAGCTGCGAGATCTTCACTTATAACGAACACGACC
AGAAATGTACTTTCAAAGGAAGGGGGTTTTCTGCGTTTAAGGAACGAGGG
GTGTTGGGTGTGACTTCCGGGCCGAAACAGTTCTGCGATGAAGGCGGTAA
ATTAACTCAAGAGGAGATGGAAGATCAGATCAGTGGCTGCATTCAATTGA
GTGACGTTGGATCAATGACTGCTGACCTGGAGGAGCCTATGGAGGCTGAT
TCTGTTGGCGCTTGTATGGAACGGTGCCGCTGTGATGGAAGATGCACGCA
CTTCACGTTCAACGATAATACTCGGATGTGCTACCTCAAAGGTGACAAGA
TGCAGTTGTACTCATCTCCAGGTGACAGAACCGGCCCAAAGAGCTGCGAT
TCAAGCTGCTTCTCGAACGGGGTTTCTTACGTCGATGATCCGGCGACAGA
TGTTGAGACCGTATTCGAAATTTCACACCCAATTTATTGTCAAGTAATCT
GCGCCGCAAATCCGTTGTGTACAGTGTTTCAGTGGTATGCCTCCGAGGCA
AAGTGCGTCGTCAAGAGAAAGGGGTTTTACAAACACAGAAAAACAGGTGT
CACGGGAGTCACAGTGGGCCCTCGGGAGTTCTGCGATTTTGGCGGTAGCA
TCCGCGACCGAGAAGAGGCAGACGCCGTTGGATCAGACGATGGCCTCAAC
GCGGAAGCAACTATGGCAAATTCTCCTGATTTTCACGACGAAGTAGAATG
CGTCCACACGGGCAACATTGGGTCAAAAGCACAAACCATTGGAGAAGTGA
AACGCGCAAGTAGTTTGAGTGAGTGCAGAGCCAGATGCCAAGCGGAGAAA
GAATGCAGCCACTACACTTACAATGTAAAATCCGGTTTGTGTTATCCAAA
AAGAGGAAAGCCTCAATTTTATAAGTATCTTGGCGACATGACGGGATCCA
GAACATGTGATACAAGTTGCCTTAGGAGGGGAGTCGATTACTCACAGGGC
CCTGAAGTAGGAAAGCCTTGGTATTCTACGCTGCCGACAGACTGCCAAGT
TGCATGCGACGCTGAGGATGCTTGCCTGGTGTTCACCTGGGATTCGGCGA
CGTCACGATGCTACCTCATCGGCTCAGGTTCTCGGCACATCGACGGAAC
GACGTGGATGGCGTGGTATCTGGACCCTATACTTTCTGTGACAATGGCGA
AAACCTTCAGGTGCTTGAAGCGAAAGCACAGAATGAcccaggagggtgc
cagatactttgtgtgactgcgacatgcagtcatgtactcaaagtgttgta
catggacaggaggacttttttttttaagtcattgcagaggtgcgttttcgg
agcagcactataactgcgtcagcgactaagcacgccacgtagctgaatga
aacgcagccaccttcgtgtatgtatgcttcgttttttgtcgctgtgcagt
tttgaatcatttcccttatgggacatttctgaaaaatgctccccgttcgc
ttgtagcactatgagaggggccgaagactgcaatggaggtagcgctgcgt
tgaaaagacgaggcgctacatttcgcgtagcgacaaggccgtgtagagtt
ttgcttttcgcgagacactgctctgagtgtcatatgcatcaaatgcagtg
gtagcacacagaggtgagaagaatgatcacctgcgggggaatggctttgc
taaacaacaaggtcgctgtgtgactttacacaacgaaactactgtggtga
gtgctcagttgagtgaaaagaaatgccgcgttatcgtgagttctggttcg
gtggactttgccaccgtagtaaaactcaacctgtaacggaatgcccagtt
ttactgctctctttaaagggcgtccacgttctctatattcaagctgttta
cccacctgcgtttcggtgcatcgcgcgtgccacatcaaaaatccaggtaa
cggtgcgggacctatgctacactttatatctctcagaaagcatacaccca
ctgattatggacaacgctgtggtcgcgttgtaccacaatgcaggaatact
cagttcaccttgcaagtgttctggtgttcattgcgtgtcagaagtacacg
aaaagagacttctttggcctccaagtgatacgtaaccgcggcagtcatga
acagagtcactcgtgcttctgaaacgcacgtcttctgtacagagacagat
gcagtgtgcatacaggaagcccctcgattgttgccgtagcaggtagccag
tagaagaaacaaagacacggt
```

Primers used for cloning:

MIC4(58-231)-BasI-F
(SEQ ID NO: 58)
ACTGTGGTCTCTAGGTATGAGTTCGGAGCCTGCAAAACTTGATCTCTCTT
GTGT

MIC4(58-231)-XBAI-R
(SEQ ID NO: 59)
ACTGTTCTAGATCAGCCACTGATATGATCTTCCATCTCCTCTTGAGT

MIC6 Predicted protein sequence type II ME49:

(SEQ ID NO: 60)
MRLFRCCAAAVVAAESLLWLKNG**SPFFAFLPGNGEIADNCSGNPCGGTAA
GTCINTPSGYDCRCEPGYVLGVENDQVTCMMPSGVPMANFVQLSEKPAAC
SSNPCGPEAAGTCNETNSGYICRCNQGYRISLDGTGNVTCIVRQESGCEE
NGCGPPDAVQSCRRLTGTAGRLCVCKENFIATIDASAHITCKRVPPHYRK
PPFEFGKGGHPVDSEPSKRQREDEGESREPESDSTEPGRDQERRTPLEES
QEPEGSTPDSQQSRGGSGSDSTESEEQGKEREEGSGHAGAIAGGVIGGLL
LLSAAGAGVAYMRKSGSGGGEEIEYERGIEAAEASEVEVLVDLDSKTWD**

The form of MIC6 used in the assay (in bold above):

His-SUMO
(SEQ ID NO: 61)
SPFFAFLPGNGEIADNCSGNPCGGTAAGTCINTPSGYDCRCEPGYVLGVE
NDQVTCMMPSGVPMANFVQLSEKPAACSSNPCGPEAAGTCNETNSGYICR
CNQGYRISLDGTGNVTCIVRQESGCEENGCGPPDAVQSCRRLTGTAGRLC

VCKENFIATIDASAHITCKRVPPHYRKPPFEFGKGGHPVDSEPSKRQRED

EGESREPESDSTEPGRDQERRTPLEESQEPEGSTPDSQQSRGGSGSDSTE

SEEQGKEREEGSGHAGAIAGGVIGGLLLLSAAGAGVAYMRKSGSGGGEEI

EYERGIEAAEASEVEVLVDLDSKTWD

Coding sequence (introns spliced out, coding region bold) Type II ME49:

(SEQ ID NO: 62)
cagtccggagcacactcctacaataaacttgatacgtgtcattttgtgaa acgacacagcacataaccactcggactgtctcacgaagctgtagggcgga ttcaccaatgatctttcgcagccgatccaaaactacttgcccacttccgg tgtacgtacatcgcgcgacatgagaggcattcattgttttccatagaaaa cactactggacaaccattcggtagcgcacaagttgagcctctgacaaatc tttcctcatcacgtgaatacacgctgcgtgattcgtcagtgactccactg tggtctttaaccaccatcagagtcctgtaagcatcctttgtttccgttta aaatgcctgccagatggcacgacgcgtctggttttgccggcttctccg agtcctattagactttgatgccttacggcttttttttaagaatggttctt ttgagatttgccgactttccagttccgccaccagacgctcctgttgaact gccaccggcacgatgcagtattccgccacgaaaacgcgcaccgcaagctc cgctaccattaaacgggtttcgtctgctttagatgtttccttccgcgtca tcaaggcaaaagcattgccactgatgttaccgaagctttcccgccatgct gcgcacaatgcccaatcttccgtcacggacctcttccggtaaccacctaa aggaggattactgggcaacccaaaacgctgcaacaagaagcacagtccag gtgtcgctagattcgagcctgcatggtcgttccgtagctccatacaacaa ttctctgtgtgacggcgagaggagtaacgcgctagtgtgtcagcgacg cggcagtcgatccgatcctgcaacaggcagaggtgtgtcgatgctcagtg atgcgacggcgtatctgaagaggactgtagctccaccacgaccttcgtgg gagcacgaagtgtactctgttgtcgtcggtctcgtattttttgagttgt gtacttcgctgcaagaggagggtgagattcgacatctgtgggcgtttggg atcgtgatgacatcgactgtgctttgatatgatgtgttttttttcgat tggatgagcacattccagtaagcttcctgccgcgcgtctctgctATGAGG

CTCTTCCGGTGCTGTGCTGCGGCCGTTGTGGCGGCCGAATCGTTACTGTG

GCTGAAGAACGGCTCCCCGTTTTTTGCCTTTCTTCCTGGGAATGGAGAGA

TTGCAGACAACTGCTCTGGGAATCCATGCGGTGGCACCGCAGCTGGTACG

TGCATAAACACACCATCTGGATATGATTGCAGGTGCGAACCAGGCTACGT

TCTGGGCGTTGAAAATGACCAGGTCACGTGCATGATGCCCTCAGGTGTAC

CCATGGCTAATTTTGTACAGCTGTCGGAAAAGCCTGCAGCTTGCAGCTCA

AACCCTTGTGGACCTGAGGCAGCCGGCACCTGCAACGAGACAAACAGTGG

TTACATTTGCCGCTGTAATCAAGGCTACAGAATATCTCTCGACGGGACAG

GAAACGTGACATGTATTGTAAGACAGGAAAGCGGCTGTGAGGAAAACGGG

TGTGGGCCGCCAGATGCAGTACAGAGTTGCCGCCGACTAACAGGGACGGC

AGGTCGACTATGTGTATGCAAGGAAAACTTTATAGCGACAATCGACGCCA

GTGCCCATATCACCTGCAAGCGTGTGCCTCCCCATTATAGGAAGCCTCCC

TTCGAATTTGGCAAGGGAGGTCATCCTGTGGACTCAGAACCATCGAAACG

CCAGAGGGAAGATGAAGGTGAAAGTCGTGAGCCTGAAAGCGACTCAACAG

AACCGGGGAGAGATCAGGAAAGAAGAACACCCACTTGAGGAAAGCCAGGAA

CCGGAAGGAAGCACCCCGGACAGTCAGCAGAGCCGAGGTGGTTCTGGTAG

CGACAGTACCGAGAGCGAGGAACAAGGAAAGGAGAGAGAGGAAGGAAGTG

GACATGCTGGTGCGATCGCTGGGGGAGTTATTGGAGGCCTGTTACTTCTG

AGCGCTGCCGGAGCGGGTGTTGCATACATGAGAAAGAGTGGGAGCGGTGG

AGGGGAGGAGATAGAATACGAGAGGGGTATCGAGGCTGCAGAGGCCAGTG

AAGTCGAAGTCCTCGTTGATTTGGATAGCAAAACATGGGATTAAcacgtt ctcggctgagacttcacaatgtagggtgtcgctggcagatcagctgcaat gcgagaggtgacgcgagtagtgagcaccgcttcttttaagcgcggacatt gtgctcggtcttctgtcaccccgaatcaaaacacatgtatgataatagt tcctgttgacttccctgccgacaaagaactgctgtgtcgaggccggctt ctgtgcactcatcccaaatgagatggactgatgttttagagacacctcat cgccgacggaaaccatcagctcccagagaaactatgctgcgtcgttttt aggtgatctgttgcgtaatgcgcaccttcatatcatctgtgtgttgactg tttggtcgttttccgtttagtcaaatgaatgcagtgaaatgcagggaatt tagcagacaccgagaactgtcctcttgttctgtgcgcgagttgtttttaa cgtatagcgatgcgtttgcacttgatattaccctaagccatcagtgggta tttagaggagcccacaggtgatggggtgatccctgtttcttgtcatttg gcttgtagggttcgctggaactatctggtgtcacggaagagtggctttac tgtctgtccccaaacgcaaggcatcagtgtaaccccgataggactctgga gacttctgcttcactgccgcgttgcaattttcccgcgtcatgtggcaata acggtaattccacgtgcacgccgcataccggatctttgctcccaggcttt cttatgaggtcggcatacgtacagcggcggcgtacctccgctctagaaa gaccggtccaaccgactttgaacagcatgcttgtgaatgagtgcttaaac accctgaagtgatggtggaatgtagcagtctgggacggttgatgcgagga tatcaccattagcatagactaccttgctctttagcgaggcgagacaactt atttaggtagccatgaaacacctcgatagtatcaatgacgacgtgcggtt caccaacttccgtcgctagcgcagaaaacagtcggaaacacaactcggtg agcacctgaagtgtcagtacacattcgaccgtcgggaccgggattccgc aagtggcacccgctggtccagtagcaggaacctagttcattcagtataac agatttggggcggcaaagagcaatttgctcgacctaacgcttgc Primers used for cloning:

MIC6-(24-349)-BasI-F
(SEQ ID NO: 63)
ACTGTGTGCTCTAGGTATGTCCCCGTTTTTGCCTTTCTTCCTG

MIC6-(24-349)BasI-R
(SEQ ID NO: 64)
ACTGTTCTAGATTAATCCCATGTTTTGCTATCCAAATCA

SUMO Protein sequence:

This sequence is present at the N-terminus of SUMO fusions

Coding sequence for His tagged SUMO (His-SUMO)

(SEQ ID NO: 16)
ATGGGTCATCACCATCATCATCACGGGTCCCTGCAGGACTCAGAAGTCAA

TCAAGAAGCTAAGCCAGAGGTCAAGCCAGAAGTCAAGCCTGAGACTCACA

TCAATTTAAAGGTGTCCGATGGATCTTCAGAGATCTTCTTCAAGATCAAA

AAGACCACTCCTTTAAGAAGGCTGATGGAAGCGTTCGCTAAAAGACAGGG

TAAGGAAATGGACTCCTTAAGATTCTTGTACGACGGTATTAGAATTCAAG

CTGATCAGGCCCCTGAAGATTTGGACATGGAGGATAACGATATTATTGAG

GCTCACCGCGAACAGATTGGAGGT

Predicted protein sequence for His-SUMO:

(SEQ ID NO: 17)
MGHHHHHHGSLQDSEVNQEAKPEVKPEVKPETHINLKVSDGSSEIFFKIK

KTTPLRRLMEAFAKRQGKEMDSLRFLYDGIRIQADQAPEDLDMEDNDIIE

AHREQIGG

Example 2

We have developed an efficient assay where we can control the amplitude of antigen release pharmacologically. We compared constitutive secretion (mock treatment), to conditions where we block or enhance microneme secretion. *T. gondii* antigens released into the extracellular milieu are likely to stimulate both humoral and cell-mediated immunity. Identification of immunogenic proteins in ESA has led to improved diagnostic reagents for *T. gondii* infection.

Collection of Excreted/Secreted Antigen (ESA)

*Toxoplasma gondii* RH strain parasites were isolated from infected human fibroblasts, filtered, and washed extensively. Parasites were either left untreated (Mock), treated to block (Inhibited), or induce secretion of ES antigens (Stimulated). After 10 min at 37° C., the parasites were chilled to 4° C., centrifuged, and the cell-free supernatant was collected. To evaluate the complexity, samples were separated by SDS-PAGE and the protein composition was assessed by staining. In addition, we used a luciferase-based assay to detect a microneme reporter to specifically determine the level of microneme secretion in each of the fractions (FIG. 1).

LC/MS-MS of ES Antigens

Samples were processed for mass spectrometry (MS), separated by LC, resolved on an Orbitrap MS/MS instrument, and analyzed using Mascot (Matrix Science, London, UK). Scaffold (Proteome Software Inc., Portland, Oreg.) was used to analyze MS/MS peptides and establish protein identifications by comparison to gene databases.

We classified ES antigens based on enrichment of peptides in stimulated vs. blocked samples using a cutoff of 4-fold increase in two replicate samples. The proteins were further analyzed for their profile of expression during development to classify those that were bone fide micronemal proteins (the major component of ESA) vs. potential contaminants. The profile of microneme proteins is highly characteristic and many of the secreted proteins share this transcriptional profile. Based on the fold enrichment and expression pattern, we generated a list of the most abundantly induced proteins in ESA (Table 1).

TABLE 1

Summary of ESA proteins identified by mass spectrometry.

| Gene ID | Product Description | Fold Increase[1] |
|---|---|---|
| TGME49_267680 | microneme protein MIC12 (MIC12) | 39.0 |
| TGME49_291890 | microneme protein MIC1 (MIC1) | 34.7 |
| TGME49_294330 | EGF family domain-containing protein | 34.0 |
| TGME49_208030 | microneme protein MIC4 (MIC4) | 28.8 |
| TGME49_201780 | microneme protein MIC2 (MIC2) | 27.3 |
| TGME49_319560 | microneme protein MIC3 (MIC3) | 26.1 |
| TGME49_206510 | toxolysin TLN4 (TLN4) | 25.0 |
| TGME49_214940 | MIC2-associated protein M2AP | 21.5 |
| TGME49_234380 | hypothetical protein (TGME49_234380) | 16.5 |
| TGME49_204050 | subtilisin SUB1 (SUB1) | 16.5 |
| TGME49_218520 | microneme protein MIC6 (MIC6) | 15.5 |
| TGME49_250710 | microneme protein MIC10 (MIC10) | 13.2 |
| TGME49_293440 | hypothetical protein (TGME49_293440) | 13.0 |
| TGME49_232280 | hypothetical protein (TGME49_232280) | 11.5 |
| TGME49_204130 | perforin-like protein PLP1 (PLP1) | 11.5 |
| TGME49_243930 | hypothetical protein (TGME49_243930) | 5.5 |
| TGME49_277080 | microneme protein MIC5 (MIC5) | 5.4 |
| TGME49_258870 | hypothetical protein (TGME49_258870) | 4.5 |

[1]Increase of peptide spectral counts in stimulated fraction vs. control

Example 3

Figure 2:
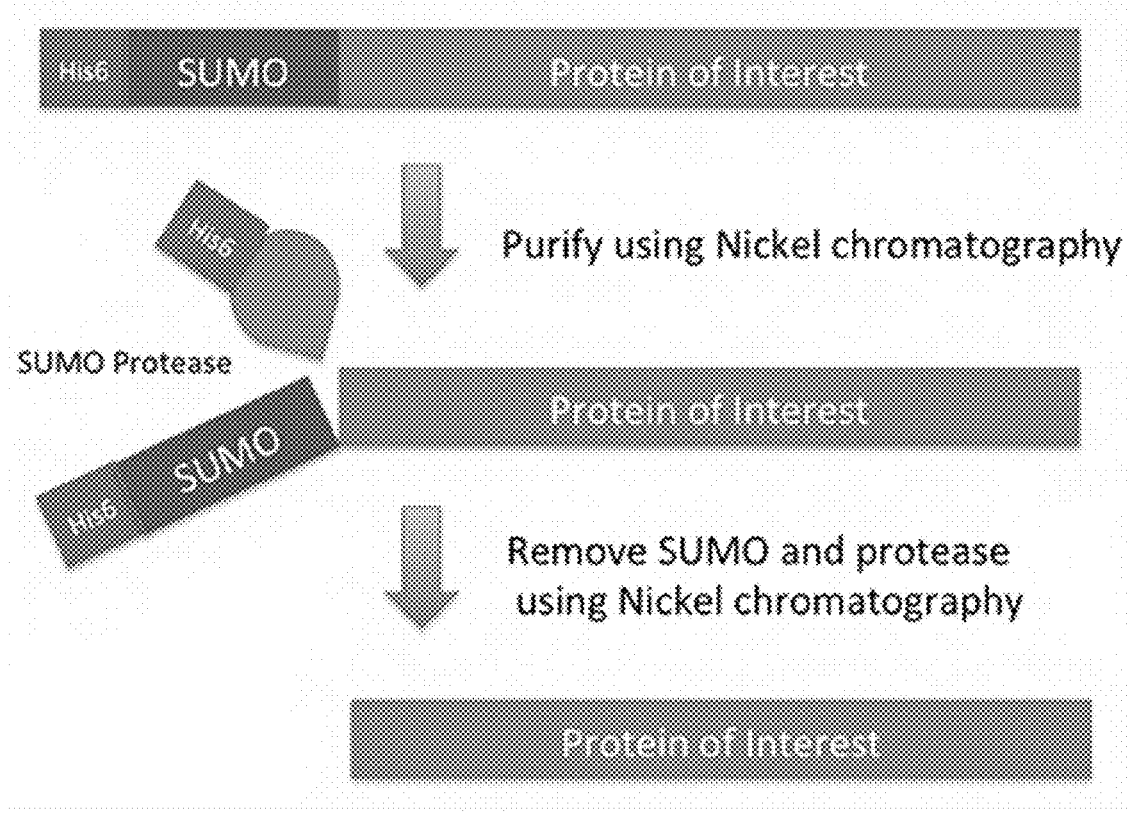
FIG. 2 shows an expression system for purification of fusion proteins. SUMO is a ubiquitin-like protein that is highly soluble, aiding in the expression of proteins in *E. coli*. Proteins can be cleaved by SUMO protease to release tag-free proteins of high purity. The SUMO-fusion protein and the SUMO protease are both tagged with six histidine residues that mediate binding to nickel, allowing one step purification by affinity chromatography.

To express these proteins recombinantly, we are using a fusion system based on the *E. coli* protein SUMO, which allows for production and purification of soluble, tagged proteins. From this group of initial candidates, we have successfully cloned, expressed, and purified all of the proteins shown in Table 2. These proteins were tested here as fusion proteins with SUMO as a control. However, they can also be purified away form SUMO after protease cleavage by nickel chromatography as shown in FIG. 2.

Example 4

Development of Model for DTH Using Bioluminescence

We tested an alternative method that relies on light production in the skin. The basis for this method is that recruitment of monocytes and neutrophils to the site of inflammation can be detected using luminol, a substrate that gives off light when converted by myeloperoxidase (Gross S, Gammon S T, Moss B L, Rauch D, Harding J, Heinecke J W, Ratner L, Piwnica-Worms D. 2009. Bioluminescence imaging of myeloperoxidase activity in vivo. Nat Med 15:455-461). This method has been shown to be sensitive for detecting DTH responses in the mouse and for monitoring leukocyte influx to sites of infiltration (Gross, supra).

Example 5

The Luminol DTH Response is Specific to ESA

Figure 3A:
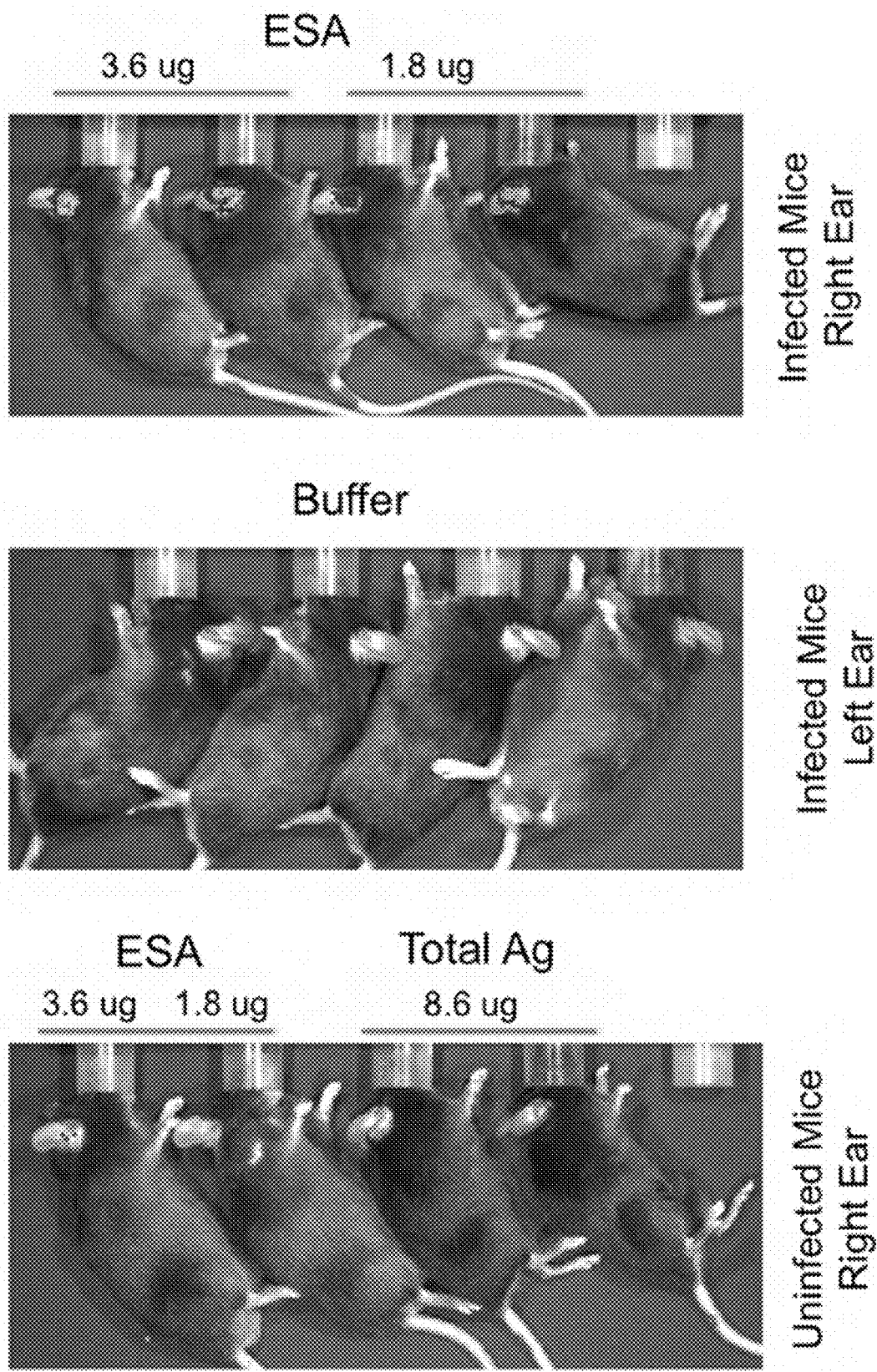
FIG. 3A) Animals were injected with antigens in the ear pinne. At 48 hr after injection, animals were imaged after injection of luminol using a Xenogen IVIS 200 instrument. Animals were injected with either ESA or total antigen. Numbers indicate antigen amounts in micrograms.
Figure 3B:
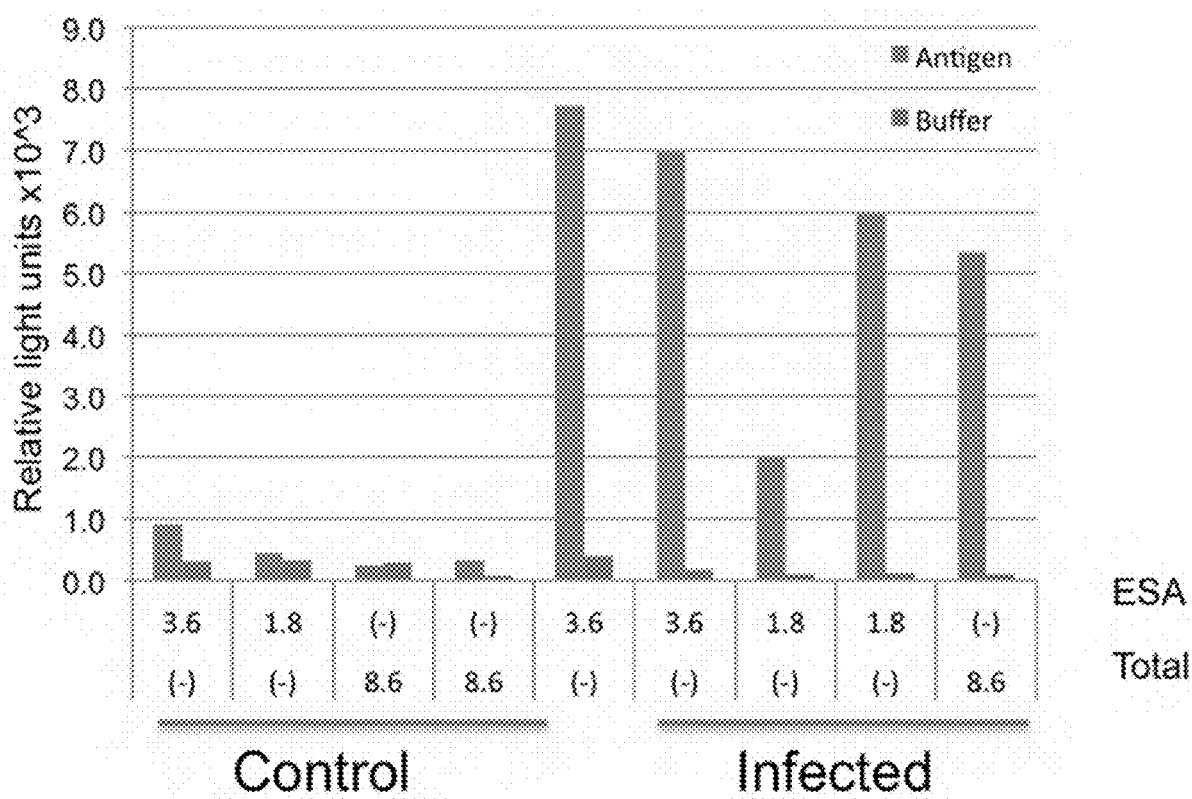
FIG. 3B) Quantification of the images shown in A. Data were processed using Living Image software.

We have modified the luminol assay used for monitoring DTH responses in the mouse by injecting antigen in the pinne of the ear. In order to confirm that the DTH responses that we were detecting were in fact due to antigens in ESA, we compared the response for ESA to total parasite antigen or to PBS. The response detected by luminol was highly enriched in ESA sample compared to the PBS control or to total antigen (FIG. 3A, 3B). The response is also only seen in infected animals, confirming that it is due to a specific immune response. This experiment demonstrates that the DTH response is driven by antigens that are enriched in ESA.

Example 6

Figures 4, 5:
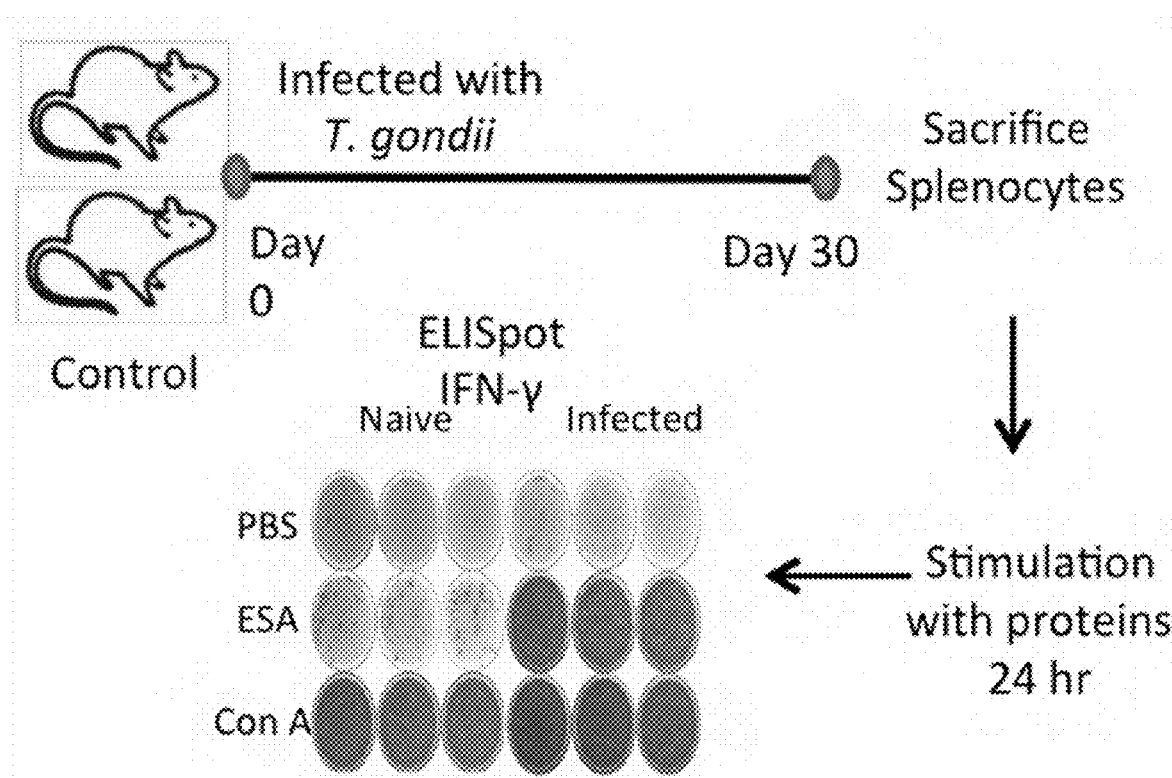
FIG. 4 Monitoring of lipopolysaccharide (LPS) using the limulus amebocyte assay (LAL). After purification over polymixin B resin, the level of LPS as monitored by the LAL assay was reduced by >50 fold.
FIG. 5. shows ELISpot assay detecting IFN-γ produced by splenocytes from naive and *T. gondii* infected mice. Samples treated with PBS or ESA during in vitro culture. Con A serves as a non-specific positive control.

We have focused on the ESA antigens defined in Table 1 along with some constitutively secreted dense granule proteins (GRA) that have previously been shown to be immunogenic. We have cloned, expressed, and purified 12 proteins for testing, as shown in Table 2. Test proteins were purified as fusion proteins with SUMO, an *E. coli* protein that facilitates solubility. We have also purified the SUMO protein as a control. To avoid non-specific responses due to endotoxin (LPS) we purified ESA proteins using polymyxin B, a detergent like molecule that removes endotoxin. The resulting purified proteins showed reduced levels of LPS when examined using the limulus amebocyte assay (FIG. 4).

TABLE 2

| ESA Protein | Constructs (aa) | Clone Vector | Strain | Molecular weight (kD) |
|---|---|---|---|---|
| MIC10 | Full length | pE-SUMO | Rosetta (DE3) | 23.1 |
| GRA7 | Full length | pE-SUMO | Rosetta (DE3) | 26 |
| GRA6 | Full length | pE-SUMO | Rosetta [DE3] | 25 |
| M2AP | Full length | pE-SUMO | Rosetta (DE3) | 34.6 |
| MIC5 | Full length | pE-SUMO | Rosetta [DE3] | 19.9 |
| MIC6 | Full length | pE-SUMO | Rosetta (DE3) | 36.7 |
| Hypothetic Protein 2 (TGME49_232280) | Full length | pE-SUMO | Rosetta (DE3) | 30.2 |
| GRA4 | 21-247 | pE-SUMO | Rosetta (DE3) | 38 |
| MIC1 | 20-340 | pE-SUMO | Rosetta (DE3) | 48.6 |
| MIC3 | 134-383 | pE-SUMO | Rosetta (DE3) | 40.5 |
| MIC4 | 58-231 | pE-SUMO | Rosetta (DE3] | 63.0 |
| Hypothetic Protein 1 (TGME.234380) | 89-347 | pE-SUMO | Rosetta (DE3) | 38.7 |

Example 7

An In Vitro Method to Monitor Antigen Presentation

This method is based on the ability of specialized immune cells (dendritic cells and macrophages) to present antigen to memory T-cells that in turn produce interferon gamma (IFN-γ). T-cells that produce IFN-γ in response to recall antigens are one of the primary drivers of the DTH response (Black C A. 1999. Delayed type hypersensitivity current theories with an historic perspective. Dermatol Online J 5:7.). However, instead of injecting antigens into the skin, we monitored the production of IFN-γ using a technique called ELISpot to specifically detect IFN-γ producing T-cells following antigen presentation in vitro. Following incubation of splenocytes with specific antigens or controls, IFN-γ is captured by an antibody on the membrane and then detected using an enzyme-linked immuno-assay (the blue spots represent positives). As shown in FIG. 5, this assay measures robust responses of splenocytes from *T. gondii* infected mice incubated with ESA, while there is minimal response in naive animals. ConA is used as a non-specific stimulus as it evokes responses from all T-cells regardless of specific antigen presentation. We have adapted this assay for monitoring recombinant ESA proteins and peptides that are synthetically produced.

Example 8

Using the ELISpot Assay to Monitor IFN-γ Secretion to Individual ESA Proteins

Figure 6A:
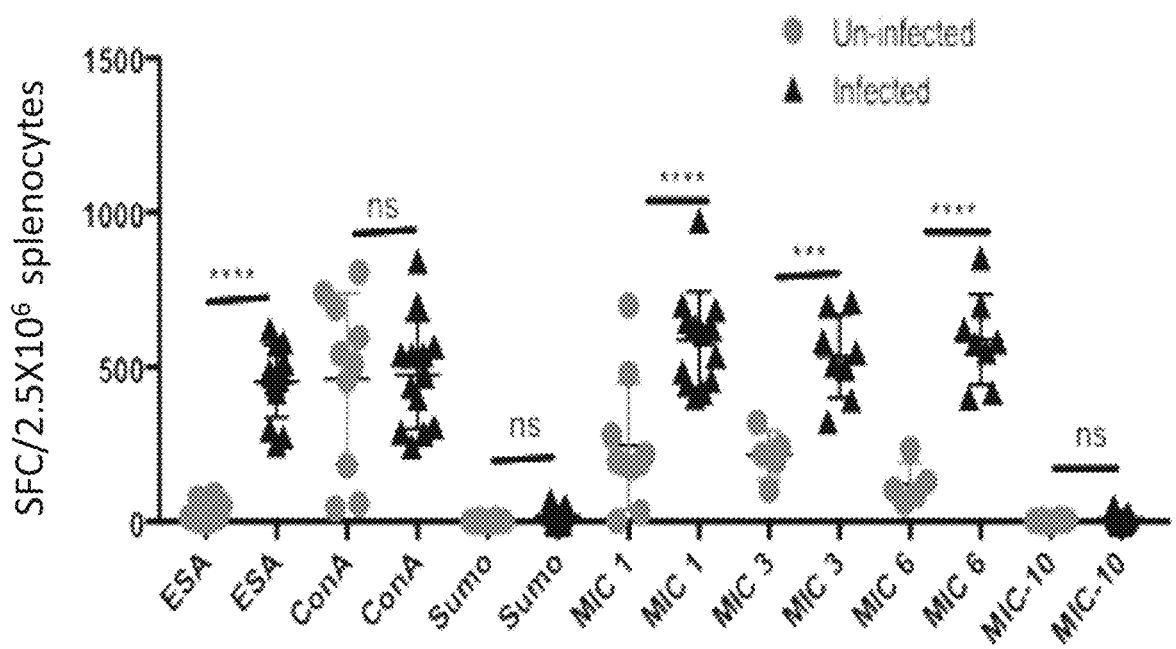
FIG. 6A) Responses from C57/BL6 mice, FIG. 6B) Responses from Balb/C mice. Individual data points represent a result from one mouse, either uninfected (gray) or chronically infected (black). SFC indicates "spot forming cells" that were positive for INFγ secretion.
Figure 6B:
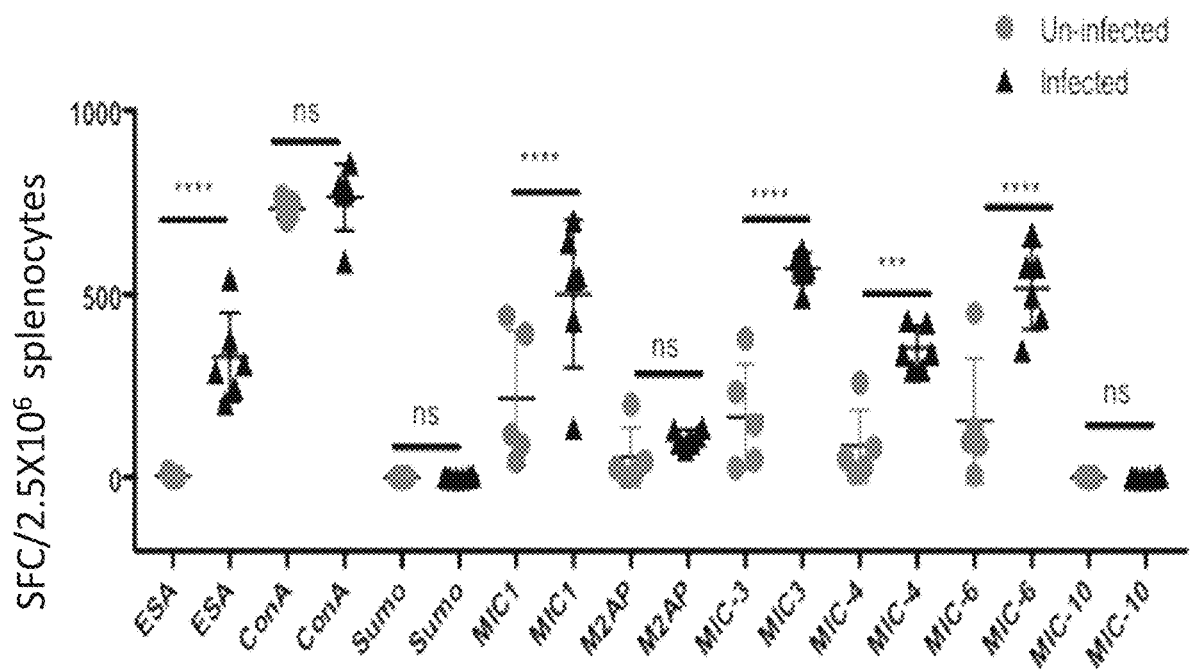
FIG. 6. shows ELISpot data for IFN-γ secretion by T cell in response to purified ESA proteins.

The ELISpot assay was also used to examine the response of uninfected and chronically infected mice to individual ESA proteins that were produced recombinantly. Initially, the ESA fraction was compared to ConA as a positive control and SUMO as a negative control. High numbers of spot forming cells (SFC) were detected using an IFN-γ specific ELISpot assay as shown in FIG. 6. Individual ESA proteins were used at 3 micrograms per well in combination with $10^5$ splenocytes. Specific responses were detected to MIC1, MIC3, MIC4 and MICE, but not to M2AP or to MIC10 as shown in FIG. 6. Similar responses were seen in infected C57/BL6 mice (FIG. 6A) and Balb/C mice (FIG. 6B).

REFERENCES

The disclosure of each reference cited below and throughout this application is expressly incorporated herein.

References for Example 1

1. Brown, K. M., S. Lourido, and L. D. Sibley, *Serum Albumin Stimulates Protein Kinase G-dependent Microneme Secretion in Toxoplasma gondii*. J Biol Chem, 2016. 291(18): p. 9554-65.
2. Etheridge, R. D., et al., *ROP18 and ROP17 kinase complexes synergize to control acute virulence of Toxoplasma in the mouse*. Cell Host Microbe, 2014. 15: p. 537-550.
3. Behnke, M., et al., *Coordinated progression through two subtranscriptions underlies the tachyzoite cycle of Toxoplasma gondii*. Plos One, 2010. 5: p. e12354.
4. Khan, A., et al., *Geographic separation of domestic and wild strains of Toxoplasma gondii in French Guiana correlates with a monomorphic version of chromosome 1a*. Plos Negl. Trop. Dis., 2014. 8: p. e3182.
5. Gross, S., et al., *Bioluminescence imaging of myeloperoxidase activity in vivo*. Nat Med, 2009. 15(4): p. 455-61.

References for Examples 2-4

1. Carruthers V B, Sibley L D. 1997. Sequential protein secretion from three distinct organelles of *Toxoplasma gondii* accompanies invasion of human fibroblasts. Eur J Cell Biol 73:114-123.
2. Carruthers V B, Giddings O K, Sibley L D. 1999. Secretion of micronemal proteins is associated with *Toxoplasma* invasion of host cells. Cell Microbiol 1:225-236.
3. Carruthers V B, Moreno S N J, Sibley L D. 1999. Ethanol and acetaldehyde elevate intracellular [Ca2+] calcium and stimulate microneme discharge in *Toxoplasma gondii*. Biochem J 342:379-386.
4. Carruthers V B, Sibley L D. 1999. Mobilization of intracellular calcium stimulates microneme discharge in *Toxoplasma gondii*. Mol Microbiol 31:421-428.

5. Huynh M H, Barenau K E, Harper J M, Beatty W L, Sibley L D, Carruthers V B. 2003 Rapid invasion of host cells by *Toxoplasma* requires secretion of the MIC2-M2AP adhesive protein complex. EMBO J 22:2082-2090.
6. Brydges S D, Sherman G D, Nockemann S, Loyens A, Daubener W, Dubremetz J, Carruthers V B. 2000. Molecular characterization of TgMIC5, a proteolytically processed antigen secreted from the micronemes of *Toxoplasma gondii*. Mol Biochem Parasitol 111:51-66.
7. Hoff E F, Cook S H, Sherman G D, Harper J M, Ferguson D J, Dubremetz J F, Carruthers V B. 2001. *Toxoplasma gondii*: molecular cloning and characterization of a novel 18-kDa secretory antigen, TgMIC10. Exp Parasitol 97:77-88.
8. Mercier C, Cesbron-Delauw M F. 2015. *Toxoplasma* secretory granules: one population or more? Trends Parasitol 31:60-71.
9. Black C A. 1999. Delayed type hypersensitivity: current theories with an historic perspective. Dermatol Online J 5:7.
10. Allen I C. 2013. Delayed-type hypersensitivity models in mice. Methods Mol Biol 1031:101-107.
11. Rougier D, Ambroise-Thomas P. 1985. Detection of toxoplasmic immunity by multipuncture skin test with excretory-secretory antigen. Lancet 2:121-123.
12. Veprekova. 1978. Approximative molecular weight of the active component in toxoplasmin. Folia Parasitol (Praha) 25:273-275.
13. Frenkel J K. 1948. Dermal hypersentsitivity to *toxoplasma* antigens (toxoplasmins). Proc Soc Exp Biol Med 68:634-639.
14. Gross S, Gammon S T, Moss B L, Rauch D, Harding J, Heinecke J W, Ratner L, Piwnica-Worms D. 2009. Bioluminescence imaging of myeloperoxidase activity in vivo. Nat Med 15:455-461

References for Examples 5-6

1. Carruthers V B, Sibley L D. 1997. Sequential protein secretion from three distinct organelles of *Toxoplasma gondii* accompanies invasion of human fibroblasts. Eur J Cell Biol 73:114-123.
2. Carruthers V B, Giddings O K, Sibley L D. 1999. Secretion of micronemal proteins is associated with *Toxoplasma* invasion of host cells. Cell Microbiol 1:225-236.
3. Carruthers V B, Moreno S N J, Sibley L D. 1999. Ethanol and acetaldehyde elevate intracellular [Ca2+] calcium and stimulate microneme discharge in *Toxoplasma gondii*. Biochem J 342:379-386.
4. Carruthers V B, Sibley L D. 1999. Mobilization of intracellular calcium stimulates microneme discharge in *Toxoplasma gondii*. Mol Microbiol 31:421-428.
5. Huynh M H, Barenau K E, Harper J M, Beatty W L, Sibley L D, Carruthers V B. 2003. Rapid invasion of host cells by *Toxoplasma* requires secretion of the MIC2-M2AP adhesive protein complex. EMBO J 22:2082-2090.
6. Brydges S D, Sherman G D, Nockemann S, Loyens A, Daubener W, Dubremetz J, Carruthers V B. 2000. Molecular characterization of TgMIC5, a proteolytically processed antigen secreted from the micronemes of *Toxoplasma gondii*. Mol Biochem Parasitol 111:51-66.
7. Hoff E F, Cook S H, Sherman G D, Harper J M, Ferguson D J, Dubremetz J F, Carruthers V B. 2001. *Toxoplasma gondii*: molecular cloning and characterization of a novel 18-kDa secretory antigen, TgMIC10. Exp Parasitol 97:77-88.
8. Mercier C, Cesbron-Delauw M F. 2015. *Toxoplasma* secretory granules: one population or more? Trends Parasitol 31:60-71.
9. Black C A. 1999. Delayed type hypersensitivity: current theories with an historic perspective. Dermatol Online J 5:7.
10. Allen I C. 2013. Delayed-type hypersensitivity models in mice. Methods Mol Biol 1031:101-107.
11. Rougier D, Ambroise-Thomas P. 1985. Detection of toxoplasmic immunity by multipuncture skin test with excretory-secretory antigen. Lancet 2:121-123.
12. Veprekova. 1978. Approximative molecular weight of the active component in toxoplasmin. Folia Parasitol (Praha) 25:273-275.
13. Frenkel J K. 1948. Dermal hypersensitivity to *toxoplasma* antigens (toxoplasmas]. Proc Soc Exp Biol Med 68:634-639.
14. Gross S, Gammon S T, Moss B L, Rauch D, Harding J, Heinecke J W, Ratner L, Piwnica-Worms D. 2009. Bioluminescence imaging of myeloperoxidase activity in vivo. Nat Med 15:455-461.

References for Examples 7

1. Huynh M H, Barenau K E, Harper J M, Beatty W L, Sibley L D, Carruthers V B. 2003. Rapid invasion of host cells by *Toxoplasma* requires secretion of the MIC2-M2AP adhesive protein complex. EMBO J 22:2082-2090.
2. Brydges S D, Sherman G D, Nockemann S, Loyens A, Daubener W, Dubremetz J, Carruthers V B. 2000. Molecular characterization of TgMIC5, a proteolytically processed antigen secreted from the micronemes of *Toxoplasma gondii*. Mol Biochem Parasitol 111:51-66.
3. Hoff E F, Cook S H, Sherman G D, Harper J M, Ferguson D J, Dubremetz J F, Carruthers V B. 2001. *Toxoplasma gondii*: molecular cloning and characterization of a novel 18-kDa secretory antigen, TgMIC1O. Exp Parasitol 97:77-88.
4. Mercier C, Cesbron-Delauw M F. 2015. *Toxoplasma* secretory granules: one population or more? Trends Parasitol 31:60-71.
5. Black C A. 1999. Delayed type hypersensitivity: current theories with an historic perspective. Dermatol Online J 5:7.
6. Allen I C. 2013. Delayed-type hypersensitivity models in mice. Methods Mol Biol 1031:101-107.
7. Rougier D, Ambroise-Thomas P. 1985. Detection of toxoplasmic immunity by multipuncture skin test with excretory-secretory antigen. Lancet 2:121-123.
8. Veprekova. 1978. Approximative molecular weight of the active component in toxoplasmin. Folia Parasitol (Praha) 25:273-275.
9. Frenkel J K. 1948. Dermal hypersensitivity to *toxoplasma* antigens (toxoplasmins). Proc Soc Exp Biol Med 68:634-639.
10. Gross S, Gammon S T, Moss B L, Rauch D, Harding J, Heinecke J W, Ratner L, Piwnica-Worms D. 2009. Bioluminescence imaging of myeloperoxidase activity in vivo. Nat Med 15:455-461.
11. Philpott D J, Girardin S E. 2004. The role of Toll-like receptors and Nod proteins in bacterial infection. Molec Immunol 41:1099-1108.
12. Jacobs D M, Morrison D C. 1977. Inhibition of the mitogenic response to lipopolysaccharide (LPS) in mouse spleen cells by polymyxin B. J Immunol 118:2127.

13. Nielsen M, Lund O, Buus S, Lundegaard C. 2010. MHC class II epitope predictive algorithms. Immunology 130: 319-328.
14. Wang P, Sidney J, Dow C, Mothe B, Sette A, Peters B. 2008. A systematic assessment of MHC class II peptide binding predictions and evaluation of a consensus approach. PLoS Comput Biol 4:e1000048.
15. Erskine C L, Krco C), Hedin K E, Borson N D, Kalli K R, Behrens M D, Heman-Ackah S M, von Hofe E, Wettstein P J, Mohamadzadeh M, Knutson K L. 2011. MHC class II epitope nesting modulates dendritic cell function and improves generation of antigen-specific CD4 helper T cells. J Immunol 187:316-324.

The invention claimed is:

1. An in vitro method of monitoring a T cell response in a T cell from a subject, wherein the subject has not been immunized against *Toxoplasma gondii*, the method comprising:
 contacting the T cell of the subject with a composition comprising an isolated *Toxoplasma gondii* antigen selected from the group consisting of:
  a. isolated and purified MIC1,
  b. truncated MIC1,
  c. extended MIC1, and
  d. combinations thereof, and detecting or quantifying release of a cytokine.

2. The method of claim 1 wherein the response is a delayed type hypersensitivity response.

3. The method of claim 1 wherein the response is release of a cytokine.

4. The method of claim 1 wherein the response is release of interferon-γ.

5. The method of claim 1 wherein the T cells are in peripheral blood mononuclear cells.

6. The method of claim 1 wherein the T cells are in a blood sample.

7. The method of claim 1 further comprising the step of detecting or quantifying release of interferon-γ.

* * * * *

```
                        SEQUENCE LISTING

<160> NUMBER OF SEQ ID NOS: 64

<210> SEQ ID NO 1
<211> LENGTH: 456
<212> TYPE: PRT
<213> ORGANISM: Toxopolasmosis gondii

<400> SEQUENCE: 1

Met Gly Gln Ala Leu Phe Leu Thr Val Leu Pro Val Leu Phe Gly
1               5                   10                  15

Val Gly Pro Glu Ala Tyr Gly Glu Ala Ser His Ser His Ser Pro Ala
            20                  25                  30

Ser Gly Arg Tyr Ile Gln Gln Met Leu Asp Gln Arg Cys Gln Glu Ile
            35                  40                  45

Ala Ala Glu Leu Cys Gln Gly Gly Leu Arg Lys Met Cys Val Pro Ser
        50                  55                  60

Ser Arg Ile Val Ala Arg Asn Ala Val Gly Ile Thr His Gln Asn Thr
65                  70                  75                  80

Leu Glu Trp Arg Cys Phe Asp Thr Ala Ser Leu Leu Glu Ser Asn Gln
                85                  90                  95

Glu Asn Asn Gly Val Asn Cys Val Asp Asp Cys Gly His Thr Ile Pro
            100                 105                 110

Cys Pro Gly Gly Val His Arg Gln Asn Ser Asn His Ala Thr Arg His
        115                 120                 125

Glu Ile Leu Ser Lys Leu Val Glu Gly Val Gln Arg Phe Cys Ser
    130                 135                 140

Pro Tyr Gln Ala Ser Ala Asn Lys Tyr Cys Asn Asp Lys Phe Pro Gly
145                 150                 155                 160

Thr Ile Ala Arg Arg Ser Lys Gly Phe Gly Asn Asn Val Glu Val Ala
                165                 170                 175

Trp Arg Cys Tyr Glu Lys Ala Ser Leu Leu Tyr Ser Val Tyr Ala Glu
            180                 185                 190

Cys Ala Ser Asn Cys Gly Thr Thr Trp Tyr Cys Pro Gly Gly Arg Arg
        195                 200                 205

Gly Thr Ser Thr Glu Leu Asp Lys Arg His Tyr Thr Glu Glu Glu Gly
    210                 215                 220

Ile Arg Gln Ala Ile Gly Ser Val Asp Ser Pro Cys Ser Glu Val Glu
225                 230                 235                 240

Val Cys Leu Pro Lys Asp Glu Asn Pro Val Cys Leu Asp Glu Ser
                245                 250                 255

Gly Gln Ile Ser Arg Thr Gly Gly Pro Ser Gln Pro Pro Glu
            260                 265                 270

Met Gln Gln Pro Ala Asp Arg Ser Asp Glu Arg Gly Gly Lys Glu
        275                 280                 285

Gln Ser Pro Gly Gly Glu Ala Gln Pro Asp His Pro Thr Lys Gly Gly
    290                 295                 300

Asn Ile Asp Leu Pro Glu Lys Ser Thr Ser Pro Glu Lys Thr Pro Lys
305                 310                 315                 320
```

```
Thr Glu Ile His Gly Asp Ser Thr Lys Ala Thr Leu Glu Glu Gly Gln
                325                 330                 335

Gln Leu Thr Leu Thr Phe Ile Ser Thr Lys Leu Asp Val Ala Val Gly
            340                 345                 350

Ser Cys His Ser Leu Val Ala Asn Phe Leu Asp Gly Phe Leu Lys Phe
            355                 360                 365

Gln Thr Gly Ser Asn Ser Ala Phe Asp Val Val Glu Val Glu Glu Pro
        370                 375                 380

Ala Gly Pro Ala Val Leu Thr Ile Gly Leu His Lys Gly Arg Leu
385                 390                 395                 400

Ala Val Val Leu Asp Tyr Thr Arg Leu Asn Ala Ala Leu Gly Ser Ala
                405                 410                 415

Ala Tyr Val Val Glu Asp Ser Gly Cys Ser Ser Ser Glu Glu Val Ser
                420                 425                 430

Phe Gln Gly Val Gly Ser Gly Ala Thr Leu Val Val Thr Thr Leu Gly
            435                 440                 445

Glu Ser Pro Thr Ala Val Ser Ala
        450                 455

<210> SEQ ID NO 2
<211> LENGTH: 321
<212> TYPE: PRT
<213> ORGANISM: Toxopolasmosis gondii

<400> SEQUENCE: 2

Met Ala Tyr Gly Glu Ala Ser His Ser His Ser Pro Ala Ser Gly Arg
1               5                   10                  15

Tyr Ile Gln Gln Met Leu Asp Gln Arg Cys Gln Glu Ile Ala Ala Glu
            20                  25                  30

Leu Cys Gln Gly Gly Leu Arg Lys Met Cys Val Pro Ser Ser Arg Ile
        35                  40                  45

Val Ala Arg Asn Ala Val Gly Ile Thr His Gln Asn Thr Leu Glu Trp
    50                  55                  60

Arg Cys Phe Asp Thr Ala Ser Leu Leu Glu Ser Asn Gln Glu Asn Asn
65                  70                  75                  80

Gly Val Asn Cys Val Asp Asp Cys Gly His Thr Ile Pro Cys Pro Gly
                85                  90                  95

Gly Val His Arg Gln Asn Ser Asn His Ala Thr Arg His Glu Ile Leu
            100                 105                 110

Ser Lys Leu Val Glu Glu Gly Val Gln Arg Phe Cys Ser Pro Tyr Gln
        115                 120                 125

Ala Ser Ala Asn Lys Tyr Cys Asn Asp Lys Phe Pro Gly Thr Ile Ala
    130                 135                 140

Arg Arg Ser Lys Gly Phe Gly Asn Asn Val Glu Val Ala Trp Arg Cys
145                 150                 155                 160

Tyr Glu Lys Ala Ser Leu Leu Tyr Ser Val Tyr Ala Glu Cys Ala Ser
                165                 170                 175

Asn Cys Gly Thr Thr Trp Tyr Cys Pro Gly Gly Arg Arg Gly Thr Ser
            180                 185                 190

Thr Glu Leu Asp Lys Arg His Tyr Thr Glu Glu Gly Ile Arg Gln
        195                 200                 205

Ala Ile Gly Ser Val Asp Ser Pro Cys Ser Glu Val Glu Val Cys Leu
    210                 215                 220

Pro Lys Asp Glu Asn Pro Pro Val Cys Leu Asp Glu Ser Gly Gln Ile
225                 230                 235                 240
```

```
Ser Arg Thr Gly Gly Gly Pro Pro Ser Gln Pro Pro Glu Met Gln Gln
                245                 250                 255

Pro Ala Asp Arg Ser Asp Glu Arg Gly Gly Lys Glu Gln Ser Pro
            260                 265                 270

Gly Gly Glu Ala Gln Pro Asp His Pro Thr Lys Gly Gly Asn Ile Asp
        275                 280                 285

Leu Pro Glu Lys Ser Thr Ser Pro Glu Lys Thr Pro Lys Thr Glu Ile
    290                 295                 300

His Gly Asp Ser Thr Lys Ala Thr Leu Glu Glu Gly Gln Gln Leu Thr
305                 310                 315                 320

Leu

<210> SEQ ID NO 3
<211> LENGTH: 1920
<212> TYPE: DNA
<213> ORGANISM: Toxopolasmosis gondii

<400> SEQUENCE: 3
acctgaaagc gggtgccgcg tcgctaccgt ttcctgtggc gtctctagtg cgacatccga    60
agtaacagta acgtccggca tggaacgccg acgcgggtgt tccagtcgcc tggctccttc   120
tactcgcact tcgatgttac gttccttatt ggtgcgacgc ggttctcgtg ttgctagacg   180
tcgcaccggc tgaaagctgt agaaaattta gttattttcc tgtcagctag cttgcaggag   240 tgcgttttg tgtgttggtt tcgtctcaca tggctgctga tctgttgatg cagctgtgta    300
cacgtgcctc gattctgtag ttgacctaga acggatttgc aaagatgggc caggcgttgt   360
ttctcaccgt tctattgccg gtgttatttg gcgttgggcc agaagcatat ggagaagcgt   420
cgcattctca ttcgccggca tcgggacgtt atatacaaca gatgcttgac caacgctgcc   480
aagagattgc tgcagaactc tgccaaggcg gacttcgtaa aatgtgtgtg ccctctagcc   540
ggatagtagc tcgaaacgcc gtgggcatta ctcatcaaaa tacacttgaa tggagatgct   600
ttgatacagc ctctttgctg gagagcaatc aagaaaacaa cggtgttaat tgcgtggacg   660
actgtggcca cacgataccg tgtcctggcg gcgtacaccg gcaaaacagt aatcacgcaa   720
cgcgccatga gatactgtcc aaattggtcg aagaaggagt acaacggttc tgcagtcctt   780
atcaagcatc tgccaacaag tactgtaacg acaaatttcc agggaccatt gcgaggaggt   840
cgaagggctt cggaaacaat gtcgaggttg cgtggaggtg ttacgagaag ccagcttgc    900 tgtactcggt ttatgctgag tgtgcgagca actgcggaac aacgtggtac tgccctggag   960
gacgacgagg gacgtcgaca gaactagaca agcggcatta tacagaagag gaaggaattc  1020
gccaggcaat cggatccgtc gacagcccat gttctgaagt tgaagtctgc ctaccgaagg  1080
atgagaatcc cccggtgtgt ttagatgaaa gtggccagat ttcacgaact ggtggtgggc  1140
caccgtcaca accgcctgag atgcaacagc ccgccgatcg ttcggacgag agaggtggcg  1200
gtaaggaaca gtcgcctgga ggagaagctc agccggacca tccaacgaag ggtggtaaca  1260
tagacctgcc tgagaaatca acatctcccg agaagacgcc gaaaaccgag atccatggtg  1320
acagcacgaa agcgacgctc gaagaggggc agcaactaac gctcacgttt atctccacta  1380
aactggatgt tgctgtaggc tcgtgtcatt cactcgtcgc gaatttcctt gatggatttt  1440
tgaagtttca gacgggctca aattcggcgt tcgatgtggt agaagtggaa gagccagcag  1500
gacccgcagt gcttacgata ggtctgggac acaaaggccg tctcgctgtt gtcctcgact  1560
acaccaggct caatgctgct ttaggatcag ctgcttacgt ggtcgaagat tctggatgca  1620
```

-continued

```
gctcaagtga agaggttagt ttccaaggag tgggtagtgg agcgacgctc gtggtgacga    1680
cgcttggcga gagtcctacg gccgtctctg cttgatttat agtactcttt ggagcatgct    1740
tgtggaggaa cgggacaatc tcggcaaaat caggatgaag tttgtgagat acagatcgtt    1800
cctgaacagt ggaagatgcg tcactattac acctatatgc gtcctggttc ttgtagagtt    1860
ggagttcttg caggtgtaat gactatgaca tacggatata acttcatacg gggaactgtg    1920
```

<210> SEQ ID NO 4
<211> LENGTH: 48
<212> TYPE: DNA
<213> ORGANISM: Toxopolasmosis gondii

<400> SEQUENCE: 4

```
actgtggtct ctaggtatgg aagcatatgg agaagcgtcg cattctca                   48
```

<210> SEQ ID NO 5
<211> LENGTH: 49
<212> TYPE: DNA
<213> ORGANISM: Toxopolasmosis gondii

<400> SEQUENCE: 5

```
actgttctag atcagagcgt tagttgctgc ccctcttcga gcgtcgctt                  49
```

<210> SEQ ID NO 6
<211> LENGTH: 198
<212> TYPE: PRT
<213> ORGANISM: Toxopolasmosis gondii

<400> SEQUENCE: 6

```
Met Ala Leu Ser Ser Leu Asn Asn Ile Arg Pro Phe Ser Gly Leu Leu
1               5                   10                  15

Gly Cys Gly Leu Leu Phe Gly Ala Leu Val Val Val Ala Cys Val
            20                  25                  30

Phe Ser Val Pro Val Glu Ala Gly Val Leu Arg Lys Val Ala Gly Ala
        35                  40                  45

Gly Ser Leu Gln Ala Ser Ile Gly Glu His Asp Phe Phe Asn Asp Tyr
    50                  55                  60

Asp Gln Asp Glu Glu Tyr Arg Lys Arg Gln Gln Glu Leu Gln Asn Gln
65                  70                  75                  80

Ser Pro Glu Glu Val Glu Ala Lys Arg Lys Tyr His Glu Glu Leu
                85                  90                  95

Arg Arg Lys Ala Glu Glu Asp Ala Glu Thr Lys Arg Lys Gln Glu Ala
            100                 105                 110

Val Ile Gln Glu Leu Lys Glu Val Ala Lys Lys Arg Gly Leu Arg Glu
        115                 120                 125

Ala Ala Glu Arg Glu Glu Lys Arg Ile Asp Glu Gln Gln Ala Asn Tyr
    130                 135                 140

Glu Gln Arg Gln Gln Glu Leu Arg Asp Met Asp Ser Ala Met Glu Glu
145                 150                 155                 160

Arg Leu Met Gln Gln Arg Lys Lys Asp Gln Glu Glu Arg Glu Leu Ala
                165                 170                 175

Arg Lys Asn Ser Asp Lys Val Met Glu Glu Leu Lys Glu Lys Leu Ala
            180                 185                 190

Arg Arg Arg Lys Ser Met
        195
```

<210> SEQ ID NO 7
<211> LENGTH: 198
<212> TYPE: PRT
<213> ORGANISM: Toxopolasmosis gondii

<400> SEQUENCE: 7

Met Ala Leu Ser Ser Leu Asn Asn Ile Arg Pro Phe Ser Gly Leu Leu
1               5                   10                  15

Gly Cys Gly Leu Leu Phe Gly Ala Leu Val Val Val Ala Cys Val
            20                  25                  30

Phe Ser Val Pro Val Glu Ala Gly Val Leu Arg Lys Val Ala Gly Ala
            35                  40                  45

Gly Ser Leu Gln Ala Ser Ile Gly Glu His Asp Phe Phe Asn Asp Tyr
        50                  55                  60

Asp Gln Asp Glu Glu Tyr Arg Lys Arg Gln Gln Glu Leu Gln Asn Gln
65                  70                  75                  80

Ser Pro Glu Glu Val Glu Glu Ala Lys Arg Lys Tyr His Glu Glu Leu
                85                  90                  95

Arg Arg Lys Ala Glu Glu Asp Ala Glu Thr Lys Arg Lys Gln Glu Ala
            100                 105                 110

Val Ile Gln Glu Leu Lys Glu Val Ala Lys Lys Arg Gly Leu Arg Glu
        115                 120                 125

Ala Ala Glu Arg Glu Glu Lys Arg Ile Asp Glu Gln Gln Ala Asn Tyr
    130                 135                 140

Glu Gln Arg Gln Gln Glu Leu Arg Asp Met Asp Ser Ala Met Glu Glu
145                 150                 155                 160

Arg Leu Met Gln Gln Arg Lys Lys Asp Gln Glu Glu Arg Glu Leu Ala
                165                 170                 175

Arg Lys Asn Ser Asp Lys Val Met Glu Glu Leu Lys Glu Lys Leu Ala
            180                 185                 190

Arg Arg Arg Lys Ser Met
        195

<210> SEQ ID NO 8
<211> LENGTH: 960
<212> TYPE: DNA
<213> ORGANISM: Toxopolasmosis gondii

<400> SEQUENCE: 8
ttgtcggata gaacacatca aaatttttt ctgtttcatc tgtcacgtgc gtcctttgg      60 tggaagcgac gcgtcgtcgc ggccctgttg ggggtagtca atatttcagt aagcgtttct   120
agcgacaccc gctacacaga acactcggtt gaagcactgt gatgctggcg tttctgtccg   180
ctgtctttct gcagaatggc gctttcttct tgaacaata tcaggccttt tagcgggttg   240
ctgggttgcg gcctgctgtt tggcgccctt gtggtcgtgg tggcatgtgt tttcagcgtt   300
cctgtggaag caggcgttct tcgtaaggta gcaggtgcag gaagtctcca ggcgtctatt   360
ggagagcacg attttttaa cgattacgat caggacgagg aatacaggaa gcgccagcaa   420
gaactgcaga atcagagtcc agaagaagtc gaggaagcga acgcaaata ccacgaagag   480 ctgagacgga aagcagaaga agatgcagag acgaaacgta agcaagaagc agtcattcaa   540
gaactgaaag aggtggcaaa gaaaagagga cttcgtgaag ccgctgagcg tgaggagaag   600
cgcattgatg agcagcaggc taattacgag caacgacaac aagaactgag agacatggat   660
tcagcaatgg aggagaggct tatgcagcag agaaaaaaag accaggaaga gagagaactt   720
gcaagaaaaa acagcgataa ggtcatggag gagctcaaag agaaactcgc aagacgcagg   780

```
aaatcaatgt agaagaaagg caagttctga ctagtgtatg aagtgtagca gcggtccgtt    840
attaccgtgt atacagggag atcgtcgttc agtttgaagt gtttattccg tgttgaaaga    900
agcgtttgtg taatgcagat gatcctgaga tgatagtgcg ggaaatcgaa tgactcattg    960
```

<210> SEQ ID NO 9
<211> LENGTH: 41
<212> TYPE: DNA
<213> ORGANISM: Toxopolasmosis gondii

<400> SEQUENCE: 9

```
actgtggtct ctaggtatgg cgctttcttc tttgaacaat a                         41
```

<210> SEQ ID NO 10
<211> LENGTH: 38
<212> TYPE: DNA
<213> ORGANISM: Toxopolasmosis gondii

<400> SEQUENCE: 10

```
actgttctag atcacattga tttcctgcgt cttgcgag                             38
```

<210> SEQ ID NO 11
<211> LENGTH: 236
<212> TYPE: PRT
<213> ORGANISM: Toxopolasmosis gondii

<400> SEQUENCE: 11

Met Ala Arg His Ala Ile Phe Phe Ala Leu Cys Val Leu Gly Leu Val
1               5                   10                  15

Ala Ala Ala Leu Pro Gln Phe Ala Thr Ala Ala Thr Ala Ser Asp Asp
                20                  25                  30

Glu Leu Met Ser Arg Ile Arg Asn Ser Asp Phe Asp Gly Gln Ala
            35                  40                  45

Pro Val Asp Ser Leu Arg Pro Thr Asn Ala Gly Val Asp Ser Lys Gly
        50                  55                  60

Thr Asp Asp His Leu Thr Thr Ser Met Asp Lys Ala Ser Val Glu Ser
65                  70                  75                  80

Gln Leu Pro Arg Arg Glu Pro Leu Glu Thr Glu Pro Asp Glu Gln Glu
                85                  90                  95

Glu Val His Phe Arg Lys Arg Gly Val Arg Ser Asp Ala Glu Val Thr
            100                 105                 110

Asp Asp Asn Ile Tyr Glu Glu His Thr Asp Arg Lys Val Val Pro Arg
        115                 120                 125

Lys Ser Glu Gly Lys Arg Ser Phe Lys Asp Leu Leu Lys Lys Leu Ala
    130                 135                 140

Leu Pro Ala Val Gly Met Gly Ala Ser Tyr Phe Ala Ala Asp Arg Ile
145                 150                 155                 160

Leu Pro Glu Leu Thr Glu Gln Gln Gln Thr Gly Glu Glu Pro Leu Thr
                165                 170                 175

Thr Gly Gln Asn Val Ser Thr Val Leu Gly Phe Ala Ala Leu Ala Ala
            180                 185                 190

Ala Ala Ala Phe Leu Gly Met Gly Leu Thr Arg Thr Tyr Arg His Phe
        195                 200                 205

Ser Pro Arg Lys Asn Arg Ser Arg Gln Pro Ala Leu Glu Gln Glu Val
    210                 215                 220

Pro Glu Ser Gly Lys Asp Gly Glu Asp Ala Arg Gln
225                 230                 235

<210> SEQ ID NO 12
<211> LENGTH: 236
<212> TYPE: PRT
<213> ORGANISM: Toxopolasmosis gondii

<400> SEQUENCE: 12

```
Met Ala Arg His Ala Ile Phe Phe Ala Leu Cys Val Leu Gly Leu Val
1               5                   10                  15

Ala Ala Ala Leu Pro Gln Phe Ala Thr Ala Ala Thr Ala Ser Asp Asp
            20                  25                  30

Glu Leu Met Ser Arg Ile Arg Asn Ser Asp Phe Phe Asp Gly Gln Ala
        35                  40                  45

Pro Val Asp Ser Leu Arg Pro Thr Asn Ala Gly Val Asp Ser Lys Gly
    50                  55                  60

Thr Asp Asp His Leu Thr Thr Ser Met Asp Lys Ala Ser Val Glu Ser
65                  70                  75                  80

Gln Leu Pro Arg Arg Glu Pro Leu Glu Thr Glu Pro Asp Glu Gln Glu
                85                  90                  95

Glu Val His Phe Arg Lys Arg Gly Val Arg Ser Asp Ala Glu Val Thr
            100                 105                 110

Asp Asp Asn Ile Tyr Glu Glu His Thr Asp Arg Lys Val Val Pro Arg
        115                 120                 125

Lys Ser Glu Gly Lys Arg Ser Phe Lys Asp Leu Leu Lys Lys Leu Ala
    130                 135                 140

Leu Pro Ala Val Gly Met Gly Ala Ser Tyr Phe Ala Ala Asp Arg Ile
145                 150                 155                 160

Leu Pro Glu Leu Thr Glu Gln Gln Gln Thr Gly Glu Glu Pro Leu Thr
                165                 170                 175

Thr Gly Gln Asn Val Ser Thr Val Leu Gly Phe Ala Ala Leu Ala Ala
            180                 185                 190

Ala Ala Ala Phe Leu Gly Met Gly Leu Thr Arg Thr Tyr Arg His Phe
        195                 200                 205

Ser Pro Arg Lys Asn Arg Ser Arg Gln Pro Ala Leu Glu Gln Glu Val
    210                 215                 220

Pro Glu Ser Gly Lys Asp Gly Glu Asp Ala Arg Gln
225                 230                 235
```

<210> SEQ ID NO 13
<211> LENGTH: 1120
<212> TYPE: DNA
<213> ORGANISM: Toxopolasmosis gondii

<400> SEQUENCE: 13

```
ttactttctt cggattacat tcttccacta aaagctggtt ttgtccagta tccattcgtc      60
gctaccgttg cgcagtcacg ttgaattttg cagcggcaaa acatcttgtg taaaattcga     120
gttttgttga tgattgaagt accctgtatt ggggcttgct aacgttttgt attaaaaggg     180
tttactgcgg cgtctcattt ccaaaatggc ccgacacgca attttttttcg cgctttgtgt     240 tttaggcctg gtggcggcgg ctttgcccca gttcgctacc gcggccaccg cgtcagatga     300
cgaactgatg agtcgaatcc gaaattctga cttttttcgat ggtcaagcac ccgttgacag     360
tctcagaccg acgaacgccg gtgtcgactc gaaagggacc gacgatcacc tcaccaccag     420
catggataag gcatctgtag agagtcagct tccgagaaga gagccattgg agacggagcc     480
agatgaacaa gaagaagttc atttcaggaa gcgaggcgtc cgttccgacg ctgaagtgac     540
```

```
tgacgacaac atctacgagg agcacactga tcgtaaagtg gttccgagga agtcggaggg      600
caagcgaagc ttcaaagact tgctgaagaa gctcgcgctg ccggctgttg gtatgggtgc      660
atcgtatttt gccgctgata gaattctgcc ggaactaaca gagcagcaac agacaggcga      720 agaacccta accaccggcc agaatgtgag cactgtgtta ggcttcgcag cgcttgctgc       780
tgccgcagcg ttccttggca tgggtctcac gaggacgtac cgacattttt ccccacgcaa      840
aaacagatca cggcagcctg cactcgagca agaggtgcct gaatcaggca agatggggga      900
ggatgcccgc cagtaggata tggggctaa taaaagtgag taggagctcg aggacagtgt       960
cccgaacgcg cctgagaggc agacagacac agaaagtga agaaaaacaa catggtatta     1020
cgtgcggtga gtgtttgctg tcacgtgttt tttgcgccac aaagacagct tgtgttgtat    1080
gcatgggatc gacagttcat ggacggcgct acccagagag                           1120
```

<210> SEQ ID NO 14
<211> LENGTH: 37
<212> TYPE: DNA
<213> ORGANISM: Toxopolasmosis gondii

<400> SEQUENCE: 14

```
actgtgagga ctcaggtatg gctttgcccc agttcgc                                37
```

<210> SEQ ID NO 15
<211> LENGTH: 35
<212> TYPE: DNA
<213> ORGANISM: Toxopolasmosis gondii

<400> SEQUENCE: 15

```
actgttctag atcactggcg ggcatcctcc ccatc                                  35
```

<210> SEQ ID NO 16
<211> LENGTH: 324
<212> TYPE: DNA
<213> ORGANISM: Toxopolasmosis gondii

<400> SEQUENCE: 16

```
atgggtcatc accatcatca tcacgggtcc ctgcaggact cagaagtcaa tcaagaagct       60
aagccagagg tcaagccaga agtcaagcct gagactcaca tcaatttaaa ggtgtccgat      120
ggatcttcag agatcttctt caagatcaaa aagaccactc ctttaagaag gctgatggaa      180
gcgttcgcta aagacaggg taaggaaatg gactccttaa gattcttgta cgacggtatt      240
agaattcaag ctgatcaggc ccctgaagat ttggacatgg aggataacga tattattgag      300
gctcaccgcg aacagattgg aggt                                              324
```

<210> SEQ ID NO 17
<211> LENGTH: 108
<212> TYPE: PRT
<213> ORGANISM: Toxopolasmosis gondii

<400> SEQUENCE: 17

```
Met Gly His His His His His His Gly Ser Leu Gln Asp Ser Glu Val
1               5                   10                  15

Asn Gln Glu Ala Lys Pro Glu Val Lys Pro Glu Val Lys Pro Glu Thr
            20                  25                  30

His Ile Asn Leu Lys Val Ser Asp Gly Ser Ser Glu Ile Phe Phe Lys
        35                  40                  45

Ile Lys Lys Thr Thr Pro Leu Arg Arg Leu Met Glu Ala Phe Ala Lys
```

Arg Gln Gly Lys Glu Met Asp Ser Leu Arg Phe Leu Tyr Asp Gly Ile
65                  70                  75                  80

Arg Ile Gln Ala Asp Gln Ala Pro Glu Asp Leu Asp Met Glu Asp Asn
                85                  90                  95

Asp Ile Ile Glu Ala His Arg Glu Gln Ile Gly Gly
            100                 105

<210> SEQ ID NO 18
<211> LENGTH: 456
<212> TYPE: PRT
<213> ORGANISM: Toxopolasmosis gondii

<400> SEQUENCE: 18

Met Gly Gln Ala Leu Phe Leu Thr Val Leu Pro Val Leu Phe Gly
1               5                   10                  15

Val Gly Pro Glu Ala Tyr Gly Glu Ala Ser His Ser His Ser Pro Ala
                20                  25                  30

Ser Gly Arg Tyr Ile Gln Gln Met Leu Asp Gln Arg Cys Gln Glu Ile
            35                  40                  45

Ala Ala Glu Leu Cys Gln Gly Gly Leu Arg Lys Met Cys Val Pro Ser
50                  55                  60

Ser Arg Ile Val Ala Arg Asn Ala Val Gly Ile Thr His Gln Asn Thr
65                  70                  75                  80

Leu Glu Trp Arg Cys Phe Asp Thr Ala Ser Leu Leu Glu Ser Asn Gln
                85                  90                  95

Glu Asn Asn Gly Val Asn Cys Val Asp Cys Gly His Thr Ile Pro
            100                 105                 110

Cys Pro Gly Gly Val His Arg Gln Asn Ser Asn His Ala Thr Arg His
        115                 120                 125

Glu Ile Leu Ser Lys Leu Val Glu Glu Gly Val Gln Arg Phe Cys Ser
    130                 135                 140

Pro Tyr Gln Ala Ser Ala Asn Lys Tyr Cys Asn Asp Lys Phe Pro Gly
145                 150                 155                 160

Thr Ile Ala Arg Arg Ser Lys Gly Phe Gly Asn Asn Val Glu Val Ala
                165                 170                 175

Trp Arg Cys Tyr Glu Lys Ala Ser Leu Leu Tyr Ser Val Tyr Ala Glu
            180                 185                 190

Cys Ala Ser Asn Cys Gly Thr Thr Trp Tyr Cys Pro Gly Gly Arg Arg
        195                 200                 205

Gly Thr Ser Thr Glu Leu Asp Lys Arg His Tyr Thr Glu Glu Glu Gly
    210                 215                 220

Ile Arg Gln Ala Ile Gly Ser Val Asp Ser Pro Cys Ser Glu Val Glu
225                 230                 235                 240

Val Cys Leu Pro Lys Asp Glu Asn Pro Pro Val Cys Leu Asp Glu Ser
                245                 250                 255

Gly Gln Ile Ser Arg Thr Gly Gly Pro Ser Gln Pro Glu
            260                 265                 270

Met Gln Gln Pro Ala Asp Arg Ser Asp Glu Arg Gly Gly Lys Glu
        275                 280                 285

Gln Ser Pro Gly Gly Glu Ala Gln Pro Asp His Pro Thr Lys Gly Gly
    290                 295                 300

Asn Ile Asp Leu Pro Glu Lys Ser Thr Ser Pro Glu Lys Thr Pro Lys
305                 310                 315                 320

-continued

```
Thr Glu Ile His Gly Asp Ser Thr Lys Ala Thr Leu Glu Glu Gly Gln
            325                 330                 335

Gln Leu Thr Leu Thr Phe Ile Ser Thr Lys Leu Asp Val Ala Val Gly
            340                 345                 350

Ser Cys His Ser Leu Val Ala Asn Phe Leu Asp Gly Phe Leu Lys Phe
            355                 360                 365

Gln Thr Gly Ser Asn Ser Ala Phe Asp Val Val Glu Val Glu Glu Pro
            370                 375                 380

Ala Gly Pro Ala Val Leu Thr Ile Gly Leu Gly His Lys Gly Arg Leu
385                 390                 395                 400

Ala Val Val Leu Asp Tyr Thr Arg Leu Asn Ala Ala Leu Gly Ser Ala
                405                 410                 415

Ala Tyr Val Val Glu Asp Ser Gly Cys Ser Ser Ser Glu Glu Val Ser
                420                 425                 430

Phe Gln Gly Val Gly Ser Gly Ala Thr Leu Val Val Thr Thr Leu Gly
            435                 440                 445

Glu Ser Pro Thr Ala Val Ser Ala
            450                 455

<210> SEQ ID NO 19
<211> LENGTH: 456
<212> TYPE: PRT
<213> ORGANISM: Toxopolasmosis gondii

<400> SEQUENCE: 19

Met Gly Gln Ala Leu Phe Leu Thr Val Leu Pro Val Leu Phe Gly
1               5                   10                  15

Val Gly Pro Glu Ala Tyr Gly Glu Ala Ser His Ser His Ser Pro Ala
            20                  25                  30

Ser Gly Arg Tyr Ile Gln Gln Met Leu Asp Gln Arg Cys Gln Glu Ile
            35                  40                  45

Ala Ala Glu Leu Cys Gln Gly Gly Leu Arg Lys Met Cys Val Pro Ser
            50                  55                  60

Ser Arg Ile Val Ala Arg Asn Ala Val Gly Ile Thr His Gln Asn Thr
65                  70                  75                  80

Leu Glu Trp Arg Cys Phe Asp Thr Ala Ser Leu Leu Glu Ser Asn Gln
            85                  90                  95

Glu Asn Asn Gly Val Asn Cys Val Asp Asp Cys Gly His Thr Ile Pro
            100                 105                 110

Cys Pro Gly Gly Val His Arg Gln Asn Ser Asn His Ala Thr Arg His
            115                 120                 125

Glu Ile Leu Ser Lys Leu Val Glu Glu Gly Val Gln Arg Phe Cys Ser
            130                 135                 140

Pro Tyr Gln Ala Ser Ala Asn Lys Tyr Cys Asn Asp Lys Phe Pro Gly
145                 150                 155                 160

Thr Ile Ala Arg Arg Ser Lys Gly Phe Gly Asn Asn Val Glu Val Ala
                165                 170                 175

Trp Arg Cys Tyr Glu Lys Ala Ser Leu Leu Tyr Ser Val Tyr Ala Glu
                180                 185                 190

Cys Ala Ser Asn Cys Gly Thr Thr Trp Tyr Cys Pro Gly Gly Arg Arg
            195                 200                 205

Gly Thr Ser Thr Glu Leu Asp Lys Arg His Tyr Thr Glu Glu Glu Gly
            210                 215                 220

Ile Arg Gln Ala Ile Gly Ser Val Asp Ser Pro Cys Ser Glu Val Glu
225                 230                 235                 240
```

Val Cys Leu Pro Lys Asp Glu Asn Pro Pro Val Cys Leu Asp Glu Ser
            245                 250                 255

Gly Gln Ile Ser Arg Thr Gly Gly Pro Pro Ser Gln Pro Pro Glu
        260                 265                 270

Met Gln Gln Pro Ala Asp Arg Ser Asp Glu Arg Gly Gly Lys Glu
            275                 280                 285

Gln Ser Pro Gly Gly Glu Ala Gln Pro Asp His Pro Thr Lys Gly Gly
        290                 295                 300

Asn Ile Asp Leu Pro Glu Lys Ser Thr Ser Pro Glu Lys Thr Pro Lys
305                 310                 315                 320

Thr Glu Ile His Gly Asp Ser Thr Lys Ala Thr Leu Glu Glu Gly Gln
                325                 330                 335

Gln Leu Thr Leu Thr Phe Ile Ser Thr Lys Leu Asp Val Ala Val Gly
            340                 345                 350

Ser Cys His Ser Leu Val Ala Asn Phe Leu Asp Gly Phe Leu Lys Phe
            355                 360                 365

Gln Thr Gly Ser Asn Ser Ala Phe Asp Val Val Glu Val Glu Glu Pro
    370                 375                 380

Ala Gly Pro Ala Val Leu Thr Ile Gly Leu Gly His Lys Gly Arg Leu
385                 390                 395                 400

Ala Val Val Leu Asp Tyr Thr Arg Leu Asn Ala Ala Leu Gly Ser Ala
                405                 410                 415

Ala Tyr Val Val Glu Asp Ser Gly Cys Ser Ser Ser Glu Glu Val Ser
            420                 425                 430

Phe Gln Gly Val Gly Ser Gly Ala Thr Leu Val Val Thr Thr Leu Gly
            435                 440                 445

Glu Ser Pro Thr Ala Val Ser Ala
    450                 455

<210> SEQ ID NO 20
<211> LENGTH: 456
<212> TYPE: PRT
<213> ORGANISM: Toxopolasmosis gondii

<400> SEQUENCE: 20

Met Gly Gln Ala Leu Phe Leu Thr Val Leu Pro Val Leu Phe Gly
1               5                   10                  15

Val Gly Pro Glu Ala Tyr Gly Glu Ala Ser His Ser His Ser Pro Ala
            20                  25                  30

Ser Gly Arg Tyr Ile Gln Gln Met Leu Asp Gln Arg Cys Gln Glu Ile
        35                  40                  45

Ala Ala Glu Leu Cys Gln Gly Gly Leu Arg Lys Met Cys Val Pro Ser
    50                  55                  60

Ser Arg Ile Val Ala Arg Asn Ala Val Gly Ile Thr His Gln Asn Thr
65                  70                  75                  80

Leu Glu Trp Arg Cys Phe Asp Thr Ala Ser Leu Leu Glu Ser Asn Gln
                85                  90                  95

Glu Asn Asn Gly Val Asn Cys Val Asp Asp Cys Gly His Thr Ile Pro
            100                 105                 110

Cys Pro Gly Gly Val His Arg Gln Asn Ser Asn His Ala Thr Arg His
        115                 120                 125

Glu Ile Leu Ser Lys Leu Val Glu Glu Gly Val Gln Arg Phe Cys Ser
    130                 135                 140

Pro Tyr Gln Ala Ser Ala Asn Lys Tyr Cys Asn Asp Lys Phe Pro Gly

```
                145                 150                 155                 160
        Thr Ile Ala Arg Arg Ser Lys Gly Phe Gly Asn Asn Val Glu Val Ala
                        165                 170                 175
        Trp Arg Cys Tyr Glu Lys Ala Ser Leu Leu Tyr Ser Val Tyr Ala Glu
                        180                 185                 190
        Cys Ala Ser Asn Cys Gly Thr Thr Trp Tyr Cys Pro Gly Gly Arg Arg
                        195                 200                 205
        Gly Thr Ser Thr Glu Leu Asp Lys Arg His Tyr Thr Glu Glu Glu Gly
                        210                 215                 220
        Ile Arg Gln Ala Ile Gly Ser Val Asp Ser Pro Cys Ser Glu Val Glu
        225                 230                 235                 240
        Val Cys Leu Pro Lys Asp Glu Asn Pro Pro Val Cys Leu Asp Glu Ser
                        245                 250                 255
        Gly Gln Ile Ser Arg Thr Gly Gly Pro Pro Ser Gln Pro Pro Glu
                        260                 265                 270
        Met Gln Gln Pro Ala Asp Arg Ser Asp Glu Arg Gly Gly Gly Lys Glu
                        275                 280                 285
        Gln Ser Pro Gly Gly Glu Ala Gln Pro Asp His Pro Thr Lys Gly Gly
                        290                 295                 300
        Asn Ile Asp Leu Pro Glu Lys Ser Thr Ser Pro Glu Lys Thr Pro Lys
        305                 310                 315                 320
        Thr Glu Ile His Gly Asp Ser Thr Lys Ala Thr Leu Glu Glu Gly Gln
                        325                 330                 335
        Gln Leu Thr Leu Thr Phe Ile Ser Thr Lys Leu Asp Val Ala Val Gly
                        340                 345                 350
        Ser Cys His Ser Leu Val Ala Asn Phe Leu Asp Gly Phe Leu Lys Phe
                        355                 360                 365
        Gln Thr Gly Ser Asn Ser Ala Phe Asp Val Val Glu Val Glu Glu Pro
                        370                 375                 380
        Ala Gly Pro Ala Val Leu Thr Ile Gly Leu Gly His Lys Gly Arg Leu
        385                 390                 395                 400
        Ala Val Val Leu Asp Tyr Thr Arg Leu Asn Ala Ala Leu Gly Ser Ala
                        405                 410                 415
        Ala Tyr Val Val Glu Asp Ser Gly Cys Ser Ser Ser Glu Glu Val Ser
                        420                 425                 430
        Phe Gln Gly Val Gly Ser Gly Ala Thr Leu Val Val Thr Thr Leu Gly
                        435                 440                 445
        Glu Ser Pro Thr Ala Val Ser Ala
                        450                 455

<210> SEQ ID NO 21
<211> LENGTH: 456
<212> TYPE: PRT
<213> ORGANISM: Toxopolasmosis gondii

<400> SEQUENCE: 21

Met Gly Gln Ala Leu Phe Leu Thr Val Leu Leu Pro Val Leu Phe Gly
1               5                   10                  15

Val Gly Pro Glu Ala Tyr Gly Glu Ala Ser His Ser His Ser Pro Ala
                20                  25                  30

Ser Gly Arg Tyr Ile Gln Gln Met Leu Asp Gln Arg Cys Gln Glu Ile
                35                  40                  45

Ala Ala Glu Leu Cys Gln Gly Gly Leu Arg Lys Met Cys Val Pro Ser
                50                  55                  60
```

```
Ser Arg Ile Val Ala Arg Asn Ala Val Gly Ile Thr His Gln Asn Thr
 65                  70                  75                  80

Leu Glu Trp Arg Cys Phe Asp Thr Ala Ser Leu Leu Glu Ser Asn Gln
                 85                  90                  95

Glu Asn Asn Gly Val Asn Cys Val Asp Asp Cys Gly His Thr Ile Pro
            100                 105                 110

Cys Pro Gly Gly Val His Arg Gln Asn Ser Asn His Ala Thr Arg His
        115                 120                 125

Glu Ile Leu Ser Lys Leu Val Glu Glu Gly Val Gln Arg Phe Cys Ser
130                 135                 140

Pro Tyr Gln Ala Ser Ala Asn Lys Tyr Cys Asn Asp Lys Phe Pro Gly
145                 150                 155                 160

Thr Ile Ala Arg Arg Ser Lys Gly Phe Gly Asn Asn Val Glu Val Ala
                165                 170                 175

Trp Arg Cys Tyr Glu Lys Ala Ser Leu Leu Tyr Ser Val Tyr Ala Glu
            180                 185                 190

Cys Ala Ser Asn Cys Gly Thr Thr Trp Tyr Cys Pro Gly Gly Arg Arg
        195                 200                 205

Gly Thr Ser Thr Glu Leu Asp Lys Arg His Tyr Thr Glu Glu Glu Gly
210                 215                 220

Ile Arg Gln Ala Ile Gly Ser Val Asp Ser Pro Cys Ser Glu Val Glu
225                 230                 235                 240

Val Cys Leu Pro Lys Asp Glu Asn Pro Val Cys Leu Asp Glu Ser
                245                 250                 255

Gly Gln Ile Ser Arg Thr Gly Gly Pro Ser Gln Pro Pro Glu
            260                 265                 270

Met Gln Gln Pro Ala Asp Arg Ser Asp Glu Arg Gly Gly Lys Glu
        275                 280                 285

Gln Ser Pro Gly Gly Glu Ala Gln Pro Asp His Pro Thr Lys Gly Gly
290                 295                 300

Asn Ile Asp Leu Pro Glu Lys Ser Thr Ser Pro Glu Lys Thr Pro Lys
305                 310                 315                 320

Thr Glu Ile His Gly Asp Ser Thr Lys Ala Thr Leu Glu Gly Gln
                325                 330                 335

Gln Leu Thr Leu Thr Phe Ile Ser Thr Lys Leu Asp Val Ala Val Gly
            340                 345                 350

Ser Cys His Ser Leu Val Ala Asn Phe Leu Asp Gly Phe Leu Lys Phe
        355                 360                 365

Gln Thr Gly Ser Asn Ser Ala Phe Asp Val Val Glu Val Glu Pro
370                 375                 380

Ala Gly Pro Ala Val Leu Thr Ile Gly Leu Gly His Lys Gly Arg Leu
385                 390                 395                 400

Ala Val Val Leu Asp Tyr Thr Arg Leu Asn Ala Ala Leu Gly Ser Ala
                405                 410                 415

Ala Tyr Val Val Glu Asp Ser Gly Cys Ser Ser Glu Glu Val Ser
            420                 425                 430

Phe Gln Gly Val Gly Ser Gly Ala Thr Leu Val Val Thr Thr Leu Gly
        435                 440                 445

Glu Ser Pro Thr Ala Val Ser Ala
450                 455
```

<210> SEQ ID NO 22
<211> LENGTH: 456
<212> TYPE: PRT

<213> ORGANISM: Toxopolasmosis gondii

<400> SEQUENCE: 22

```
Met Gly Gln Ala Leu Phe Leu Thr Val Leu Pro Val Leu Phe Gly
 1               5                  10                  15

Val Gly Pro Glu Ala Tyr Gly Glu Ala Ser His Ser His Ser Pro Ala
            20                  25                  30

Ser Gly Arg Tyr Ile Gln Gln Met Leu Asp Gln Arg Cys Gln Glu Ile
            35                  40                  45

Ala Ala Glu Leu Cys Gln Ser Gly Leu Arg Lys Met Cys Val Pro Ser
        50                  55                  60

Ser Arg Ile Val Ala Arg Asn Ala Val Gly Ile Thr His Gln Asn Thr
 65                  70                  75                  80

Leu Gln Trp Arg Cys Phe Asp Thr Ala Ser Leu Leu Glu Ser Asn Gln
                85                  90                  95

Glu Asn Asn Gly Val Asn Cys Val Asp Asp Cys Gly His Thr Ile Pro
            100                 105                 110

Cys Pro Gly Gly Val His Arg Gln Asn Ser Asn His Ala Thr Arg His
            115                 120                 125

Glu Ile Leu Ser Lys Leu Val Glu Glu Gly Val Gln Arg Phe Cys Ser
        130                 135                 140

Pro Tyr Gln Ala Ser Ala Asn Lys Tyr Cys Asn Asp Lys Phe Pro Gly
145                 150                 155                 160

Thr Ile Ala Arg Arg Ser Lys Gly Phe Gly Asn Asn Val Glu Val Ala
                165                 170                 175

Trp Arg Cys Tyr Glu Lys Ala Ser Leu Leu Tyr Ser Val Tyr Ala Glu
            180                 185                 190

Cys Ala Ser Asn Cys Gly Thr Thr Trp Tyr Cys Pro Gly Gly Arg Arg
            195                 200                 205

Gly Thr Ser Thr Glu Leu Asp Lys Arg His Tyr Thr Glu Glu Glu Gly
        210                 215                 220

Ile Arg Gln Ala Ile Gly Ser Val Asp Ser Pro Cys Ser Glu Val Glu
225                 230                 235                 240

Val Cys Leu Pro Lys Asp Glu Asn Pro Val Cys Leu Asp Glu Ser
                245                 250                 255

Gly Gln Ile Ser Arg Thr Gly Gly Pro Ser Gln Pro Pro Glu
            260                 265                 270

Met Gln Gln Pro Ala Asp Arg Ser Asp Glu Arg Gly Gly Lys Glu
            275                 280                 285

Gln Ser Pro Gly Gly Glu Ala Gln Pro Asp His Pro Thr Lys Gly Gly
        290                 295                 300

Asn Ile Asp Leu Pro Glu Lys Ser Thr Ser Pro Glu Lys Thr Pro Lys
305                 310                 315                 320

Thr Glu Ile His Gly Asp Ser Thr Lys Ala Thr Leu Glu Glu Gly Gln
                325                 330                 335

Gln Leu Thr Leu Thr Phe Ile Ser Thr Lys Leu Asp Val Ala Val Gly
            340                 345                 350

Ser Cys His Ser Leu Val Ala Asn Phe Leu Asp Gly Phe Leu Lys Phe
            355                 360                 365

Gln Thr Gly Ser Asn Ser Ala Phe Asp Val Val Glu Val Glu Glu Pro
        370                 375                 380

Ala Gly Pro Ala Val Leu Thr Ile Gly Leu Gly His Lys Gly Arg Leu
385                 390                 395                 400
```

```
Ala Val Val Leu Asp Tyr Thr Arg Leu Asn Ala Ala Leu Gly Ser Ala
            405                 410                 415

Ala Tyr Val Val Glu Asp Ser Gly Cys Ser Ser Ser Glu Glu Val Ser
            420                 425                 430

Phe Gln Gly Val Gly Ser Gly Ala Thr Leu Val Val Thr Thr Leu Gly
            435                 440                 445

Glu Ser Pro Thr Ala Val Ser Ala
            450                 455

<210> SEQ ID NO 23
<211> LENGTH: 456
<212> TYPE: PRT
<213> ORGANISM: Toxopolasmosis gondii

<400> SEQUENCE: 23

Met Gly Gln Ala Leu Phe Leu Thr Val Leu Pro Val Leu Phe Gly
 1               5                  10                  15

Val Gly Pro Glu Ala Tyr Gly Glu Ala Ser His Ser His Ser Pro Ala
            20                  25                  30

Ser Gly Arg Tyr Ile Gln Gln Met Leu Asp Gln Arg Cys Gln Glu Ile
        35                  40                  45

Ala Ala Glu Leu Cys Gln Ser Gly Leu Arg Lys Met Cys Val Pro Ser
    50                  55                  60

Ser Arg Ile Val Ala Arg Asn Ala Val Gly Ile Thr His Gln Asn Thr
65                  70                  75                  80

Leu Gln Trp Arg Cys Phe Asp Thr Ala Ser Leu Leu Glu Ser Asn Gln
                85                  90                  95

Glu Asn Asn Gly Val Asn Cys Val Asp Asp Cys Gly His Thr Ile Pro
            100                 105                 110

Cys Pro Gly Gly Val His Arg Gln Asn Ser Asn His Ala Thr Arg His
            115                 120                 125

Glu Ile Leu Ser Lys Leu Val Glu Gly Val Gln Arg Phe Cys Ser
        130                 135                 140

Pro Tyr Gln Ala Ser Ala Asn Lys Tyr Cys Asn Asp Lys Phe Pro Gly
145                 150                 155                 160

Thr Ile Ala Arg Arg Ser Lys Gly Phe Gly Asn Asn Val Glu Val Ala
                165                 170                 175

Trp Arg Cys Tyr Glu Lys Ala Ser Leu Leu Tyr Ser Val Tyr Ala Glu
            180                 185                 190

Cys Ala Ser Asn Cys Gly Thr Thr Trp Tyr Cys Pro Gly Gly Arg Arg
        195                 200                 205

Gly Thr Ser Thr Glu Leu Asp Lys Arg His Tyr Thr Glu Glu Glu Gly
    210                 215                 220

Ile Arg Gln Ala Ile Gly Ser Val Asp Ser Pro Cys Ser Glu Val Glu
225                 230                 235                 240

Val Cys Leu Pro Lys Asp Glu Asn Pro Pro Leu Cys Leu Asp Glu Ser
                245                 250                 255

Gly Gln Ile Ser Arg Thr Gly Gly Pro Ser Gln Pro Glu
            260                 265                 270

Met Gln Gln Pro Ala Asp Arg Ser Asp Glu Arg Gly Gly Lys Glu
        275                 280                 285

Gln Ser Pro Gly Gly Glu Ala Gln Pro Asp His Pro Thr Lys Gly Gly
    290                 295                 300

Asn Ile Asp Leu Pro Glu Lys Ser Thr Ser Pro Glu Lys Thr Pro Lys
305                 310                 315                 320
```

```
Thr Glu Ile His Gly Asp Ser Thr Lys Ala Thr Leu Glu Glu Gly Gln
                325                 330                 335

Gln Leu Thr Leu Thr Phe Ile Ser Thr Lys Leu Asp Val Ala Val Gly
            340                 345                 350

Ser Cys His Ser Leu Val Ala Asn Phe Leu Asp Gly Phe Leu Lys Phe
        355                 360                 365

Gln Thr Gly Ser Asn Ser Ala Phe Asp Val Val Glu Val Glu Glu Pro
    370                 375                 380

Ala Gly Pro Ala Val Leu Thr Ile Gly Leu Gly His Lys Gly Arg Leu
385                 390                 395                 400

Ala Val Val Leu Asp Tyr Thr Arg Leu Asn Ala Ala Leu Gly Ser Ala
                405                 410                 415

Ala Tyr Val Val Glu Asp Ser Gly Cys Ser Ser Ser Glu Glu Val Ser
            420                 425                 430

Phe Gln Gly Val Gly Ser Gly Ala Thr Leu Val Val Thr Thr Leu Gly
        435                 440                 445

Glu Ser Pro Thr Ala Val Ser Ala
    450                 455
```

<210> SEQ ID NO 24
<211> LENGTH: 456
<212> TYPE: PRT
<213> ORGANISM: Toxopolasmosis gondii

<400> SEQUENCE: 24

```
Met Gly Gln Ala Leu Phe Leu Thr Val Leu Pro Val Leu Phe Gly
1               5                   10                  15

Val Gly Pro Glu Ala Tyr Gly Glu Ala Ser His Ser His Ser Pro Ala
                20                  25                  30

Ser Gly Arg Tyr Ile Gln Gln Met Leu Asp Gln Arg Cys Gln Glu Ile
            35                  40                  45

Ala Ala Glu Leu Cys Gln Ser Gly Leu Arg Lys Met Cys Val Pro Ser
        50                  55                  60

Ser Arg Ile Val Ala Arg Asn Ala Val Gly Ile Thr His Gln Asn Thr
65                  70                  75                  80

Leu Gln Trp Arg Cys Phe Asp Thr Ala Ser Leu Leu Glu Ser Asn Gln
                85                  90                  95

Glu Asn Asn Gly Val Asn Cys Val Asp Asp Cys Gly His Thr Ile Pro
            100                 105                 110

Cys Pro Gly Gly Val His Arg Gln Asn Ser Asn His Ala Thr Arg His
        115                 120                 125

Glu Ile Leu Ser Lys Leu Val Glu Glu Gly Val Gln Arg Phe Cys Ser
    130                 135                 140

Pro Tyr Gln Ala Ser Ala Asn Lys Tyr Cys Asn Asp Lys Phe Pro Gly
145                 150                 155                 160

Thr Ile Ala Arg Arg Ser Lys Gly Phe Gly Asn Asn Val Glu Val Ala
                165                 170                 175

Trp Arg Cys Tyr Glu Lys Ala Ser Leu Leu Tyr Ser Val Tyr Ala Glu
            180                 185                 190

Cys Ala Ser Asn Cys Gly Thr Thr Trp Tyr Cys Pro Gly Gly Arg Arg
        195                 200                 205

Gly Thr Ser Thr Glu Leu Asp Lys Arg His Tyr Thr Glu Glu Glu Gly
    210                 215                 220

Ile Arg Gln Ala Ile Gly Ser Val Asp Ser Pro Cys Ser Glu Val Glu
```

```
            225                 230                 235                 240
Val Cys Leu Pro Lys Asp Glu Asn Pro Pro Leu Cys Leu Asp Glu Ser
                245                 250                 255
Gly Gln Ile Ser Arg Thr Gly Gly Pro Ser Gln Pro Pro Glu
            260                 265                 270
Met Gln Pro Ala Asp Arg Ser Asp Glu Arg Gly Gly Lys Glu
            275                 280                 285
Gln Ser Pro Gly Gly Glu Ala Gln Pro Asp His Pro Thr Lys Gly Gly
            290                 295                 300
Asn Ile Asp Leu Pro Glu Lys Ser Thr Ser Pro Glu Lys Thr Pro Lys
305                 310                 315                 320
Thr Glu Ile His Gly Asp Ser Thr Lys Ala Thr Leu Glu Glu Gly Gln
                325                 330                 335
Gln Leu Thr Leu Thr Phe Ile Ser Thr Lys Leu Asp Val Ala Val Gly
                340                 345                 350
Ser Cys His Ser Leu Val Ala Asn Phe Leu Asp Gly Phe Leu Lys Phe
                355                 360                 365
Gln Thr Gly Ser Asn Ser Ala Phe Asp Val Val Glu Val Glu Glu Pro
            370                 375                 380
Ala Gly Pro Ala Val Leu Thr Ile Gly Leu Gly His Lys Gly Arg Leu
385                 390                 395                 400
Ala Val Val Leu Asp Tyr Thr Arg Leu Asn Ala Ala Leu Gly Ser Ala
                405                 410                 415
Ala Tyr Val Val Glu Asp Ser Gly Cys Ser Ser Ser Glu Glu Val Ser
                420                 425                 430
Phe Gln Gly Val Gly Ser Gly Ala Thr Leu Val Val Thr Thr Leu Gly
            435                 440                 445
Glu Ser Pro Thr Ala Val Ser Ala
            450                 455

<210> SEQ ID NO 25
<211> LENGTH: 456
<212> TYPE: PRT
<213> ORGANISM: Toxopolasmosis gondii

<400> SEQUENCE: 25

Met Gly Gln Ala Leu Phe Leu Thr Val Leu Leu Pro Val Leu Phe Gly
1               5                   10                  15
Val Gly Pro Glu Ala Tyr Gly Glu Ala Ser His Ser His Ser Pro Ala
            20                  25                  30
Ser Gly Arg Tyr Ile Gln Gln Met Leu Asp Gln Arg Cys Gln Glu Ile
        35                  40                  45
Ala Ala Glu Leu Cys Gln Ser Gly Leu Arg Lys Met Cys Val Pro Ser
    50                  55                  60
Ser Arg Ile Val Ala Arg Asn Ala Val Gly Ile Thr His Gln Asn Thr
65                  70                  75                  80
Leu Gln Trp Arg Cys Phe Asp Thr Ala Ser Leu Leu Glu Ser Asn Gln
                85                  90                  95
Glu Asn Asn Gly Val Asn Cys Val Asp Asp Cys Gly His Thr Ile Pro
            100                 105                 110
Cys Pro Gly Gly Val His Arg Gln Asn Ser Asn His Ala Thr Arg His
            115                 120                 125
Glu Ile Leu Ser Lys Leu Val Glu Glu Gly Val Gln Arg Phe Cys Ser
        130                 135                 140
```

Pro Tyr Gln Ala Ser Ala Asn Lys Tyr Cys Asn Asp Lys Phe Pro Gly
145                 150                 155                 160

Thr Ile Ala Arg Arg Ser Lys Gly Phe Gly Asn Asn Val Glu Val Ala
            165                 170                 175

Trp Arg Cys Tyr Glu Lys Ala Ser Leu Leu Tyr Ser Val Tyr Ala Glu
        180                 185                 190

Cys Ala Ser Asn Cys Gly Thr Thr Trp Tyr Cys Pro Gly Gly Arg Arg
    195                 200                 205

Gly Thr Ser Thr Glu Leu Asp Lys Arg His Tyr Thr Glu Glu Glu Gly
    210                 215                 220

Ile Arg Gln Ala Ile Gly Ser Val Asp Ser Pro Cys Ser Glu Val Glu
225                 230                 235                 240

Val Cys Leu Pro Lys Asp Glu Asn Pro Pro Leu Cys Leu Asp Glu Ser
                245                 250                 255

Gly Gln Ile Ser Arg Thr Gly Gly Pro Ser Gln Pro Pro Glu
            260                 265                 270

Met Gln Gln Pro Ala Asp Arg Ser Asp Glu Arg Gly Gly Lys Glu
        275                 280                 285

Gln Ser Pro Gly Gly Glu Ala Gln Pro Asp His Pro Thr Lys Gly Gly
    290                 295                 300

Asn Ile Asp Leu Pro Glu Lys Ser Thr Ser Pro Glu Lys Thr Pro Lys
305                 310                 315                 320

Thr Glu Ile His Gly Asp Ser Thr Lys Ala Thr Leu Glu Glu Gly Gln
                325                 330                 335

Gln Leu Thr Leu Thr Phe Ile Ser Thr Lys Leu Asp Val Ala Val Gly
        340                 345                 350

Ser Cys His Ser Leu Val Ala Asn Phe Leu Asp Gly Phe Leu Lys Phe
    355                 360                 365

Gln Thr Gly Ser Asn Ser Ala Phe Asp Val Val Glu Val Glu Glu Pro
    370                 375                 380

Ala Gly Pro Ala Val Leu Thr Ile Gly Leu Gly His Lys Gly Arg Leu
385                 390                 395                 400

Ala Val Val Leu Asp Tyr Thr Arg Leu Asn Ala Ala Leu Gly Ser Ala
                405                 410                 415

Ala Tyr Val Val Glu Asp Ser Gly Cys Ser Ser Ser Glu Glu Val Ser
                420                 425                 430

Phe Gln Gly Val Gly Ser Gly Ala Thr Leu Val Val Thr Thr Leu Gly
        435                 440                 445

Glu Ser Pro Thr Ala Val Ser Ala
450                 455

<210> SEQ ID NO 26
<211> LENGTH: 456
<212> TYPE: PRT
<213> ORGANISM: Toxopolasmosis gondii

<400> SEQUENCE: 26

Met Gly Gln Ala Leu Phe Leu Thr Val Leu Leu Pro Val Leu Phe Gly
1               5                   10                  15

Val Gly Pro Glu Ala Tyr Gly Glu Ala Ser His Ser His Ser Pro Ala
            20                  25                  30

Ser Gly Arg Tyr Ile Gln Gln Met Leu Asp Gln Arg Cys Gln Glu Ile
        35                  40                  45

Ala Ala Glu Leu Cys Gln Ser Gly Leu Arg Lys Met Cys Val Pro Ser
    50                  55                  60

Ser Arg Ile Val Ala Arg Asn Ala Val Gly Ile Thr His Gln Asn Thr
 65                  70                  75                  80

Leu Gln Trp Arg Cys Phe Asp Thr Ala Ser Leu Leu Glu Ser Asn Gln
             85                  90                  95

Glu Asn Asn Gly Val Asn Cys Val Asp Asp Cys Gly His Thr Ile Pro
         100                 105                 110

Cys Pro Gly Gly Val His Arg Gln Asn Ser Asn His Ala Thr Arg His
     115                 120                 125

Glu Ile Leu Ser Lys Leu Val Glu Glu Gly Val Gln Arg Phe Cys Ser
130                 135                 140

Pro Tyr Gln Ala Ser Ala Asn Lys Tyr Cys Asn Asp Lys Phe Pro Gly
145                 150                 155                 160

Thr Ile Ala Arg Arg Ser Lys Gly Phe Gly Asn Asn Val Glu Val Ala
                 165                 170                 175

Trp Arg Cys Tyr Glu Lys Ala Ser Leu Leu Tyr Ser Val Tyr Ala Glu
             180                 185                 190

Cys Ala Ser Asn Cys Gly Thr Thr Trp Tyr Cys Pro Gly Gly Arg Arg
         195                 200                 205

Gly Thr Ser Thr Glu Leu Asp Lys Arg His Tyr Thr Glu Glu Glu Gly
     210                 215                 220

Ile Arg Gln Ala Ile Gly Ser Val Asp Ser Pro Cys Ser Glu Val Glu
225                 230                 235                 240

Val Cys Leu Pro Lys Asp Glu Asn Pro Pro Leu Cys Leu Asp Glu Ser
                 245                 250                 255

Gly Gln Ile Ser Arg Thr Gly Gly Pro Pro Ser Gln Pro Pro Glu
             260                 265                 270

Met Gln Gln Pro Ala Asp Arg Ser Asp Glu Arg Gly Gly Gly Lys Glu
         275                 280                 285

Gln Ser Pro Gly Gly Glu Ala Gln Pro Asp His Pro Thr Lys Gly Gly
     290                 295                 300

Asn Ile Asp Leu Pro Glu Lys Ser Thr Ser Pro Glu Lys Thr Pro Lys
305                 310                 315                 320

Thr Glu Ile His Gly Asp Ser Thr Lys Ala Thr Leu Glu Glu Gly Gln
                 325                 330                 335

Gln Leu Thr Leu Thr Phe Ile Ser Thr Lys Leu Asp Val Ala Val Gly
             340                 345                 350

Ser Cys His Ser Leu Val Ala Asn Phe Leu Asp Gly Phe Leu Lys Phe
         355                 360                 365

Gln Thr Gly Ser Asn Ser Ala Phe Asp Val Val Glu Val Glu Glu Pro
     370                 375                 380

Ala Gly Pro Ala Val Leu Thr Ile Gly Leu Gly His Lys Gly Arg Leu
385                 390                 395                 400

Ala Val Val Leu Asp Tyr Thr Arg Leu Asn Ala Ala Leu Gly Ser Ala
                 405                 410                 415

Ala Tyr Val Val Glu Asp Ser Gly Cys Ser Ser Ser Glu Glu Val Ser
             420                 425                 430

Phe Gln Gly Val Gly Ser Gly Ala Thr Leu Val Val Thr Thr Leu Gly
         435                 440                 445

Glu Ser Pro Thr Ala Val Ser Ala
     450                 455

<210> SEQ ID NO 27
<211> LENGTH: 456

<212> TYPE: PRT
<213> ORGANISM: Toxopolasmosis gondii

<400> SEQUENCE: 27

Met Gly Gln Ala Leu Phe Leu Thr Val Leu Leu Pro Val Leu Phe Gly
1               5                   10                  15

Val Gly Pro Glu Ala Tyr Gly Glu Ala Ser His Ser His Ser Pro Ala
            20                  25                  30

Ser Gly Arg Tyr Ile Gln Gln Met Leu Asp Gln Arg Cys Gln Glu Ile
        35                  40                  45

Ala Ala Glu Leu Cys Gln Ser Gly Leu Arg Lys Met Cys Val Pro Ser
50                  55                  60

Ser Arg Ile Val Ala Arg Asn Ala Val Gly Ile Thr His Gln Asn Thr
65                  70                  75                  80

Leu Gln Trp Arg Cys Phe Asp Thr Ala Ser Leu Leu Glu Ser Asn Gln
                85                  90                  95

Glu Asn Asn Gly Val Asn Cys Val Asp Asp Cys Gly His Thr Ile Pro
            100                 105                 110

Cys Pro Gly Gly Val His Arg Gln Asn Ser Asn His Ala Thr Arg His
        115                 120                 125

Gln Ile Leu Ser Lys Leu Val Glu Glu Gly Val Gln Arg Phe Cys Ser
130                 135                 140

Pro Tyr Gln Ala Ser Ala Asn Lys Tyr Cys Asn Asp Lys Phe Pro Gly
145                 150                 155                 160

Thr Ile Ala Arg Arg Ser Lys Gly Phe Gly Asn Asn Val Glu Val Ala
                165                 170                 175

Trp Arg Cys Tyr Glu Lys Ala Ser Leu Leu Tyr Ser Val Tyr Ala Glu
            180                 185                 190

Cys Ala Ser Asn Cys Gly Thr Thr Trp Tyr Cys Pro Gly Gly Arg Arg
        195                 200                 205

Gly Thr Ser Thr Glu Leu Asp Lys Arg His Tyr Thr Glu Glu Glu Gly
210                 215                 220

Ile Arg Gln Ala Ile Gly Ser Val Asp Ser Pro Cys Ser Glu Val Glu
225                 230                 235                 240

Val Cys Leu Pro Lys Asp Glu Asn Pro Pro Leu Cys Leu Asp Glu Ser
                245                 250                 255

Gly Gln Ile Ser Arg Thr Gly Gly Pro Ser Gln Pro Pro Glu
            260                 265                 270

Met Gln Gln Pro Ala Asp Arg Ser Asp Glu Arg Gly Gly Lys Glu
        275                 280                 285

Gln Ser Pro Gly Gly Glu Ala Gln Pro Asp His Pro Thr Lys Gly Gly
290                 295                 300

Asn Ile Asp Leu Pro Glu Lys Ser Thr Ser Pro Glu Lys Thr Pro Lys
305                 310                 315                 320

Thr Glu Ile His Gly Asp Ser Thr Lys Ala Thr Leu Glu Glu Gly Gln
                325                 330                 335

Gln Leu Thr Leu Thr Phe Ile Ser Thr Lys Leu Asp Val Ala Val Gly
            340                 345                 350

Ser Cys His Ser Leu Val Ala Asn Phe Leu Asp Gly Phe Leu Lys Phe
        355                 360                 365

Gln Thr Gly Ser Asn Ser Ala Phe Asp Val Val Glu Val Glu Pro
370                 375                 380

Ala Gly Pro Ala Val Leu Thr Ile Gly Leu Gly His Lys Gly Arg Leu
385                 390                 395                 400

```
Ala Val Val Leu Asp Tyr Thr Arg Leu Asn Ala Ala Leu Gly Ser Ala
            405                 410                 415

Ala Tyr Val Val Glu Asp Ser Gly Cys Ser Ser Ser Glu Glu Val Ser
            420                 425                 430

Phe Gln Gly Val Gly Ser Gly Ala Thr Leu Val Val Thr Thr Leu Gly
            435                 440                 445

Glu Ser Pro Thr Ala Val Ser Ala
450                 455

<210> SEQ ID NO 28
<211> LENGTH: 456
<212> TYPE: PRT
<213> ORGANISM: Toxopolasmosis gondii

<400> SEQUENCE: 28

Met Gly Gln Ala Leu Phe Leu Thr Val Leu Leu Pro Val Leu Phe Gly
1               5                   10                  15

Val Gly Pro Glu Ala Tyr Gly Glu Ala Ser His Ser His Ser Pro Ala
            20                  25                  30

Ser Gly Arg Tyr Ile Gln Gln Met Leu Asp Gln Arg Cys Gln Glu Ile
        35                  40                  45

Ala Ala Glu Leu Cys Gln Ser Gly Leu Arg Lys Met Cys Val Pro Ser
    50                  55                  60

Ser Arg Ile Val Ala Arg Asn Ala Val Gly Ile Thr His Gln Asn Thr
65                  70                  75                  80

Leu Gln Trp Arg Cys Phe Asp Thr Ala Ser Leu Leu Glu Ser Asn Gln
                85                  90                  95

Glu Asn Asn Gly Val Asn Cys Val Asp Asp Cys Gly His Thr Ile Pro
            100                 105                 110

Cys Pro Gly Gly Val His Arg Gln Asn Ser Asn His Ala Thr Arg His
        115                 120                 125

Glu Ile Leu Ser Lys Leu Val Glu Glu Gly Val Gln Arg Phe Cys Ser
    130                 135                 140

Pro Tyr Gln Ala Ser Ala Asn Lys Tyr Cys Asn Asp Lys Phe Pro Gly
145                 150                 155                 160

Thr Ile Ala Arg Arg Ser Lys Gly Phe Gly Asn Asn Val Glu Val Ala
                165                 170                 175

Trp Arg Cys Tyr Glu Lys Ala Ser Leu Leu Tyr Ser Val Tyr Ala Glu
            180                 185                 190

Cys Ala Ser Asn Cys Gly Thr Thr Trp Tyr Cys Pro Gly Gly Arg Arg
        195                 200                 205

Gly Thr Ser Thr Glu Leu Asp Lys Arg His Tyr Thr Glu Glu Glu Gly
    210                 215                 220

Ile Arg Gln Ala Ile Gly Ser Val Asp Ser Pro Cys Ser Glu Val Glu
225                 230                 235                 240

Val Cys Leu Pro Lys Asp Glu Asn Pro Leu Cys Leu Asp Glu Ser
                245                 250                 255

Gly Gln Ile Ser Arg Thr Gly Gly Pro Ser Gln Pro Pro Glu
            260                 265                 270

Met Gln Gln Pro Ala Asp Arg Ser Asp Glu Arg Gly Gly Lys Glu
        275                 280                 285

Gln Ser Pro Gly Gly Glu Ala Gln Pro Asp His Pro Thr Lys Gly Gly
    290                 295                 300

Asn Ile Asp Leu Pro Glu Lys Ser Thr Ser Pro Glu Lys Thr Pro Lys
```

```
                305                 310                 315                 320
        Thr Glu Ile His Gly Asp Ser Thr Lys Ala Thr Leu Glu Glu Gly Gln
                            325                 330                 335

Gln Leu Thr Leu Thr Phe Ile Ser Thr Lys Leu Asp Val Ala Val Gly
                            340                 345                 350

Ser Cys His Ser Leu Val Ala Asn Phe Leu Asp Gly Phe Leu Lys Phe
                            355                 360                 365

Gln Thr Gly Ser Asn Ser Ala Phe Asp Val Val Glu Val Glu Asp Pro
                            370                 375                 380

Ala Gly Pro Ala Val Leu Thr Ile Gly Leu Gly His Lys Gly Arg Leu
        385                 390                 395                 400

Ala Val Val Leu Asp Tyr Thr Arg Leu Asn Ala Ala Leu Gly Ser Ala
                            405                 410                 415

Ala Tyr Val Val Glu Asp Ser Gly Cys Ser Ser Ser Glu Glu Val Ser
                            420                 425                 430

Phe Gln Gly Val Gly Ser Gly Ala Thr Leu Val Val Thr Thr Leu Gly
                            435                 440                 445

Glu Ser Pro Thr Ala Val Ser Ala
            450                 455

<210> SEQ ID NO 29
<211> LENGTH: 456
<212> TYPE: PRT
<213> ORGANISM: Toxopolasmosis gondii

<400> SEQUENCE: 29

Met Gly Gln Ala Leu Phe Leu Thr Val Leu Leu Pro Val Leu Phe Gly
        1               5                   10                  15

Val Gly Pro Glu Ala Tyr Gly Glu Ala Ser His Ser His Ser Pro Ala
                            20                  25                  30

Ser Gly Arg Tyr Ile Gln Gln Met Leu Asp Gln Arg Cys Gln Glu Ile
                            35                  40                  45

Ala Ala Glu Leu Cys Gln Ser Gly Leu Arg Lys Met Cys Val Pro Ser
            50                  55                  60

Ser Arg Ile Val Ala Arg Asn Ala Val Gly Ile Thr His Gln Asn Thr
        65                  70                  75                  80

Leu Gln Trp Arg Cys Phe Asp Thr Ala Ser Leu Leu Glu Ser Asn Gln
                            85                  90                  95

Glu Asn Asn Gly Val Asn Cys Val Asp Asp Cys Gly His Thr Ile Pro
                            100                 105                 110

Cys Pro Gly Gly Val His Arg Gln Asn Ser Asn His Ala Thr Arg His
                            115                 120                 125

Glu Ile Leu Ser Lys Leu Val Glu Glu Gly Val Gln Arg Phe Cys Ser
            130                 135                 140

Pro Tyr Gln Ala Ser Ala Asn Lys Tyr Cys Asn Asp Lys Phe Pro Gly
        145                 150                 155                 160

Thr Ile Ala Arg Arg Ser Lys Gly Phe Gly Asn Asn Val Glu Val Ala
                            165                 170                 175

Trp Arg Cys Tyr Glu Lys Ala Ser Leu Leu Tyr Ser Val Tyr Ala Glu
                            180                 185                 190

Cys Ala Ser Asn Cys Gly Thr Thr Trp Tyr Cys Pro Gly Gly Arg Arg
                            195                 200                 205

Gly Thr Ser Thr Glu Leu Asp Lys Arg His Tyr Thr Glu Glu Glu Gly
            210                 215                 220
```

```
Ile Arg Gln Ala Ile Gly Ser Val Asp Ser Pro Cys Ser Glu Val Glu
225                 230                 235                 240

Val Cys Leu Pro Lys Asp Glu Asn Pro Val Cys Leu Asp Glu Ser
            245                 250                 255

Gly Gln Ile Ser Arg Thr Gly Gly Pro Ser Gln Pro Pro Glu
        260                 265                 270

Met Gln Gln Pro Ala Asp Arg Ser Asp Glu Arg Gly Gly Lys Glu
            275                 280                 285

Gln Ser Pro Gly Gly Glu Ala Gln Pro Asp His Pro Thr Lys Gly Gly
        290                 295                 300

Asn Ile Asp Leu Pro Glu Lys Ser Thr Ser Pro Glu Lys Thr Pro Lys
305                 310                 315                 320

Thr Glu Ile His Gly Asp Ser Thr Lys Ala Thr Leu Glu Gly Gln
                325                 330                 335

Gln Leu Thr Leu Thr Phe Ile Ser Thr Lys Leu Asp Val Ala Val Gly
            340                 345                 350

Ser Cys His Ser Leu Val Ala Asn Phe Leu Asp Gly Phe Leu Lys Phe
        355                 360                 365

Gln Thr Gly Ser Asn Ser Ala Phe Asp Val Val Glu Val Glu Pro
370                 375                 380

Ala Gly Pro Ala Val Leu Thr Ile Gly Leu Gly His Lys Gly Arg Leu
385                 390                 395                 400

Ala Val Val Leu Asp Tyr Thr Arg Leu Asn Ala Ala Leu Gly Ser Ala
                405                 410                 415

Ala Tyr Val Val Glu Asp Ser Gly Cys Ser Ser Ser Glu Glu Val Ser
            420                 425                 430

Phe Gln Gly Val Gly Ser Gly Ala Thr Leu Val Val Thr Thr Leu Gly
        435                 440                 445

Glu Ser Pro Thr Ala Val Ser Ala
450                 455

<210> SEQ ID NO 30
<211> LENGTH: 456
<212> TYPE: PRT
<213> ORGANISM: Toxopolasmosis gondii

<400> SEQUENCE: 30

Met Gly Gln Ala Leu Phe Leu Thr Val Leu Pro Val Leu Phe Gly
1               5                   10                  15

Val Gly Pro Glu Ala Tyr Gly Glu Ala Ser His Ser His Ser Pro Ala
            20                  25                  30

Ser Gly Arg Tyr Ile Gln Gln Met Leu Asp Gln Arg Cys Gln Glu Ile
        35                  40                  45

Ala Ala Glu Leu Cys Gln Ser Gly Leu Arg Lys Met Cys Val Pro Ser
    50                  55                  60

Ser Arg Ile Val Ala Arg Asn Ala Val Gly Ile Thr His Gln Asn Thr
65                  70                  75                  80

Leu Gln Trp Arg Cys Phe Asp Thr Ala Ser Leu Leu Glu Ser Asn Gln
                85                  90                  95

Glu Asn Asn Gly Val Asn Cys Val Asp Asp Cys Gly His Thr Ile Pro
            100                 105                 110

Cys Pro Gly Gly Val His Arg Gln Asn Ser Asn His Ala Thr Arg His
        115                 120                 125

Glu Ile Leu Ser Lys Leu Val Glu Glu Gly Val Gln Arg Phe Cys Ser
130                 135                 140
```

```
Pro Tyr Gln Ala Ser Ala Asn Lys Tyr Cys Asn Asp Lys Phe Pro Gly
145                 150                 155                 160

Thr Ile Ala Arg Arg Ser Lys Gly Phe Gly Asn Asn Val Glu Val Ala
            165                 170                 175

Trp Arg Cys Tyr Glu Lys Ala Ser Leu Leu Tyr Ser Val Tyr Ala Glu
        180                 185                 190

Cys Ala Ser Asn Cys Gly Thr Thr Trp Tyr Cys Pro Gly Gly Arg Arg
    195                 200                 205

Gly Thr Ser Thr Glu Leu Asp Lys Arg His Tyr Thr Glu Glu Glu Gly
210                 215                 220

Ile Arg Gln Ala Ile Gly Ser Val Asp Ser Pro Cys Ser Glu Val Glu
225                 230                 235                 240

Val Cys Leu Pro Lys Asp Glu Asn Pro Pro Val Cys Leu Asp Glu Ser
            245                 250                 255

Gly Gln Ile Ser Arg Thr Gly Gly Pro Ser Gln Pro Pro Glu
        260                 265                 270

Met Gln Gln Pro Ala Asp Arg Ser Asp Glu Arg Gly Gly Lys Glu
        275                 280                 285

Gln Ser Pro Gly Gly Glu Ala Gln Pro Asp His Pro Thr Lys Gly Gly
    290                 295                 300

Asn Ile Asp Leu Pro Glu Lys Ser Thr Ser Pro Glu Lys Thr Pro Lys
305                 310                 315                 320

Thr Glu Ile His Gly Asp Ser Thr Lys Ala Thr Leu Glu Glu Gly Gln
            325                 330                 335

Gln Leu Thr Leu Thr Phe Ile Ser Thr Lys Leu Asp Val Ala Val Gly
        340                 345                 350

Ser Cys His Ser Leu Val Ala Asn Phe Leu Asp Gly Phe Leu Lys Phe
        355                 360                 365

Gln Thr Gly Ser Asn Ser Ala Phe Asp Val Val Glu Val Glu Pro
    370                 375                 380

Ala Gly Pro Ala Val Leu Thr Ile Gly Leu Gly His Lys Gly Arg Leu
385                 390                 395                 400

Ala Val Val Leu Asp Tyr Thr Arg Leu Asn Ala Ala Leu Gly Ser Ala
            405                 410                 415

Ala Tyr Val Val Glu Asp Ser Gly Cys Ser Ser Ser Glu Glu Val Ser
        420                 425                 430

Phe Gln Gly Val Gly Ser Gly Ala Thr Leu Val Val Thr Thr Leu Gly
        435                 440                 445

Glu Ser Pro Thr Ala Val Ser Ala
    450                 455

<210> SEQ ID NO 31
<211> LENGTH: 456
<212> TYPE: PRT
<213> ORGANISM: Toxopolasmosis gondii

<400> SEQUENCE: 31

Met Gly Gln Ala Leu Phe Leu Thr Val Leu Leu Pro Val Leu Phe Gly
1               5                   10                  15

Val Gly Pro Glu Ala Tyr Gly Glu Ala Ser His Ser His Ser Pro Ala
            20                  25                  30

Ser Gly Arg Tyr Ile Gln Gln Met Leu Asp Gln Arg Cys Gln Glu Ile
        35                  40                  45

Ala Ala Glu Leu Cys Gln Gly Gly Leu Arg Lys Met Cys Val Pro Ser
```

```
                50                  55                  60
Ser Arg Ile Val Ala Arg Asn Ala Val Gly Ile Thr His Gln Asn Thr
 65                  70                  75                  80

Leu Glu Trp Arg Cys Phe Asp Thr Ala Ser Leu Leu Glu Ser Asn Gln
                 85                  90                  95

Glu Asn Asn Gly Val Asn Cys Val Asp Asp Cys Gly His Thr Ile Pro
            100                 105                 110

Cys Pro Gly Gly Val His Arg Gln Asn Ser Asn His Ala Thr Arg His
            115                 120                 125

Glu Ile Leu Ser Lys Leu Val Glu Glu Gly Val Gln Arg Phe Cys Ser
130                 135                 140

Pro Tyr Gln Ala Ser Ala Asn Lys Tyr Cys Asn Asp Lys Phe Pro Gly
145                 150                 155                 160

Thr Ile Ala Arg Arg Ser Lys Gly Phe Gly Asn Asn Val Glu Val Ala
                165                 170                 175

Trp Arg Cys Tyr Glu Lys Ala Ser Leu Leu Tyr Ser Val Tyr Ala Glu
                180                 185                 190

Cys Ala Ser Asn Cys Gly Thr Thr Trp Tyr Cys Pro Gly Gly Arg Arg
            195                 200                 205

Gly Thr Ser Thr Glu Leu Asp Lys Arg His Tyr Thr Glu Glu Glu Gly
210                 215                 220

Ile Arg Gln Ala Ile Gly Ser Val Asp Ser Pro Cys Ser Glu Val Glu
225                 230                 235                 240

Val Cys Leu Pro Lys Asp Glu Asn Pro Pro Val Cys Leu Asp Glu Ser
                245                 250                 255

Gly Gln Ile Ser Arg Thr Gly Gly Pro Ser Gln Pro Pro Glu
            260                 265                 270

Met Gln Gln Pro Ala Asp Arg Ser Asp Glu Arg Gly Gly Lys Glu
            275                 280                 285

Gln Ser Pro Gly Gly Glu Ala Gln Pro Asp His Pro Thr Lys Gly Gly
            290                 295                 300

Asn Ile Asp Leu Pro Glu Lys Ser Thr Ser Pro Glu Lys Thr Pro Lys
305                 310                 315                 320

Thr Glu Ile His Gly Asp Ser Thr Lys Ala Thr Leu Glu Glu Gly Gln
                325                 330                 335

Gln Leu Thr Leu Thr Phe Ile Ser Thr Lys Leu Asp Val Ala Val Gly
                340                 345                 350

Ser Cys His Ser Leu Val Ala Asn Phe Leu Asp Gly Phe Leu Lys Phe
            355                 360                 365

Gln Thr Gly Ser Asn Ser Ala Phe Asp Val Val Glu Val Glu Glu Pro
370                 375                 380

Ala Gly Pro Ala Val Leu Thr Ile Gly Leu Gly His Lys Gly Arg Leu
385                 390                 395                 400

Ala Val Val Leu Asp Tyr Thr Arg Leu Asn Ala Ala Leu Gly Ser Ala
                405                 410                 415

Ala Tyr Val Val Glu Asp Ser Gly Cys Ser Ser Ser Glu Glu Val Ser
            420                 425                 430

Phe Gln Gly Val Gly Ser Gly Ala Thr Leu Val Val Thr Thr Leu Gly
            435                 440                 445

Glu Ser Pro Thr Ala Val Ser Ala
    450                 455

<210> SEQ ID NO 32
```

```
<211> LENGTH: 456
<212> TYPE: PRT
<213> ORGANISM: Toxopolasmosis gondii

```
                385                 390                 395                 400
Ala Val Val Leu Asp Tyr Thr Arg Leu Asn Ala Ala Leu Gly Ser Ala
                    405                 410                 415

Ala Tyr Val Val Glu Asp Ser Gly Cys Ser Ser Glu Glu Val Ser
                420                 425                 430

Phe Gln Gly Val Gly Ser Gly Ala Thr Leu Val Val Thr Thr Leu Gly
                435                 440                 445

Glu Ser Pro Thr Ala Val Ser Ala
    450                 455

<210> SEQ ID NO 33
<211> LENGTH: 456
<212> TYPE: PRT
<213> ORGANISM: Toxopolasmosis gondii

<400> SEQUENCE: 33

Met Gly Gln Ala Leu Phe Leu Thr Val Leu Pro Val Leu Phe Gly
1               5                   10                  15

Val Gly Pro Glu Ala Tyr Gly Glu Ala Ser His Ser His Ser Pro Ala
                20                  25                  30

Ser Gly Arg Tyr Ile Gln Gln Met Leu Asp Gln Arg Cys Gln Glu Ile
            35                  40                  45

Ala Ala Glu Leu Cys Gln Ser Gly Leu Arg Lys Met Cys Val Pro Ser
50                  55                  60

Ser Arg Ile Val Ala Arg Asn Ala Val Gly Ile Thr His Gln Asn Thr
65                  70                  75                  80

Leu Gln Trp Arg Cys Phe Asp Thr Ala Ser Leu Leu Glu Ser Asn Gln
                85                  90                  95

Glu Asn Asn Gly Val Asn Cys Val Asp Asp Cys Gly His Thr Ile Pro
            100                 105                 110

Cys Pro Gly Gly Val His Arg Gln Asn Ser Asn His Ala Thr Arg His
        115                 120                 125

Glu Ile Leu Ser Lys Leu Val Glu Glu Gly Val Gln Arg Phe Cys Ser
    130                 135                 140

Pro Tyr Gln Ala Ser Ala Asn Lys Tyr Cys Asn Asp Lys Phe Pro Gly
145                 150                 155                 160

Thr Ile Ala Arg Arg Ser Lys Gly Phe Gly Asn Asn Val Glu Val Ala
                165                 170                 175

Trp Arg Cys Tyr Glu Lys Ala Ser Leu Leu Tyr Ser Val Tyr Ala Glu
            180                 185                 190

Cys Ala Ser Asn Cys Gly Thr Thr Trp Tyr Cys Pro Gly Gly Arg Arg
        195                 200                 205

Gly Thr Ser Thr Glu Leu Asp Lys Arg His Tyr Thr Glu Glu Glu Gly
    210                 215                 220

Ile Arg Gln Ala Ile Gly Ser Val Asp Ser Pro Cys Ser Glu Val Glu
225                 230                 235                 240

Val Cys Leu Pro Lys Asp Glu Asn Pro Pro Leu Cys Leu Asp Glu Ser
                245                 250                 255

Gly Gln Ile Ser Arg Thr Gly Gly Pro Ser Gln Pro Pro Glu
            260                 265                 270

Met Gln Gln Pro Ala Asp Arg Ser Asp Glu Arg Gly Gly Lys Glu
        275                 280                 285

Gln Ser Pro Gly Gly Glu Ala Gln Pro Asp His Pro Thr Lys Gly Gly
    290                 295                 300
```

Asn Ile Asp Leu Pro Glu Lys Ser Thr Ser Pro Glu Lys Thr Pro Lys
305                 310                 315                 320

Thr Glu Ile His Gly Asp Ser Thr Lys Ala Thr Leu Glu Glu Gly Gln
            325                 330                 335

Gln Leu Thr Leu Thr Phe Ile Ser Thr Lys Leu Asp Val Ala Val Gly
        340                 345                 350

Ser Cys His Ser Leu Val Ala Asn Phe Leu Asp Gly Phe Leu Lys Phe
    355                 360                 365

Gln Thr Gly Ser Asn Ser Ala Phe Asp Val Val Glu Val Glu Glu Pro
    370                 375                 380

Ala Gly Pro Ala Val Leu Thr Ile Gly Leu Gly His Lys Gly Arg Leu
385                 390                 395                 400

Ala Val Val Leu Asp Tyr Thr Arg Leu Asn Ala Ala Leu Gly Ser Ala
            405                 410                 415

Ala Tyr Val Val Glu Asp Ser Gly Cys Ser Ser Ser Glu Glu Val Ser
        420                 425                 430

Phe Gln Gly Val Gly Ser Gly Ala Thr Leu Val Val Thr Thr Leu Gly
    435                 440                 445

Glu Ser Pro Thr Ala Val Ser Ala
    450                 455

<210> SEQ ID NO 34
<211> LENGTH: 198
<212> TYPE: PRT
<213> ORGANISM: Toxopolasmosis gondii

<400> SEQUENCE: 34

Met Ala Leu Ser Ser Leu Asn Asn Ile Arg Pro Phe Ser Gly Leu Leu
1               5                   10                  15

Gly Cys Gly Leu Leu Phe Gly Ala Leu Val Val Val Ala Cys Val
            20                  25                  30

Phe Ser Val Pro Val Glu Ala Gly Val Leu Arg Lys Val Ala Gly Ala
        35                  40                  45

Gly Ser Leu Gln Ala Ser Ile Gly Glu His Asp Phe Phe Asn Asp Tyr
    50                  55                  60

Asp Gln Asp Glu Glu Tyr Arg Lys Arg Gln Glu Leu Gln Asn Gln
65                  70                  75                  80

Ser Pro Glu Glu Val Glu Glu Ala Lys Arg Lys Tyr His Glu Glu Leu
                85                  90                  95

Arg Arg Lys Ala Glu Glu Asp Ala Glu Thr Lys Arg Lys Gln Glu Ala
            100                 105                 110

Val Ile Gln Glu Leu Lys Glu Val Ala Lys Lys Arg Gly Leu Arg Glu
        115                 120                 125

Ala Ala Glu Arg Glu Glu Lys Arg Ile Asp Glu Gln Ala Asn Tyr
    130                 135                 140

Glu Gln Arg Gln Glu Leu Arg Asp Met Asp Ser Ala Met Glu Glu
145                 150                 155                 160

Arg Leu Met Gln Gln Arg Lys Lys Asp Gln Glu Arg Glu Leu Ala
                165                 170                 175

Arg Lys Asn Ser Asp Lys Val Met Glu Glu Leu Lys Glu Lys Leu Ala
            180                 185                 190

Arg Arg Arg Lys Ser Met
        195

<210> SEQ ID NO 35

```
<211> LENGTH: 198
<212> TYPE: PRT
<213> ORGANISM: Toxopolasmosis gondii

<400

```
Glu Gln Arg Gln Gln Glu Leu Arg Asp Met Asp Ser Ala Met Glu Glu
145                 150                 155                 160

Arg Leu Met Gln Gln Arg Lys Lys Asp Gln Glu Glu Arg Glu Leu Ala
            165                 170                 175

Arg Lys Asn Ser Asp Lys Val Met Glu Glu Leu Lys Glu Lys Leu Ala
        180                 185                 190

Arg Arg Arg Lys Ser Met
        195

<210> SEQ ID NO 37
<211> LENGTH: 198
<212> TYPE: PRT
<213> ORGANISM: Toxopolasmosis gondii

<400> SEQUENCE: 37

Met Ala Leu Ser Ser Leu Asn Asn Ile Arg Pro Phe Ser Gly Leu Leu
1               5                   10                  15

Gly Cys Gly Leu Leu Phe Gly Ala Leu Val Val Val Ala Cys Val
            20                  25                  30

Phe Ser Val Pro Val Glu Ala Gly Val Leu Arg Lys Val Ala Gly Ala
            35                  40                  45

Gly Ser Leu Gln Ala Ser Ile Gly Glu His Asp Phe Phe Asn Asp Tyr
        50                  55                  60

Asp Gln Asp Glu Glu Tyr Arg Lys Arg Gln Gln Glu Leu Gln Asn Gln
65                  70                  75                  80

Ser Pro Glu Glu Val Glu Glu Ala Lys Arg Lys Tyr His Glu Glu Leu
                85                  90                  95

Arg Arg Lys Ala Glu Glu Asp Ala Glu Thr Lys Arg Lys Gln Glu Ala
            100                 105                 110

Val Ile Gln Glu Leu Lys Glu Val Ala Lys Lys Arg Gly Leu Arg Glu
        115                 120                 125

Ala Ala Glu Arg Glu Glu Lys Arg Ile Asp Gln Gln Ala Asn Tyr
    130                 135                 140

Glu Gln Arg Gln Gln Glu Leu Arg Asp Met Asp Ser Ala Met Glu Glu
145                 150                 155                 160

Arg Leu Met Gln Gln Arg Lys Lys Asp Gln Glu Glu Arg Glu Leu Ala
            165                 170                 175

Arg Lys Asn Ser Asp Lys Val Met Glu Glu Leu Lys Glu Lys Leu Ala
        180                 185                 190

Arg Arg Arg Lys Ser Met
        195

<210> SEQ ID NO 38
<211> LENGTH: 198
<212> TYPE: PRT
<213> ORGANISM: Toxopolasmosis gondii

<400> SEQUENCE: 38

Met Ala Leu Ser Ser Leu Asn Asn Ile Arg Pro Phe Ser Gly Leu Leu
1               5                   10                  15

Gly Cys Gly Leu Leu Phe Gly Ala Leu Val Val Val Ala Cys Val
            20                  25                  30

Phe Ser Val Pro Val Glu Ala Gly Val Leu Arg Lys Val Ala Gly Ala
            35                  40                  45

Gly Ser Leu Gln Ala Ser Ile Gly Glu His Asp Phe Phe Asn Asp Tyr
        50                  55                  60
```

```
Asp Gln Asp Glu Glu Tyr Arg Lys Arg Gln Gln Glu Leu Gln Asn Gln
65                  70                  75                  80

Ser Pro Glu Glu Val Glu Glu Ala Lys Arg Lys Tyr His Glu Glu Leu
                85                  90                  95

Arg Arg Lys Ala Glu Glu Asp Ala Glu Thr Lys Arg Lys Gln Glu Ala
            100                 105                 110

Val Ile Gln Glu Leu Lys Glu Val Ala Lys Lys Arg Gly Leu Arg Glu
        115                 120                 125

Ala Ala Glu Arg Glu Glu Lys Arg Ile Asp Glu Gln Gln Ala Asn Tyr
130                 135                 140

Glu Gln Arg Gln Gln Glu Leu Arg Asp Met Asp Ser Ala Met Glu Glu
145                 150                 155                 160

Arg Leu Met Gln Gln Arg Lys Lys Asp Gln Glu Glu Arg Glu Leu Ala
                165                 170                 175

Arg Lys Asn Ser Asp Lys Val Met Glu Glu Leu Lys Glu Lys Leu Ala
            180                 185                 190

Arg Arg Arg Lys Ser Met
            195

<210> SEQ ID NO 39
<211> LENGTH: 198
<212> TYPE: PRT
<213> ORGANISM: Toxopolasmosis gondii

<400> SEQUENCE: 39

Met Ala Leu Ser Ser Leu Asn Asn Ile Arg Pro Phe Ser Gly Leu Leu
1               5                   10                  15

Gly Cys Gly Leu Leu Phe Gly Ala Leu Val Val Val Ala Cys Val
            20                  25                  30

Phe Ser Val Pro Val Glu Ala Gly Val Leu Arg Lys Val Ala Gly Ala
            35                  40                  45

Gly Ser Leu Gln Ala Ser Ile Gly Glu His Asp Phe Phe Asn Asp Tyr
        50                  55                  60

Asp Gln Asp Glu Glu Tyr Arg Lys Arg Gln Gln Glu Leu Gln Asn Gln
65                  70                  75                  80

Ser Pro Glu Glu Val Glu Glu Ala Lys Arg Lys Tyr His Glu Glu Leu
                85                  90                  95

Arg Arg Lys Ala Glu Glu Asp Ala Glu Thr Lys Arg Lys Gln Glu Ala
            100                 105                 110

Val Ile Gln Glu Leu Lys Glu Val Ala Lys Lys Arg Gly Leu Arg Glu
        115                 120                 125

Ala Ala Glu Arg Glu Glu Lys Arg Ile Asp Glu Gln Gln Ala Asn Tyr
130                 135                 140

Glu Gln Arg Gln Gln Glu Leu Arg Asp Met Asp Ser Ala Met Glu Glu
145                 150                 155                 160

Arg Leu Met Gln Gln Arg Lys Lys Asp Gln Glu Glu Arg Glu Leu Ala
                165                 170                 175

Arg Lys Asn Ser Asp Lys Val Met Glu Glu Leu Lys Glu Lys Leu Ala
            180                 185                 190

Arg Arg Arg Lys Ser Met
            195

<210> SEQ ID NO 40
<211> LENGTH: 198
<212> TYPE: PRT
```

<213> ORGANISM: Toxopolasmosis gondii

<400> SEQUENCE: 40

Met Ala Leu Ser Ser Leu Asn Asn Ile Arg Pro Phe Ser Gly Leu Leu
1               5                   10                  15

Gly Cys Gly Leu Leu Phe Gly Ala Leu Val Val Val Ala Cys Val
            20                  25                  30

Phe Ser Val Pro Val Glu Ala Gly Val Leu Arg Lys Val Ala Gly Ala
        35                  40                  45

Gly Ser Leu Gln Ala Ser Ile Gly Glu His Asp Phe Phe Asn Asp Tyr
    50                  55                  60

Asp Gln Asp Glu Glu Tyr Arg Lys Arg Gln Gln Glu Leu Gln Asn Gln
65                  70                  75                  80

Ser Pro Glu Glu Val Glu Glu Ala Lys Arg Lys Tyr His Glu Glu Leu
                85                  90                  95

Arg Arg Lys Ala Glu Glu Asp Ala Glu Thr Lys Arg Lys Gln Glu Ala
            100                 105                 110

Val Ile Gln Glu Leu Lys Glu Val Ala Lys Lys Arg Gly Leu Arg Glu
        115                 120                 125

Ala Ala Glu Arg Glu Glu Lys Arg Ile Asp Glu Gln Gln Ala Asn Tyr
    130                 135                 140

Glu Gln Arg Gln Gln Glu Leu Arg Asp Met Asp Ser Ala Met Glu Glu
145                 150                 155                 160

Arg Leu Met Gln Gln Arg Lys Lys Asp Gln Glu Arg Glu Leu Ala
                165                 170                 175

Arg Lys Asn Ser Asp Lys Val Met Glu Glu Leu Lys Glu Lys Leu Ala
            180                 185                 190

Arg Arg Arg Lys Ser Met
        195

<210> SEQ ID NO 41
<211> LENGTH: 198
<212> TYPE: PRT
<213> ORGANISM: Toxopolasmosis gondii

<400> SEQUENCE: 41

Met Ala Leu Ser Ser Leu Asn Asn Ile Arg Pro Phe Ser Gly Leu Leu
1               5                   10                  15

Gly Cys Gly Leu Leu Phe Gly Ala Leu Val Val Val Ala Cys Val
            20                  25                  30

Phe Ser Val Pro Val Glu Ala Gly Val Leu Arg Lys Val Ala Gly Ala
        35                  40                  45

Gly Ser Leu Gln Ala Ser Ile Gly Glu His Asp Phe Phe Asn Asp Tyr
    50                  55                  60

Asp Gln Asp Glu Glu Tyr Arg Lys Arg Gln Gln Glu Leu Gln Asn Gln
65                  70                  75                  80

Ser Pro Glu Glu Val Glu Glu Ala Lys Arg Lys Tyr His Glu Glu Leu
                85                  90                  95

Arg Arg Lys Ala Glu Glu Asp Ala Glu Thr Lys Arg Lys Gln Glu Ala
            100                 105                 110

Val Ile Gln Glu Leu Lys Glu Val Ala Lys Lys Arg Gly Leu Arg Glu
        115                 120                 125

Ala Ala Glu Arg Glu Glu Lys Arg Ile Asp Glu Gln Gln Ala Asn Tyr
    130                 135                 140

Glu Gln Arg Gln Gln Glu Leu Arg Asp Met Asp Ser Ala Met Glu Glu

```
145                 150                 155                 160
Arg Leu Met Gln Gln Arg Lys Lys Asp Gln Glu Glu Arg Glu Leu Ala
                    165                 170                 175

Arg Lys Asn Ser Asp Lys Val Met Glu Glu Leu Lys Glu Lys Leu Ala
                180                 185                 190

Arg Arg Arg Lys Ser Met
            195

<210> SEQ ID NO 42
<211> LENGTH: 198
<212> TYPE: PRT
<213> ORGANISM: Toxopolasmosis gondii

<400> SEQUENCE: 42

Met Ala Leu Ser Ser Leu Asn Asn Ile Arg Pro Phe Ser Gly Leu Leu
1               5                   10                  15

Gly Cys Gly Leu Leu Phe Gly Ala Leu Val Val Val Ala Cys Val
            20                  25                  30

Phe Ser Val Pro Val Glu Ala Gly Val Leu Arg Lys Val Ala Gly Ala
            35                  40                  45

Gly Ser Leu Gln Ala Ser Ile Gly Glu His Asp Phe Phe Asn Asp Tyr
        50                  55                  60

Asp Gln Asp Glu Glu Tyr Arg Lys Arg Gln Gln Glu Leu Gln Asn Gln
65                  70                  75                  80

Ser Pro Glu Glu Val Glu Glu Ala Lys Arg Lys Tyr His Glu Glu Leu
                85                  90                  95

Arg Arg Lys Ala Glu Glu Asp Ala Glu Thr Lys Arg Lys Gln Glu Ala
            100                 105                 110

Val Ile Gln Glu Leu Lys Glu Val Ala Lys Lys Arg Gly Leu Arg Glu
        115                 120                 125

Ala Ala Glu Arg Glu Glu Lys Arg Thr Asp Glu Gln Gln Ala Asn Tyr
        130                 135                 140

Glu Gln Arg Gln Gln Glu Leu Arg Asp Met Asp Ser Ala Met Glu Glu
145                 150                 155                 160

Arg Leu Met Gln Gln Arg Lys Lys Asp Gln Glu Glu Arg Glu Leu Ala
                    165                 170                 175

Arg Lys Asn Ser Asp Lys Val Met Glu Glu Leu Lys Glu Lys Leu Ala
                180                 185                 190

Arg Arg Arg Lys Ser Met
            195

<210> SEQ ID NO 43
<211> LENGTH: 198
<212> TYPE: PRT
<213> ORGANISM: Toxopolasmosis gondii

<400> SEQUENCE: 43

Met Ala Leu Ser Ser Leu Asn Asn Ile Arg Pro Phe Ser Gly Leu Leu
1               5                   10                  15

Gly Cys Gly Leu Leu Phe Gly Ala Leu Val Val Val Ala Cys Ala
            20                  25                  30

Phe Ser Val Pro Val Glu Ala Gly Val Leu Arg Lys Val Ala Gly Ala
            35                  40                  45

Gly Ser Leu Gln Ala Ser Ile Gly Glu His Asp Phe Phe Asn Asp Tyr
        50                  55                  60

Asp Gln Asp Glu Glu Tyr Arg Lys Arg Gln Gln Glu Leu Gln Asn Gln
```

```
                    65                  70                  75                  80
Ser Pro Glu Glu Val Glu Glu Ala Lys Arg Lys Tyr His Glu Glu Leu
                85                  90                  95

Arg Arg Lys Ala Glu Glu Asp Ala Glu Thr Lys Arg Lys Gln Glu Ala
            100                 105                 110

Val Ile Gln Glu Leu Lys Glu Val Ala Lys Lys Arg Gly Leu Arg Glu
        115                 120                 125

Ala Ala Glu Arg Glu Lys Arg Thr Asp Gln Gln Ala Asn Tyr
    130                 135                 140

Glu Gln Arg Gln Gln Glu Leu Arg Asp Met Asp Ser Ala Met Glu Glu
145                 150                 155                 160

Arg Leu Met Gln Gln Arg Lys Lys Asp Gln Glu Arg Glu Leu Ala
                165                 170                 175

Arg Lys Asn Ser Asp Lys Val Met Glu Glu Leu Lys Glu Lys Leu Ala
            180                 185                 190

Arg Arg Arg Lys Ser Met
        195

<210> SEQ ID NO 44
<211> LENGTH: 167
<212> TYPE: PRT
<213> ORGANISM: Toxopolasmosis gondii

<400> SEQUENCE: 44

Met Leu Val Phe Leu Ser Ala Val Phe Leu Gln Asn Gly Ala Phe Phe
1               5                   10                  15

Phe Glu Gln Tyr Gln Ala Ser Ile Gly Glu His Asp Phe Phe Asn Asp
            20                  25                  30

Tyr Asp Gln Asp Glu Glu Tyr Arg Lys Arg Gln Gln Glu Leu Gln Asn
        35                  40                  45

Gln Ser Pro Glu Glu Val Glu Glu Ala Lys Arg Lys Tyr His Glu Glu
    50                  55                  60

Leu Arg Arg Lys Ala Glu Glu Asp Ala Glu Thr Lys Arg Lys Gln Glu
65                  70                  75                  80

Ala Val Ile Gln Glu Leu Lys Glu Val Ala Lys Lys Arg Gly Leu Arg
                85                  90                  95

Glu Ala Ala Glu Arg Glu Lys Arg Ile Asp Glu Gln Gln Ala Asn
            100                 105                 110

Tyr Glu Gln Arg Gln Gln Glu Leu Arg Asp Met Asp Ser Ala Met Glu
        115                 120                 125

Glu Arg Leu Met Gln Gln Arg Lys Lys Asp Gln Glu Glu Arg Glu Leu
    130                 135                 140

Ala Arg Lys Asn Ser Asp Lys Val Met Glu Glu Leu Lys Glu Lys Leu
145                 150                 155                 160

Ala Arg Arg Arg Lys Ser Met
                165

<210> SEQ ID NO 45
<211> LENGTH: 198
<212> TYPE: PRT
<213> ORGANISM: Toxopolasmosis gondii

<400> SEQUENCE: 45

Met Ala Leu Ser Ser Leu Asn Asn Ile Arg Pro Phe Ser Gly Leu Leu
1               5                   10                  15

Gly Cys Gly Leu Leu Phe Gly Ala Leu Val Val Val Val Ala Cys Val
```

```
                20                  25                  30
Phe Ser Val Pro Val Glu Ala Gly Val Leu Arg Lys Val Ala Gly Ala
         35                  40                  45
Gly Ser Leu Gln Ala Ser Ile Gly Glu His Asp Phe Phe Asn Asp Tyr
     50                  55                  60
Asp Gln Asp Glu Glu Tyr Arg Lys Arg Gln Gln Glu Leu Gln Asn Gln
 65                  70                  75                  80
Ser Pro Glu Glu Val Glu Glu Ala Lys Arg Lys Tyr His Glu Glu Leu
                 85                  90                  95
Arg Arg Lys Ala Glu Glu Asp Ala Glu Thr Lys Arg Lys Gln Glu Ala
            100                 105                 110
Val Ile Gln Glu Leu Lys Glu Val Ala Lys Lys Arg Gly Leu Arg Glu
        115                 120                 125
Ala Ala Glu Arg Glu Glu Lys Arg Ile Asp Glu Gln Gln Ala Asn Tyr
    130                 135                 140
Glu Gln Arg Gln Gln Glu Leu Arg Asp Met Asp Ser Ala Met Glu Glu
145                 150                 155                 160
Arg Leu Met Gln Gln Arg Lys Lys Asp Gln Glu Glu Arg Glu Leu Ala
                165                 170                 175
Arg Lys Asn Ser Asp Lys Val Met Glu Glu Leu Lys Glu Lys Leu Ala
            180                 185                 190
Arg Arg Arg Lys Ser Met
        195

<210> SEQ ID NO 46
<211> LENGTH: 198
<212> TYPE: PRT
<213> ORGANISM: Toxopolasmosis gondii

<400> SEQUENCE: 46

Met Ala Leu Ser Ser Leu Asn Asn Ile Arg Pro Phe Ser Gly Leu Leu
 1               5                  10                  15
Gly Cys Gly Leu Leu Phe Gly Ala Leu Val Val Val Ala Cys Val
             20                  25                  30
Phe Ser Val Pro Val Glu Ala Gly Val Leu Arg Lys Val Ala Gly Ala
         35                  40                  45
Gly Ser Leu Gln Ala Ser Ile Gly Glu His Asp Phe Phe Asn Asp Tyr
     50                  55                  60
Asp Gln Asp Glu Glu Tyr Arg Lys Arg Gln Gln Glu Leu Gln Asn Gln
 65                  70                  75                  80
Ser Pro Glu Glu Val Glu Glu Ala Lys Arg Lys Tyr His Glu Glu Leu
                 85                  90                  95
Arg Arg Lys Ala Glu Glu Asp Ala Glu Thr Lys Arg Lys Gln Glu Ala
            100                 105                 110
Val Ile Gln Glu Leu Lys Glu Val Ala Lys Lys Arg Gly Leu Arg Glu
        115                 120                 125
Ala Ala Glu Arg Glu Glu Lys Arg Ile Asp Glu Gln Gln Ala Asn Tyr
    130                 135                 140
Glu Gln Arg Gln Gln Glu Leu Arg Asp Met Asp Ser Ala Met Glu Glu
145                 150                 155                 160
Arg Leu Met Gln Gln Arg Lys Lys Asp Gln Glu Glu Arg Glu Leu Ala
                165                 170                 175
Arg Lys Asn Ser Asp Lys Val Met Glu Glu Leu Lys Glu Lys Leu Ala
            180                 185                 190
```

Arg Arg Arg Lys Ser Met
        195

<210> SEQ ID NO 47
<211> LENGTH: 198
<212> TYPE: PRT
<213> ORGANISM: Toxopolasmosis gondii

<400> SEQUENCE: 47

Met Ala Leu Ser Ser Leu Asn Asn Ile Arg Pro Phe Ser Gly Leu Leu
1               5                   10                  15

Gly Cys Gly Leu Leu Phe Gly Ala Leu Val Val Val Ala Cys Val
            20                  25                  30

Phe Ser Val Pro Val Glu Ala Gly Val Leu Arg Lys Val Ala Gly Ala
        35                  40                  45

Gly Ser Leu Gln Ala Ser Ile Gly Glu His Asp Phe Phe Asn Asp Tyr
    50                  55                  60

Asp Gln Asp Glu Glu Tyr Arg Lys Arg Gln Gln Glu Leu Gln Asn Gln
65                  70                  75                  80

Ser Pro Glu Glu Val Glu Glu Ala Lys Arg Lys Tyr His Glu Glu Leu
                85                  90                  95

Arg Arg Lys Ala Glu Glu Asp Ala Glu Thr Lys Arg Lys Gln Glu Ala
            100                 105                 110

Val Ile Gln Glu Leu Lys Glu Val Ala Lys Lys Arg Gly Leu Arg Glu
        115                 120                 125

Ala Ala Glu Arg Glu Glu Lys Arg Ile Asp Glu Gln Gln Ala Asn Tyr
    130                 135                 140

Glu Gln Arg Gln Gln Glu Leu Arg Asp Met Asp Ser Ala Met Glu Glu
145                 150                 155                 160

Arg Leu Met Gln Gln Arg Lys Lys Asp Gln Glu Glu Arg Glu Leu Ala
                165                 170                 175

Arg Lys Asn Ser Asp Lys Val Met Glu Glu Leu Lys Glu Lys Leu Ala
            180                 185                 190

Arg Arg Arg Lys Ser Met
        195

<210> SEQ ID NO 48
<211> LENGTH: 198
<212> TYPE: PRT
<213> ORGANISM: Toxopolasmosis gondii

<400> SEQUENCE: 48

Met Ala Leu Ser Ser Leu Asn Asn Ile Arg Pro Phe Ser Gly Leu Leu
1               5                   10                  15

Gly Cys Gly Leu Leu Phe Gly Ala Leu Val Val Val Ala Cys Val
            20                  25                  30

Phe Ser Val Pro Val Glu Ala Gly Val Leu Arg Lys Val Ala Gly Ala
        35                  40                  45

Gly Ser Leu Gln Ala Ser Ile Gly Glu His Asp Phe Phe Asn Asp Tyr
    50                  55                  60

Asp Gln Asp Glu Glu Tyr Arg Lys Arg Gln Gln Glu Leu Gln Asn Gln
65                  70                  75                  80

Ser Pro Glu Glu Val Glu Glu Ala Lys Arg Lys Tyr His Glu Glu Leu
                85                  90                  95

Arg Arg Lys Ala Glu Glu Asp Ala Glu Thr Lys Arg Lys Gln Glu Ala
            100                 105                 110

Val Ile Gln Glu Leu Lys Glu Val Ala Lys Lys Arg Gly Leu Arg Glu
115                 120                 125

Ala Ala Glu Arg Glu Glu Lys Arg Ile Asp Glu Gln Gln Ala Asn Tyr
130                 135                 140

Glu Gln Arg Gln Gln Glu Leu Arg Asp Met Asp Ser Ala Met Glu Glu
145                 150                 155                 160

Arg Leu Met Gln Gln Arg Lys Lys Asp Gln Glu Arg Glu Leu Ala
    165                 170                 175

Arg Lys Asn Ser Asp Lys Val Met Glu Glu Leu Lys Glu Lys Leu Ala
            180                 185                 190

Arg Arg Arg Lys Ser Met
        195

<210> SEQ ID NO 49
<211> LENGTH: 198
<212> TYPE: PRT
<213> ORGANISM: Toxopolasmosis gondii

<400> SEQUENCE: 49

Met Ala Leu Ser Ser Leu Asn Asn Ile Arg Pro Phe Ser Gly Leu Leu
1               5                   10                  15

Gly Cys Gly Leu Leu Phe Gly Ala Leu Val Val Val Ala Cys Val
            20                  25                  30

Phe Ser Val Pro Val Glu Ala Gly Val Leu Arg Lys Val Ala Gly Ala
        35                  40                  45

Gly Ser Leu Gln Ala Ser Ile Gly Glu His Asp Phe Phe Asn Asp Tyr
    50                  55                  60

Asp Gln Asp Glu Glu Tyr Arg Lys Arg Gln Gln Glu Leu Gln Asn Gln
65                  70                  75                  80

Ser Pro Glu Glu Val Glu Ala Lys Arg Lys Tyr His Glu Glu Leu
            85                  90                  95

Arg Arg Lys Ala Glu Glu Asp Ala Glu Thr Lys Arg Lys Gln Glu Ala
        100                 105                 110

Val Ile Gln Glu Leu Lys Glu Val Ala Lys Lys Arg Gly Leu Arg Glu
115                 120                 125

Ala Ala Glu Arg Glu Glu Lys Arg Ile Asp Glu Gln Gln Ala Asn Tyr
130                 135                 140

Glu Gln Arg Gln Gln Glu Leu Arg Asp Met Asp Ser Ala Met Glu Glu
145                 150                 155                 160

Arg Leu Met Gln Gln Arg Lys Lys Asp Gln Glu Arg Glu Leu Ala
    165                 170                 175

Arg Lys Asn Ser Asp Lys Val Met Glu Glu Leu Lys Glu Lys Leu Ala
            180                 185                 190

Arg Arg Arg Lys Ser Met
        195

<210> SEQ ID NO 50
<211> LENGTH: 383
<212> TYPE: PRT
<213> ORGANISM: Toxopolasmosis gondii

<400> SEQUENCE: 50

Met Arg Gly Gly Thr Ser Ala Leu Leu His Ala Leu Thr Phe Ser Gly
1               5                   10                  15

Ala Val Trp Met Cys Thr Pro Ala Glu Ala Leu Pro Ile Gln Lys Ser
            20                  25                  30

```
Val Gln Leu Gly Ser Phe Asp Lys Val Val Pro Ser Arg Glu Val Val
             35                  40                  45

Ser Glu Ser Leu Ala Pro Ser Phe Ala Val Thr Glu Thr His Ser Ser
 50                  55                  60

Val Gln Ser Pro Ser Lys Gln Glu Thr Gln Leu Cys Ala Ile Ser Ser
 65                  70                  75                  80

Glu Gly Lys Pro Cys Arg Asn Arg Gln Leu His Thr Asp Asn Gly Tyr
                 85                  90                  95

Phe Ile Gly Ala Ser Cys Pro Lys Ser Ala Cys Cys Ser Lys Thr Met
                100                 105                 110

Cys Gly Pro Gly Gly Cys Gly Glu Phe Cys Ser Ser Asn Trp Ile Phe
            115                 120                 125

Cys Ser Ser Ser Leu Ile Tyr His Pro Asp Lys Ser Tyr Gly Gly Asp
        130                 135                 140

Cys Ser Cys Glu Lys Gln Gly His Arg Cys Asp Lys Asn Ala Glu Cys
145                 150                 155                 160

Val Glu Asn Leu Asp Ala Gly Gly Val His Cys Lys Cys Lys Asp
                165                 170                 175

Gly Phe Val Gly Thr Gly Leu Thr Cys Ser Glu Asp Pro Cys Ser Lys
            180                 185                 190

Arg Gly Asn Ala Lys Cys Gly Pro Asn Gly Thr Cys Ile Val Val Asp
        195                 200                 205

Ser Val Ser Tyr Thr Cys Thr Cys Gly Asp Gly Glu Thr Leu Val Asn
    210                 215                 220

Leu Pro Glu Gly Gly Gln Gly Cys Lys Arg Thr Gly Cys His Ala Phe
225                 230                 235                 240

Arg Glu Asn Cys Ser Pro Gly Arg Cys Ile Asp Asp Ala Ser His Glu
                245                 250                 255

Asn Gly Tyr Thr Cys Glu Cys Pro Thr Gly Tyr Ser Arg Glu Val Thr
            260                 265                 270

Ser Lys Ala Glu Glu Ser Cys Val Glu Gly Val Glu Val Thr Leu Ala
        275                 280                 285

Glu Lys Cys Glu Lys Glu Phe Gly Ile Ser Ala Ser Ser Cys Lys Cys
290                 295                 300

Asp Asn Gly Tyr Ser Gly Ser Ala Ser Ala Thr Ser His His Gly Lys
305                 310                 315                 320

Gly Glu Ser Gly Ser Glu Gly Ser Leu Ser Glu Lys Met Asn Ile Val
                325                 330                 335

Phe Lys Cys Pro Ser Gly Tyr His Pro Arg Tyr His Ala His Thr Val
            340                 345                 350

Thr Cys Glu Lys Ile Lys His Phe Ala Leu Asp Gly Ala Gly Asn His
        355                 360                 365

Asp Thr Thr Thr Tyr Val Ala Arg Arg Arg Tyr Pro Ala Ser Leu
    370                 375                 380

<210> SEQ ID NO 51
<211> LENGTH: 249
<212> TYPE: PRT
<213> ORGANISM: Toxopolasmosis gondii

<400> SEQUENCE: 51

Tyr His Pro Asp Lys Ser Tyr Gly Gly Asp Cys Ser Cys Glu Lys Gln
1               5                   10                  15

Gly His Arg Cys Asp Lys Asn Ala Glu Cys Val Glu Asn Leu Asp Ala
            20                  25                  30
```

Gly Gly Gly Val His Cys Lys Cys Lys Asp Gly Phe Val Gly Thr Gly
            35                  40                  45

Leu Thr Cys Ser Glu Asp Pro Cys Ser Lys Arg Gly Asn Ala Lys Cys
        50                  55                  60

Gly Pro Asn Gly Thr Cys Ile Val Val Asp Ser Val Ser Tyr Thr Cys
65                  70                  75                  80

Thr Cys Gly Asp Gly Glu Thr Leu Val Asn Leu Pro Glu Gly Gly Gln
                85                  90                  95

Gly Cys Lys Arg Thr Gly Cys His Ala Phe Arg Glu Asn Cys Ser Pro
            100                 105                 110

Gly Arg Cys Ile Asp Asp Ala Ser His Glu Asn Gly Tyr Thr Cys Glu
        115                 120                 125

Cys Pro Thr Gly Tyr Ser Arg Glu Val Thr Ser Lys Ala Glu Glu Ser
    130                 135                 140

Cys Val Glu Gly Val Glu Val Thr Leu Ala Glu Lys Cys Glu Lys Glu
145                 150                 155                 160

Phe Gly Ile Ser Ala Ser Ser Cys Lys Cys Asp Asn Gly Tyr Ser Gly
                165                 170                 175

Ser Ala Ser Ala Thr Ser His His Gly Lys Gly Glu Ser Gly Ser Glu
            180                 185                 190

Gly Ser Leu Ser Glu Lys Met Asn Ile Val Phe Lys Cys Pro Ser Gly
        195                 200                 205

Tyr His Pro Arg Tyr His Ala His Thr Val Thr Cys Glu Lys Ile Lys
    210                 215                 220

His Phe Ala Leu Asp Gly Ala Gly Asn His Asp Thr Thr Thr Tyr Val
225                 230                 235                 240

Ala Arg Arg Arg Tyr Pro Ala Ser Leu
            245

<210> SEQ ID NO 52
<211> LENGTH: 3837
<212> TYPE: DNA
<213> ORGANISM: Toxopolasmosis gondii

<400> SEQUENCE: 52

```
tcttctcttc ttccgtactt ttccctgcat tcacacccc tggtatgact ccacaccgcg      60
tgtaaatgtc ccttaggtga cacccgcagc agcgcgtagg aggaagtaga tgtcagtgta     120
gacgttttg agatgagaga cgataacgta aaatgccgcc gataacttct gcattataca     180
cactctctct ccacgcctag gatgacaggt acggcggcac acgaggaaa gtgggggggg     240
ggggggggc gaacagaaag gtcacatgga aggccgctcg actctccact cacgaagtga     300
aggcttcgtc ccgttttgct ggacaacgaa tgcgaacttc ttcactcgct tgtgacacac     360
acaactccag aggcacagag atgtgaagca aagagtggc gtgtgcgtcg cttctgtcgg     420
cggcaagccc cgctccgtct ctttggtggc gattctggtg tgcaccgtgt gccaagaagt     480
tgcgtgtcac gcgacttttg gaaatgcatc aggttcagag tcgttatgtt gcgattcagg     540
ctctcggcag agaatcattt ccctgtaagc tagttgaact cgccttttta aaagcggcag     600
cagtgccctt gtggaaggcc tcactgtgcc tactttcctc gtcctgagtt tttccgcctt     660
cggcctcatt ttttgctcac caaaatcgtg tcctaccgtc aagttttgcc atagactcct     720
acgggaaaaa acaagccggt cgacacggac gacgcccgca gggaagcgtc ccctccgcag     780
aaatcgggag acaactgtcg ttgacggtgc tgcgcgaaag gtcacagagt ttccagtgtg     840
```

```
ttcatcagac ctcactgtgc actgttagcg gccgctgtcc cgcctggtca acaagtatca    900
caccctcgtc cccgccattg gcacggagct cgatgagctg cagtgtcgct tttaggggag    960
tcgtgcaatc acgccgcaac acaggcgtga ttcgatcttc aattgctagg taaccactcg   1020
tgcttggtag ctctgcaatg gctcgagcga cgggggtgat gcaacatgct gctaaaaact   1080
cgacagacgt gtcaccggaa cccacctaaa taggagacca cgggtctctg gtgtgtcgcg   1140
tcgcattctc gcgtcgcatt ctcgcgtcgc aatgaccggc cagttgctcg acgtcgccag   1200
ccgggactga agagcgttca tcgagtcagc agcattgcgt ccccttgctc ggtgaaaaaa   1260
gactctctgg tcgagtctag ctcgtgtcac ttctgtttct aacctccttc gttcaccggt   1320
acacctccga tgtgactttt ggtacacttg ccctgtcgca cgacgcacgc tgtcactcaa   1380
cttgctgcta cgcaatcgct taggttccct cgaaccagcc atcacacaca cacccttttcc   1440
gggaagacgt ttgcgggcgg tgggtcgcag ctcgtcgaga gtgcgtttct gtgcatttct   1500
gtgggcagtg cagcgcgttt gcgcgcctta ctctgtgtgt aacttccttg tccaacactg   1560
gtaaaaatgc gaggcgggac gtccgcgctg ttgcacgcgc tcaccttcag tggggccgtg   1620
tggatgtgca ccccagcgga ggctttgccg attcagaagt ctgtgcagct gggcagcttt   1680
gacaaagttg tgccgagccg cgaagtcgtc tctgagagtc ttgctccgtc tttcgcggtg   1740
actgagactc actcgtctgt gcaatccccc agcaagcagg agacgcaact ctgtgctatc   1800
tcgagtgaag gcaagccatg tcgaaaccgt cagttgcaca ctgacaacgg gtacttcatc   1860
ggggccagtt gccccaagag cgcttgctgc agcaagacca tgtgcggccc cggcggctgc   1920
ggagaattct gctccagcaa ctggattttt tgcagcagtt cgctcatcta ccatcctgac   1980
aaaagctatg gaggagactg cagctgtgaa aagcagggcc atcggtgcga caaaaacgca   2040
gaatgcgtcg aaaacttgga cgcgggtggg ggtgtgcact gcaagtgcaa agacggcttc   2100
gtcggcactg ggttgacttg ctccgaggat ccttgttcaa aaagagggaa cgcgaagtgc   2160
ggacccaacg gacgtgcat cgtcgtcgat tcagtcagct acacatgcac ctgcggcgac   2220
ggcgaaactc tagtgaacct cccggaaggg ggacaaggat gcaagaggac tggatgtcat   2280
gccttcaggg agaactgcag ccctggtaga tgtattgatg acgcctcgca tgagaatggc   2340
tacacctgcg agtgccccac agggtactca cgtgaggtga cttccaaggc ggaggagtcg   2400
tgtgtggaag gagtcgaagt cacgctggct gagaaatgcg agaaggaatt cggcatcagc   2460
gcgtcatcct gcaaatgcga taacggatac tccggatctg cttccgcaac ctcccaccat   2520
gggaaaggag aatcgggatc cgaggggagc ttgagtgaaa aaatgaatat tgtcttcaag   2580
tgccccagtg gctaccatcc aagataccat gcccacaccg tgacgtgtga gaaaattaag   2640
cactttgccc ttgacggggc cggcaaccac gacacgacta cgtatgtcgc aagacgaagg   2700
tacccagcga gtctctgaga gcggagatca gcgcaaagac aagatgcaga gtttgactcg   2760
agaaacaata gtaacacgaa gtaaaaagtc tccacactaa gccaaggatt gagaatattt   2820
cgatttgtgc cgctggcaat agtggccttg gcctagaaag aagttctgca acgaagcgat   2880
cggctcacac gcggatacac agatgggttt gtaccgagaa cgttaggttt gtgaaccgag   2940
ttcaggtaaa acaaagtaga ttgtgccttt acgcagacag cgagggaaaa catgaggaca   3000
cactgccaac taaagcaaga ctgcctcact aattaccacc gacacacgac atggttaccc   3060
ccgcgttttg ccgcgtgcaa agtttgaatt ctgatggttc tcgagtctga aagcctaaac   3120
cgcccaacca tgtatgaaat aagaacccat caaacgtgag acatctctgc cgaagtgcct   3180
acgaaaagaa cgcttctgcc actaggaggt gcggcctctt cattctatga gaacctgctt   3240
```

```
tgtcggtgtc aacctctggg gaaatcgcct gcctttacac attttgctcg ttgtagagca    3300
agggatctgt tgctgcgttt actccaatac aatgatcgcc gtttcgctgt aggcaagcga    3360
tccgaaaatg tacgttcgag tcagcagcta cttgagaagc agccaacgcc gacacttgct    3420
gcgtttgact gaggtgcact cgcaaacagt ctcgtctccc cggggcaatt tctgagagaa    3480
atgcgggaat ggacgtaatg gtgctcttct gtgagtgctc ttccaccaat ttttcgacaa    3540
gtgttttcgt gacagtcgag tatacctttc tatgtcattc tgtctccgtc agtgctatcg    3600
gattcttcct attcctctac cctttctaca gtcgcataca aagctgctga acaagactt     3660 cctttgtcta gggtagttgt acactccaca catatctgac tgaaacctac ggcaggaagt    3720
ctggtcggca ctgtgcttcc ttgttggctt ttcgtcgttt ctttgtctac gagcttcact    3780
gggtccttga cacggcttgt gagcgttgtg ctcaatattc gaccagctgt atttgtg       3837
```

<210> SEQ ID NO 53
<211> LENGTH: 53
<212> TYPE: DNA
<213> ORGANISM: Toxopolasmosis gondii

<400> SEQUENCE: 53

```
actgtggtct ctaggtatga tctaccatcc tgacaaaagc tatggaggag act           53
```

<210> SEQ ID NO 54
<211> LENGTH: 39
<212> TYPE: DNA
<213> ORGANISM: Toxopolasmosis gondii

<400> SEQUENCE: 54

```
acttgttcta gatcagagac tcgctgggta ccttcgtct                            39
```

<210> SEQ ID NO 55
<211> LENGTH: 580
<212> TYPE: PRT
<213> ORGANISM: Toxopolasmosis gondii

<400> SEQUENCE: 55

```
Met Arg Ala Ser Leu Pro Val His Leu Val Val Cys Thr Gln Leu Ser
1               5                   10                  15

Ala Val Trp Phe Gly Val Ala Lys Ala His Gly Gly His Arg Leu Glu
            20                  25                  30

Pro His Val Pro Gly Phe Leu Gln Gly Phe Thr Asp Ile Thr Pro Ala
        35                  40                  45

Gly Asp Asp Val Ser Ala Asn Val Thr Ser Ser Glu Pro Ala Lys Leu
    50                  55                  60

Asp Leu Ser Cys Val His Ser Asp Asn Lys Gly Ser Arg Ala Pro Thr
65                  70                  75                  80

Ile Gly Glu Pro Val Pro Asp Val Ser Leu Glu Gln Cys Ala Ala Gln
                85                  90                  95

Cys Lys Ala Val Asp Gly Cys Thr His Phe Thr Tyr Asn Asp Asp Ser
            100                 105                 110

Lys Met Cys His Val Lys Glu Gly Lys Pro Asp Leu Tyr Asp Leu Thr
        115                 120                 125

Gly Gly Lys Thr Ala Ser Arg Ser Cys Asp Arg Ser Cys Phe Glu Gln
    130                 135                 140

His Val Ser Tyr Glu Gly Ala Pro Asp Val Met Thr Ala Met Val Thr
145                 150                 155                 160
```

```
Ser Gln Ser Ala Asp Cys Gln Ala Ala Cys Ala Ala Asp Pro Ser Cys
            165                 170                 175
Glu Ile Phe Thr Tyr Asn Glu His Asp Gln Lys Cys Thr Phe Lys Gly
            180                 185                 190
Arg Gly Phe Ser Ala Phe Lys Glu Arg Gly Val Leu Gly Val Thr Ser
            195                 200                 205
Gly Pro Lys Gln Phe Cys Asp Glu Gly Lys Leu Thr Gln Glu Glu
            210                 215                 220
Met Glu Asp Gln Ile Ser Gly Cys Ile Gln Leu Ser Asp Val Gly Ser
225                 230                 235                 240
Met Thr Ala Asp Leu Glu Glu Pro Met Glu Ala Asp Ser Val Gly Ala
                    245                 250                 255
Cys Met Glu Arg Cys Arg Cys Asp Gly Arg Cys Thr His Phe Thr Phe
            260                 265                 270
Asn Asp Asn Thr Arg Met Cys Tyr Leu Lys Gly Asp Lys Met Gln Leu
            275                 280                 285
Tyr Ser Ser Pro Gly Asp Arg Thr Gly Pro Lys Ser Cys Asp Ser Ser
            290                 295                 300
Cys Phe Ser Asn Gly Val Ser Tyr Val Asp Asp Pro Ala Thr Asp Val
305                 310                 315                 320
Glu Thr Val Phe Glu Ile Ser His Pro Ile Tyr Cys Gln Val Ile Cys
                    325                 330                 335
Ala Ala Asn Pro Leu Cys Thr Val Phe Gln Trp Tyr Ala Ser Glu Ala
            340                 345                 350
Lys Cys Val Val Lys Arg Lys Gly Phe Tyr Lys His Arg Lys Thr Gly
            355                 360                 365
Val Thr Gly Val Thr Val Gly Pro Arg Glu Phe Cys Asp Phe Gly Gly
            370                 375                 380
Ser Ile Arg Asp Arg Glu Glu Ala Asp Ala Val Gly Ser Asp Asp Gly
385                 390                 395                 400
Leu Asn Ala Glu Ala Thr Met Ala Asn Ser Pro Asp Phe His Asp Glu
            405                 410                 415
Val Glu Cys Val His Thr Gly Asn Ile Gly Ser Lys Ala Gln Thr Ile
            420                 425                 430
Gly Glu Val Lys Arg Ala Ser Ser Leu Ser Glu Cys Arg Ala Arg Cys
            435                 440                 445
Gln Ala Glu Lys Glu Cys Ser His Tyr Thr Tyr Asn Val Lys Ser Gly
            450                 455                 460
Leu Cys Tyr Pro Lys Arg Gly Lys Pro Gln Phe Tyr Lys Tyr Leu Gly
465                 470                 475                 480
Asp Met Thr Gly Ser Arg Thr Cys Asp Thr Ser Cys Leu Arg Arg Gly
            485                 490                 495
Val Asp Tyr Ser Gln Gly Pro Glu Val Gly Lys Pro Trp Tyr Ser Thr
            500                 505                 510
Leu Pro Thr Asp Cys Gln Val Ala Cys Asp Ala Glu Asp Ala Cys Leu
            515                 520                 525
Val Phe Thr Trp Asp Ser Ala Thr Ser Arg Cys Tyr Leu Ile Gly Ser
            530                 535                 540
Gly Phe Ser Ala His Arg Arg Asn Asp Val Asp Gly Val Val Ser Gly
545                 550                 555                 560
Pro Tyr Thr Phe Cys Asp Asn Gly Glu Asn Leu Gln Val Leu Glu Ala
            565                 570                 575
Lys Asp Thr Glu
```

<210> SEQ ID NO 56
<211> LENGTH: 173
<212> TYPE: PRT
<213> ORGANISM: Toxopolasmosis gondii

<400> SEQUENCE: 56

Ser Glu Pro Ala Lys Leu Asp Leu Ser Cys Val His Ser Asp Asn Lys
1               5                   10                  15
Gly Ser Arg Ala Pro Thr Ile Gly Glu Pro Val Pro Asp Val Ser Leu
            20                  25                  30
Glu Gln Cys Ala Ala Gln Cys Lys Ala Val Asp Gly Cys Thr His Phe
        35                  40                  45
Thr Tyr Asn Asp Asp Ser Lys Met Cys His Val Lys Glu Gly Lys Pro
    50                  55                  60
Asp Leu Tyr Asp Leu Thr Gly Gly Lys Thr Ala Ser Arg Ser Cys Asp
65                  70                  75                  80
Arg Ser Cys Phe Glu Gln His Val Ser Tyr Glu Gly Ala Pro Asp Val
                85                  90                  95
Met Thr Ala Met Val Thr Ser Gln Ser Ala Asp Cys Gln Ala Ala Cys
            100                 105                 110
Ala Ala Asp Pro Ser Cys Glu Ile Phe Thr Tyr Asn Glu His Asp Gln
        115                 120                 125
Lys Cys Thr Phe Lys Gly Arg Gly Phe Ser Ala Phe Lys Glu Arg Gly
    130                 135                 140
Val Leu Gly Val Thr Ser Gly Pro Lys Gln Phe Cys Asp Glu Gly Gly
145                 150                 155                 160
Lys Leu Thr Gln Glu Glu Met Glu Asp Gln Ile Ser Gly
                165                 170

<210> SEQ ID NO 57
<211> LENGTH: 3121
<212> TYPE: DNA
<213> ORGANISM: Toxopolasmosis gondii

<400> SEQUENCE: 57 tttctgtgc atctgtgctg caaaacgggc ctctgtgcat tatttcccca ccaacaattg      60
ccgcgtcgat ccgggtcccg ctcaagctct gcagaactag ctctcgata tagatcagta    120
caatcattcg cttctgacaa tcgcatcgac tgagcgacgc gttgatcgtc gactgtcgtg    180
cgtcgcattc gggcatctcg aaccggtgtt gattccctgt gtcattattt cacttccgtc    240
cttctctcgt ggcgatctat aatacgcgtg tgttgttgcg tgcattgctt gtgttgttgt    300
ggatgtgttt tcttttgtga ccgctcacga acaccccacg caaatgaga gcgtcgctcc    360
cggttcacct cgttgtgtgc acgcagctaa gtgccgtttg gtttggagtg ctaaagccc    420
atggtggaca ccgactggaa ccgcatgttc ccggattcct gcaaggcttc actgatatca    480
cgcctgcagg tgatgacgtt agtgccaacg taacaagttc ggagcctgca aaacttgatc    540
tctcttgtgt gcactctgac aataagggat caagggctcc cacaataggc gagccagtgc    600
cagatgtgtc cctggaacaa tgtgctgcgc aatgcaaggc tgttgatggc tgcacacatt    660
tcacttataa tgacgattcg aagatgtgcc atgtgaagga gggaaaaccc gatttatacg    720
atctcacagg aggcaaaaca gcatcgcgca gttgcgatag atcatgcttc gaacaacacg    780
tatcgtatga gggagctcct gacgtgatga cagcgatggt cacgagccag tcagcggact    840

-continued

```
gtcaggctgc gtgtgcggct gacccgagct gcgagatctt cacttataac gaacacgacc    900
agaaatgtac tttcaaagga aggggtttt ctgcgtttaa ggaacgaggg gtgttgggtg     960
tgacttccgg gccgaaacag ttctgcgatg aaggcggtaa attaactcaa gaggagatgg   1020
aagatcagat cagtggctgc attcaattga gtgacgttgg atcaatgact gctgacctgg   1080
aggagcctat ggaggctgat tctgttggcg cttgtatgga acggtgccgc tgtgatggaa   1140
gatgcacgca cttcacgttc aacgataata ctcggatgtg ctacctcaaa ggtgacaaga   1200
tgcagttgta ctcatctcca ggtgacagaa ccggcccaaa gagctgcgat tcaagctgct   1260
tctcgaacgg ggtttcttac gtcgatgatc cggcgacaga tgttgagacc gtattcgaaa   1320
tttcacaccc aatttattgt caagtaatct gcgccgcaaa tccgttgtgt acagtgtttc   1380
agtggtatgc ctccgaggca aagtgcgtcg tcaagagaaa ggggttttac aaacacagaa   1440
aaacaggtgt cacgggagtc acagtgggcc ctcgggagtt ctgcgatttt ggcggtagca   1500
tccgcgaccg agaagaggca gacgccgttg gatcagacga tggcctcaac gcggaagcaa   1560
ctatggcaaa ttctcctgat tttcacgacg aagtagaatg cgtccacacg gcaacattg    1620
ggtcaaaagc acaaaccatt ggagaagtga acgcgcaag tagtttgagt gagtgcagag    1680
ccagatgcca agcggagaaa gaatgcagcc actacactta caatgtaaaa tccggtttgt   1740
gttatccaaa aagaggaaag cctcaatttt ataagtatct tggcgacatg acgggatcca   1800
gaacatgtga tacaagttgc cttaggaggg gagtcgatta ctcacagggc cctgaagtag   1860
gaaagccttg gtattctacg ctgccgacag actgccaagt tgcatgcgac gctgaggatg   1920
cttgcctggt gttcacctgg gattcggcga cgtcacgatg ctacctcatc ggctcaggtt   1980
tctcggcaca tcgacggaac gacgtggatg gcgtggtatc tggaccctat actttctgtg   2040
acaatggcga aaaccttcag gtgcttgaag cgaaagacac agaatgaccc aggagggtgc   2100
cagatacttt gtgtgactgc gacatgcagt catgtactca aagtgttgta catggacagg   2160
aggactttt ttttaagtca ttgcagaggt gcgttttcgg agcagcacta taactgcgtc    2220
agcgactaag cacgccacgt agctgaatga aacgcagcca ccttcgtgta tgtatgcttc   2280
gttttttgtc gctgtgcagt tttgaatcat ttcccttatg ggacatttct gaaaaatgct   2340
ccccgttcgc ttgtagcact atgagagggg ccgaagactg caatggaggt agcgctgcgt   2400
tgaaaagacg aggcgctaca tttcgcgtag cgacaaggcc gtgtagagtt ttgcttttcg   2460
cgagacactg ctctgagtgt catatgcatc aaatgcagtg gtagcacaca gaggtgagaa   2520
gaatgatcac ctgcggggga atggctttgc taaacaacaa ggtcgctgtg tgactttaca   2580
caacgaaact actgtggtga gtgctcagtt gagtgaaaag aaatgccgcg ttatcgtgag   2640
ttctggttcg gtggactttg ccaccgtagt aaaactcaac ctgtaacgga atgcccagtt   2700
ttactgctct ctttaaaggg cgtccacgtt ctctatattc aagctgttta cccacctgcg   2760
tttcggtgca tcgcgcgtgc cacatcaaaa atccaggtaa cggtgcggga cctatgctac   2820
actttatatc tctcagaaag catacaccca ctgattatgg acaacgctgt ggtcgcgttg   2880
taccacaatg caggaatact cagttcacct tgcaagtgtt ctggtgttca ttgcgtgtca   2940
gaagtacaca aaaagagact tctttggcct ccaagtgata cgtaaccgcg gcagtcatga   3000
acagagtcac tcgtgcttct gaaacgcacg tcttctgtac agagacagat gcagtgtgca   3060
tacaggaagc ccctcgattg ttgccgtagc aggtagccag tagaagaaac aaagacacgg   3120
t                                                                   3121
```

```
<210> SEQ ID NO 58
<211> LENGTH: 54
<212> TYPE: DNA
<213> ORGANISM: Toxopolasmosis gondii

<400> SEQUENCE: 58
actgtggtct ctaggtatga gttcggagcc tgcaaaactt gatctctctt gtgt      54

<210> SEQ ID NO 59
<211> LENGTH: 47
<212> TYPE: DNA
<213> ORGANISM: Toxopolasmosis gondii

<400> SEQUENCE: 59
actgttctag atcagccact gatatgatct tccatctcct cttgagt               47

<210> SEQ ID NO 60
<211> LENGTH: 349
<212> TYPE: PRT
<213> ORGANISM: Toxopolasmosis gondii

<400> SEQUENCE: 60
```

Met Arg Leu Phe Arg Cys Cys Ala Ala Val Val Ala Ala Glu Ser
1               5                   10                  15

Leu Leu Trp Leu Lys Asn Gly Ser Pro Phe Phe Ala Phe Leu Pro Gly
                20                  25                  30

Asn Gly Glu Ile Ala Asp Asn Cys Ser Gly Asn Pro Cys Gly Gly Thr
            35                  40                  45

Ala Ala Gly Thr Cys Ile Asn Thr Pro Ser Gly Tyr Asp Cys Arg Cys
        50                  55                  60

Glu Pro Gly Tyr Val Leu Gly Val Glu Asn Asp Gln Val Thr Cys Met
65                  70                  75                  80

Met Pro Ser Gly Val Pro Met Ala Asn Phe Val Gln Leu Ser Glu Lys
                85                  90                  95

Pro Ala Ala Cys Ser Ser Asn Pro Cys Gly Pro Glu Ala Ala Gly Thr
            100                 105                 110

Cys Asn Glu Thr Asn Ser Gly Tyr Ile Cys Arg Cys Asn Gln Gly Tyr
        115                 120                 125

Arg Ile Ser Leu Asp Gly Thr Gly Asn Val Thr Cys Ile Val Arg Gln
    130                 135                 140

Glu Ser Gly Cys Glu Glu Asn Gly Cys Gly Pro Pro Asp Ala Val Gln
145                 150                 155                 160

Ser Cys Arg Arg Leu Thr Gly Thr Ala Gly Arg Leu Cys Val Cys Lys
                165                 170                 175

Glu Asn Phe Ile Ala Thr Ile Asp Ala Ser Ala His Ile Thr Cys Lys
            180                 185                 190

Arg Val Pro Pro His Tyr Arg Lys Pro Pro Phe Glu Phe Gly Lys Gly
        195                 200                 205

Gly His Pro Val Asp Ser Glu Pro Ser Lys Arg Gln Arg Glu Asp Glu
    210                 215                 220

Gly Glu Ser Arg Glu Pro Glu Ser Asp Ser Thr Glu Pro Gly Arg Asp
225                 230                 235                 240

Gln Glu Arg Arg Thr Pro Leu Glu Glu Ser Gln Glu Pro Glu Gly Ser
                245                 250                 255

Thr Pro Asp Ser Gln Gln Ser Arg Gly Gly Ser Gly Ser Asp Ser Thr
            260                 265                 270

Glu Ser Glu Glu Gln Gly Lys Glu Arg Glu Glu Gly Ser Gly His Ala

```
                275                 280                 285
Gly Ala Ile Ala Gly Val Ile Gly Leu Leu Leu Ser Ala
            290                 295                 300

Ala Gly Ala Gly Val Ala Tyr Met Arg Lys Ser Gly Ser Gly Gly
305                 310                 315                 320

Glu Glu Ile Glu Tyr Glu Arg Gly Ile Glu Ala Ala Glu Ala Ser Glu
                325                 330                 335

Val Glu Val Leu Val Asp Leu Asp Ser Lys Thr Trp Asp
            340                 345
```

<210> SEQ ID NO 61
<211> LENGTH: 326
<212> TYPE: PRT
<213> ORGANISM: Toxopolasmosis gondii

<400> SEQUENCE: 61

```
Ser Pro Phe Phe Ala Phe Leu Pro Gly Asn Gly Glu Ile Ala Asp Asn
1               5                   10                  15

Cys Ser Gly Asn Pro Cys Gly Gly Thr Ala Ala Gly Thr Cys Ile Asn
                20                  25                  30

Thr Pro Ser Gly Tyr Asp Cys Arg Cys Glu Pro Gly Tyr Val Leu Gly
            35                  40                  45

Val Glu Asn Asp Gln Val Thr Cys Met Met Pro Ser Gly Val Pro Met
        50                  55                  60

Ala Asn Phe Val Gln Leu Ser Glu Lys Pro Ala Ala Cys Ser Ser Asn
65                  70                  75                  80

Pro Cys Gly Pro Glu Ala Ala Gly Thr Cys Asn Glu Thr Asn Ser Gly
                85                  90                  95

Tyr Ile Cys Arg Cys Asn Gln Gly Tyr Arg Ile Ser Leu Asp Gly Thr
            100                 105                 110

Gly Asn Val Thr Cys Ile Val Arg Gln Glu Ser Gly Cys Glu Glu Asn
        115                 120                 125

Gly Cys Gly Pro Pro Asp Ala Val Gln Ser Cys Arg Arg Leu Thr Gly
130                 135                 140

Thr Ala Gly Arg Leu Cys Val Cys Lys Glu Asn Phe Ile Ala Thr Ile
145                 150                 155                 160

Asp Ala Ser Ala His Ile Thr Cys Lys Arg Val Pro Pro His Tyr Arg
                165                 170                 175

Lys Pro Pro Phe Glu Phe Gly Lys Gly Gly His Pro Val Asp Ser Glu
            180                 185                 190

Pro Ser Lys Arg Gln Arg Glu Asp Glu Gly Glu Ser Arg Glu Pro Glu
        195                 200                 205

Ser Asp Ser Thr Glu Pro Gly Arg Asp Gln Glu Arg Arg Thr Pro Leu
210                 215                 220

Glu Glu Ser Gln Glu Pro Glu Gly Ser Thr Pro Asp Ser Gln Gln Ser
225                 230                 235                 240

Arg Gly Gly Ser Gly Ser Asp Ser Thr Glu Ser Glu Glu Gln Gly Lys
                245                 250                 255

Glu Arg Glu Glu Gly Ser Gly His Ala Gly Ala Ile Ala Gly Gly Val
            260                 265                 270

Ile Gly Gly Leu Leu Leu Ser Ala Ala Gly Ala Gly Val Ala Tyr
        275                 280                 285

Met Arg Lys Ser Gly Ser Gly Gly Glu Glu Ile Glu Tyr Glu Arg
    290                 295                 300
```

```
Gly Ile Glu Ala Ala Glu Ala Ser Glu Val Glu Val Leu Val Asp Leu
305                 310                 315                 320

Asp Ser Lys Thr Trp Asp
                325

<210> SEQ ID NO 62
<211> LENGTH: 3394
<212> TYPE: DNA
<213> ORGANISM: Toxopolasmosis gondii

<400> SEQUENCE: 62
cagtccggag cacactccta caataaactt gatacgtgtc attttgtgaa acgacacagc      60
acataaccac tcggactgtc tcacgaagct gtagggcgga ttcaccaatg atctttcgca     120
gccgatccaa aactacttgc ccacttccgg tgtacgtaca tcgcgcgaca tgagaggcat     180
tcattgtttt ccatagaaaa cactactgga caaccattcg gtagcgcaca agttgagcct     240
ctgacaaatc tttcctcatc acgtgaatac acgctgcgtg attcgtcagt gactccactg     300
tggtctttaa ccaccatcag agtcctgtaa gcatcctttg tttccgttta aaatgcctgc     360
cagatggcac gacgccgtct ggttttgccg gctttctccg agtcctatta gactttgatg     420
ccttacggct ttttttaag aatggttctt ttgagatttg ccgactttcc agttccgcca      480
ccagacgctc ctgttgaact gccaccggca cgatgcagta ttccgccacg aaaacgcgca     540
ccgcaagctc cgctaccatt aaacgggttt cgtctgcttt agatgtttcc ttccgcgtca     600
tcaaggcaaa agcattgcca ctgatgttac cgaagctttc ccgccatgct gcgcacaatg     660
cccaatcttc cgtcacggac ctcttccggt aaccacctaa aggaggatta ctgggcaacc     720
caaaacgctg caacaagaag cacagtccag gtgtcgctag attcgagcct gcatggtcgt     780
tccgtagctc catacaacaa ttctctgtgt gacggcgaga ggagtaacgc gctagtgtgt     840
gtcagcgacg cggcagtcga tccgatcctg caacaggcag aggtgtgtcg atgctcagtg     900
atgcgacggc gtatctgaag aggactgtag ctccaccacg accttcgtgg gagcacgaag     960
tgtactctgt tgtcgtcggt ctcgtatttt tttgagttgt gtacttcgct gcaagaggag    1020
ggtgagattc gacatctgtg ggcgtttggg atcgtgatga catcgactgt gctttgatat    1080
atgatgtgtt ttttttcgat tggatgagca cattccagta agcttcctgc cgcgcgtctc    1140
tgctatgagg ctcttccggt gctgtgctgc ggccgttgtg gcggccgaat cgttactgtg    1200
gctgaagaac ggctccccgt tttttgcctt tcttcctggg aatggagaga ttgcagacaa    1260
ctgctctggg aatccatgcg gtggcaccgc agctggtacg tgcataaaca caccatctgg    1320
atatgattgc aggtgcgaac caggctacgt tctgggcgtt gaaaatgacc aggtcacgtg    1380
catgatgccc tcaggtgtac ccatggctaa ttttgtacag ctgtcggaaa gcctgcagc    1440 ttgcagctca aaccctgtg gacctgaggc agccggcacc tgcaacgaga caaacagtgg    1500
ttacatttgc cgctgtaatc aaggctacag aatatctctc gacgggacag gaaacgtgac    1560
atgtattgta agacaggaaa gcggctgtga ggaaaacggg tgtgggccgc cagatgcagt    1620
acagagttgc cgccgactaa cagggacggc aggtcgacta tgtgtatgca aggaaaactt    1680
tatagcgaca tcgacgcca gtgcccatat cacctgcaag cgtgtgcctc cccattatag     1740
gaagcctccc ttcgaatttg gcaagggagg tcatcctgtg gactcagaac catcgaaacg    1800
ccagagggaa gatgaaggtg aaagtcgtga gcctgaaagc gactcaacag aaccggggag    1860
agatcaggaa agaagaacac cacttgagga aagccaggaa ccggaaggaa gcaccccgga    1920
cagtcagcag agccgaggtg gttctggtag cgacagtacc gagagcgagg aacaaggaaa    1980
```

```
ggagagagag gaaggaagtg gacatgctgg tgcgatcgct gggggagtta ttggaggcct      2040
gttacttctg agcgctgccg gagcgggtgt tgcatacatg agaaagagtg ggagcggtgg      2100
aggggaggag atagaatacg agaggggtat cgaggctgca gaggccagtg aagtcgaagt      2160
cctcgttgat ttggatagca aaacatggga ttaaacacgtt ctcggctgag acttcacaat     2220
gtagggtgtc gctggcagat cagctgcaat gcgagaggtg acgcgagtag tgagcaccgc      2280
ttcttttaag cgcggacatt gtgctcggtc ttctgtcacc cccgaatcaa aacacatgta      2340
tgataatagt tcctgttgac ttcccctgcc gacaaagaac tgctgtgtcg aggccggctt      2400
ctgtgcactc atcccaaatg agatggactg atgttttaga gacacctcat cgccgacgga      2460
aaccatcagc tcccagagaa actatgctgc gtcgtttttt aggtgatctg ttgcgtaatg      2520
cgcaccttca tatcatctgt gtgttgactg tttggtcgtt ttccgtttag tcaaatgaat      2580
gcagtgaaat gcagggaatt tagcagacac cgagaactgt cctcttgttc tgtgcgcgag      2640
ttgtttttaa cgtatagcga tgcgtttgca cttgatatta ccctaagcca tcagtgggta      2700
tttagaggag cccacaggtg atgggggtga tccctgtttc ttgtcatttg gcttgtaggg      2760
ttcgctggaa ctatctggtg tcacggaaga gtggctttac tgtctgtccc caaacgcaag      2820
gcatcagtgt aaccccgata ggactctgga gacttctgct tcactgccgc gttgcaattt      2880
tcccgcgtca tgtggcaata acggtaattc cacgtgcacg ccgcataccg gatctttgct      2940
cccaggcttt cttatgaggt cggcatacgt acagcggcgg cgtacctccg ctctagagaa      3000
gaccggtcca accgactttg aacagcatgc ttgtgaatga gtgcttaaac accctgaagt      3060
gatggtggaa tgtagcagtc tgggacggtt gatgcgagga tatcaccatt agcatagact      3120
accttgctct ttagcgaggc gagacaactt atttaggtag ccatgaaaca cctcgatagt      3180
atcaatgacg acgtgcggtt caccaacttc cgtcgctagc gcagaaaaca gtcggaaaca      3240
caactcggtg agcacctgaa gtgtcagtac acattcgacc gtcgggaccc gggattccgc      3300
aagtggcacc cgctggtcca gtagcaggaa cctagttcat tcagtataac agatttgggg      3360
cggcaaagag caatttgctc gacctaacgc ttgc                                  3394

<210> SEQ ID NO 63
<211> LENGTH: 44
<212> TYPE: DNA
<213> ORGANISM: Toxopolasmosis gondii

<400> SEQUENCE: 63
actgtgtgct ctaggtatgt ccccgttttt tgcctttctt cctg                       44

<210> SEQ ID NO 64
<211> LENGTH: 39
<212> TYPE: DNA
<213> ORGANISM: Toxopolasmosis gondii

<400> SEQUENCE: 64
actgttctag attaatccca tgttttgcta tccaaatca                             39
```